US008137961B2

(12) United States Patent (10) Patent No.: US 8,137,961 B2
Rommens (45) Date of Patent: Mar. 20, 2012

(54) PLANT-SPECIFIC GENETIC ELEMENTS AND TRANSFER CASSETTES FOR PLANT TRANSFORMATION

(75) Inventor: Caius Rommens, Boise, ID (US)

(73) Assignee: J.R. Simplot Company, Boise, ID (US)

( * ) Notice: Subject to any disclaimer, the term of this patent is extended or adjusted under 35 U.S.C. 154(b) by 902 days.

(21) Appl. No.: 11/369,018

(22) Filed: Mar. 7, 2006

(65) Prior Publication Data

US 2006/0265788 A1    Nov. 23, 2006

Related U.S. Application Data

(63) Continuation-in-part of application No. 11/220,408, filed on Sep. 7, 2005.

(60) Provisional application No. 60/607,586, filed on Sep. 8, 2004, provisional application No. 60/684,525, filed on May 26, 2005, provisional application No. 60/698,938, filed on Jul. 14, 2005.

(51) Int. Cl.
*C12N 15/82* (2006.01)
*C12N 15/63* (2006.01)
*C12N 15/09* (2006.01)
*C07H 21/04* (2006.01)

(52) U.S. Cl. .................. 435/320.1; 536/23.1; 536/23.2; 536/24.1; 800/278; 800/291

(58) Field of Classification Search .................. None
See application file for complete search history.

(56) References Cited

U.S. PATENT DOCUMENTS

| | | | |
|---|---|---|---|
| 5,256,558 A | 10/1993 | Coruzzi et al. | |
| 6,441,277 B1 * | 8/2002 | Barry et al. .................. | 800/298 |
| 6,521,458 B1 | 2/2003 | Gutterson et al. | |
| 2003/0221213 A1 | 11/2003 | Rommens et al. | |
| 2004/0003434 A1 | 1/2004 | Weeks et al. | |
| 2004/0107455 A1 | 6/2004 | Rommens et al. | |
| 2005/0034188 A1 | 2/2005 | Weeks et al. | |

FOREIGN PATENT DOCUMENTS

| | | |
|---|---|---|
| WO | WO 03/069980 | 8/2003 |
| WO | WO 03/069980 A2 | 8/2003 |
| WO | WO 03/079765 | 10/2003 |
| WO | WO 2005/004585 | 1/2005 |
| WO | WO 2005/029944 | 4/2005 |
| WO | WO 2005/121346 A1 | 12/2005 |
| WO | WO 2006/029076 | 3/2006 |

OTHER PUBLICATIONS

Cook et al 1992 Journal of Bacteriology 174:6238-6246.*
Caplan et al 1985 Journal of Bacteriology 161:655-664.*
PCT Annex to Form PCT/ISA/206 Communication Relating to the Results of the Partial International Search Report, pp. 1-3, mailed Sep. 2, 2008.
PCT Notification of Transmittal of The International Search Report and the Written Opinion of the International Searching Authority, or the Declaration, mailed Sep. 9, 2008.
Greco et al., "Transposon Insertional Mutagenesis in Rice", *Plant Physiology*, Mar. 2001, pp. 1175-1177, vol. 125, No. 3, American Society of Plant Physiologists, USA.
Chiurazzi et al., "Termini and Telomeres in T-DNA Transformation", *Plant Molecular Biology*, Jan. 1994, pp. 923-934, vol. 26, No. 3, Kluwer Academic Publishers, Belgium.
PCT International Search Report for International Application No. PCT/US2007/005709, 5 pages.
Rommens et al., "Improving Potato Storage and Processing Characteristics through All-Native DNA Transformation", *J. Agric. Food Chem.*, 2006, vol. 54, pp. 9882-9887.
Rommens et al., "The Intragenic Approach as a New Extension to Traditional Plant Breeding", *Trends in Plant Science.*, Sep. 2007, vol. 12, No. 9, pp. 397-408.
Waters et al., "Sequence identity in the nick regions of IncP plasmid transfer origins and T-DNA borders of *Agrobacterium* Ti Plasmids," *Proc. Natl. Acad. Sci. USA*, 1991, vol. 88, pp. 1456-1460.
Rommens, et al., "Plant-Derived Transfer DNAs", *Plant Physiology*, Nov. 2005, vol. 139, pp. 1338-1349.
"*Trifolium* pretense cDNA clone: RCE26865" XP002460476 Database EMBL (Online) retrieved from EBI Accession No. EMBL:BB920788, Jan. 6, 2006.
"mtel-22021RM1 BAC end, cultivar Jemalong A17 of *Medicago truncatula*" XP002460477 Database EMBL (Online) retrieved from EBI Accession No. EMBL: CR303385, Feb. 28, 2004.
"OG_ABa0160P11.r OG_ABa *Oryza* granulate genomic clone OG_ABa0160P11 3', genomic survey sequence" XP002460478 Database EMBL (Online) retrieved from EBI Accession No. EMBL: DX130638, Jan. 22, 2006.
"*Medicago truncatula* chromosome 6 clone mth2-12k10, Working Draft Sequence, 2 ordered pieces" XP002460479 Database EMBL (Online) retrieved from EBI Accession No. EMBL: AC146583, Sep. 4, 2003.
"mth2-152I13FM1 BAC end, cultivar Jemalong A17 of *Medicago truncatula*" XP002460480 Database EMBL (Online) retrieved from EBI Accession No. EMBL:CR484497, Jun. 11, 2004.
Rommens et al., "Crop Improvement through Modification of the Plant's Owned Genome," *Plant Physiology*, May 2004, vol. 135, pp. 421-431.
Bevan, M., "Binary *Agrobacterium* Vectors for Plant Transformation," *Nucleic Acids Research*, vol. 12 No. 22, 1984, pp. 8711-8721.
Casas-Flores, et al., "Three Decades of Fungal Transformation: Novel Technologies," *Methods Mol. Biol.* , 2004; 267:315-325.
Garbarino, J.E. and Belknap W.R., "Isolation of Ubiquitin-Ribosomal Protein Gene (Ubi3) from Potato and Expression of Its Promoter in Transgenic Plants," *Plant Mol Biol.* Jan. 1994; 24(1): pp. 119-127.
Hansen et al., "A T-DNA Transfer Stimulator Sequence in the Vicinity of the Right Border of pRi8196", *Plant Mol Biol.*, Oct. 1992; 20(1): 113-112.
Houba-Herin, et al. , "Transposition of a Ds Element from a Plasmid into the Plant Genome of *Nicotiana plumbaginifloia* Proto-Plast Derived Cells," *The Plant Journal*, 1994, 6(1), pp. 55-66.

(Continued)

Primary Examiner — Brent T Page
(74) Attorney, Agent, or Firm — Foley & Lardner LLP

(57) ABSTRACT

The present invention provides nucleic acid molecules and sequences, particularly those identified and obtained from plants, that are useful for transferring and integrating one polynucleotide into another via plant transformation techniques.

27 Claims, 10 Drawing Sheets

OTHER PUBLICATIONS

Huang and Kowalski, "Web-Thermodyn: Sequence Analysis Software for profiling DNA Helical Stability", *Nucleic Acids Research*, vol. 31, No. 13. 2003, pp. 3819-3821.

Kunik, et al., "Genetic Transformation of HeLa Cells by *Agrobacterium*," *Proc. Natl. Acad. Sci. USA*, vol. 98, No. 4, 2001, pp. 1871-1876.

Laufs, et al., "Wheat Dwarf Virus Ac/Ds Vectors: Expression and Excision of Transposable Elements Introduced into Various Cereals by a Viral Replicon." *Proc. Natl. Acad. Aci. USA*, Oct. 1990, vol. 87, pp. 7752-7756.

Neidle, S. and Parkinson, G.N., "The Structure of Telomeric DNA", *Curr. Opin .Struct. Biol.*, Jun. 2003; 13(3): pp. 275-283.

Rommens, C.M., "All-Native DNA Transformation: a New Approach to Plant Genetic Engineering," *Trends Plant Sci.*, Sep. 2004; 9(9): 457-464.

Rommens, C.M., "Crop Improvement through Modification of the Plant's Owned Genome," *Plant Physiology*, May 2004, vol. 135, pp. 421-431.

Shen, W.H. and Hohn, B., "Excision of a Transposable Element from a Viral Vector Introduced into Maize Plants by Agroinfection," *Plant Journal*, Jan. 1992; 2(1): pp. 35-42.

Shurvinton, C.E. and Ream, W., "Stimulation of *Agrobacterium tumefaciens* T-DNA Transfer by Overdrive Depends on the Flanking Sequence but Not on a Helical Position with Respect to the Border Repeat," *Journal of Bacteriology*, Sep. 1991, pp. 5558-5563.

Van Haaren et al., "Overdrive Is T-Region Transfer Enhancer Which Stimulates T-Strand Production in *Agrobacterium tumefaciens*", *Nucleic Acids Research*, vol. 15, No. 21, 1987, pp. 8983-8997.

Van Montagu, et al., "The Interaction of *Agrobacterium* Ti-Plasmid DNA and Plant Cells," *Proc R Soc Lond B Biol Sci.*, Nov. 19, 1980; 210 (1180):351-365.

Wirtz, et al., "Ds Excision From Extrachromosomal Geminivirus Vector DNA Is Coupled to Vector DNA Replication in Maize," *The Plant Journal*, 1997, 11(1), pp. 125-135.

Zarudnaya, et al., "Downstream Elements of the Mammalian Pre-MRNA Polyadenylation Signals: Primary, Secondary and Higher-Order Structures", *Nucleic Acids Research*, 2003, vol. 31, No. 5. pp. 1375-1386.

Hansen et al., "A T-DNA Transfer Stimulator Sequence in the Vicinity of the Right Border of pRi8196", *Plant Mol Biol.*, Oct. 1992; pp. 113-122 vol. 20, No. 1, Kluwer Academic Publishers, Belgium.

Huang et al., "Generation of Marker-Free Transgenic Maize by Regular Two-Border *Agrobacterium* Transformation Vectors,"*Transgenic Research*, Oct. 2004, pp. 451-461, vol. 13, Kluwer Academic Publishers, The Netherlands.

Rommens, C.M., "Crop Improvement through Modification of the Plant's Owned Genome," *Plant Physiology*, May 2004, pp. 421-431, vol. 135, American Society of Plant Biologists, USA.

Shurvinton et al., "Stimulation of *Agrobacterium tumefaciens* T-DNA Transfer by Overdrive Depends on the Flanking Sequence but Not on a Helical Position with Respect to the Border Repeat," *Journal of Bacteriology*, Sep. 1991, pp. 5558-5563, vol. 173, No. 17, American Society for Microbiology, USA.

"SALK_004795.29.99.f *Arabidopsis thaliana* TDNA Insertion Lines *Arabidopsis thaliana* Genomic Clone SALK_004795.29.99.f, DNA Sequence" XP002471474 retrieved from EBI Accession No. EMBL:BH746898 Database Accession No. BH746898, 2002.

* cited by examiner

```
                                5'                                                    -4  +1  Right Border/RBA
pSIM551 (SEQ ID 87)  CTTAGAGATCTCAAACAAACATACACAGCGACTTATTCACAACTAGTCATTACCAACAAATATATCCTGGCC  (100 ± 5)
pSIM579 (SEQ ID 89)  TTAGAGATCTCAAACAAACATACACAGCGACTTATTCACAACTAGTACATTACCAACAAATATATCCTGGCC  (48 ± 1)
pSIM578 (SEQ ID 90)  AGAGATCTCAAACAAACATACACAGCGACTTATTCACAACTAGTCAACATTACCAACAAATATATCCTGGCC  (35 ± 4)

pTi15955 (SEQ ID 91) AGAAACAATCAAACAAACATACACAGCGACTTATTCACAGAGCTCAAATTACAACGGTATATATCCTGCCA   (ND)
pTiC58 (SEQ ID 92)   GCCCTTTTAAATATCCGATTATTCTAATAAACGCTCTTTTCTCTTAGGTTTACCCGCCAATATATCCTGTCA (ND)
pRi2659 (SEQ ID 93)  TGACGAACTGACGAACTGACGAACTGACGAACTGACGAACTGACGAACTAGACAAGGGGATATATCCTGTCA (ND)
pRiA4 (SEQ ID 94)    TAACAATTGAACAATTGAACAATTGAACAATTGAACAAACATGACAGGAACATATATCCTGTCA         (ND)
pRi8196 (SEQ ID 95)  TAGACATTGCACATCCAAAGGCAGGCACGTACAAACGAATTTATTTAGCCGACAACGGAATATATCCTGTCA (ND)
pRi1724 (SEQ ID 96)  GAAGGCACGAAGGCACGAAGGCACGAAGGCACGAAGGCACATTACTTTAGAATATATCCTGTCA          (ND)
pRiDB18 (SEQ ID 97)  TCATCACCGCCGTCCTAAACAAACATACCTCCACACAAATTTATCTACCTGACCACAAGATATATCCTGTCA (ND)

pSIM580 (SEQ ID 98)  AGATCTCAAACAAACATACACAGCGACTTATTCACAACTAGTACCAACATTACCAACAAATATATCCTGGCC (120 ± 5)
pSIM844 (SEQ ID 99)  TGACGAACTGACGAACTGACGAACTGACGAACTGACGAACTACCAAACATTACCAACAAATATATCCTGGCC (126 ± 5)
pSIM827 (SEQ ID 100) CTGACGAACTGACGAACTGACGAACTGACGAACTGACGAACTACCAACATTACCAACAAATATATCCTGGCC (7 ± 2)
pSIM581 (SEQ ID 101) TGTCTTTATCTCTTGTTGCCAAAACTGCTCTCGAGTCGAGTCACCAACATTACCAACAAATATATCCTGGCC (22 ± 2)
                                                            ACR domain
```

B

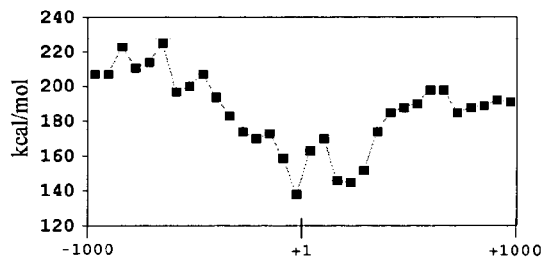

C

```
OD (SEQ ID 88)       CAAACAAACATACACAGCGACTTA
                     +26
pTiC58 (SEQ ID 102)  GTCAGCATCATCACACCAAAAGTTAGGCCCGAATAGTTTGAAATTAGAAAGCTCGCAATTGAG (100 ± 4)
pTi15955 (SEQ ID 103) AACACTGATAGTTTAAACCGAAGGCGGGAAACGACAATCTGATCATGAGCGGAGAATTAAGGG (ND)
pRi2659 (SEQ ID 104) AATAACAATCTCATGTTAGGTAATAATATCACCCAATCAACGCGGCCACGCAATTAACCTGGT (ND)
pRi4 (SEQ ID 230)    GTCAATCAGCAAACAGCAACAGTAGTTATTGTCTGTGAAGATATGTAGGTACCTTTCACCCAC (ND)
pRi8196 (SEQ ID 105) GCACTAATATAAGAAATGTCCTGTCAGCACTAATATAAGAAATGTCCTGCTTTGACGCAAGTG (ND)
pRi1724 (SEQ ID 106) AACCTATTCGTTAATAGGGACGTCGTACCTACTTCCCTTCCAGCGCAGCAAACAGTAGGTCTG (ND)

pSIM108 (SEQ ID 108) GAGGTATAGAGGCATGACTGGCATGATCACTAAATTGATGCCCACAGAGGAGACTTATAACCT (112 ± 5)
pSIM551 (SEQ ID 109) GGGCCCGGTACCCGGGGATCAATTCCCGATCTAGTAACATAGATGACACCGCGCGCGATAATT (100 ± 5)
pSIM920 (SEQ ID 110) GGGCCCGGTTCCCGGGGATCAATTGGGCCCGGTACCCGGGGATCAATTCCCGATCTAGTAACA (60 ± 4)
pSIM781 (SEQ ID 111) GGGCCCGGTACCCGGAGGAGACTCCGATCTACGGCGCCAAATTCAAGGACGGAGAACTTCGTG (89 ± 4)
pSIM582 (SEQ ID 112) CTGAGGACATTCAGAAGATTGGTTATATCCTCTTTCAAGACGCTAAGCAATTAGTGATGCAAA (59 ± 4)
pSIM793 (SEQ ID 113) GAGGTATAGAGGCATGTCTGGCGTGATCACTAAATTGATGCCCGCAGAGGGGACTTATAACAT (105 ± 4)
pSIM843 (SEQ ID 114) GGGGCCCGGTACCCGTTAGGGCTAGCCCGAAAGGGCCGCGGGCAGCCCGTTAGCCCGCATAAC (168 ± 12)
```

Figure 3

A pTi15955 (SEQ ID 116)
TCTCCATATTGACCATCAT*ACTCATTGCTGATCC*ATGTAGATTTCCCGGACATGAAGCC
ATTTACAATTGAATATATCCTGCCGCCGCTGCCGCTTTGCACCC pTiC58 (SEQ ID 117)
TGAATTCAGTACATTAAAA*ACGTCCGCAATGTGT*TATTAAGTTGTCTAAGCGTCAATTT
GTTTACACCACAATATATCCTGCCACCAGCCAGCCAACAGCTCCCCGACC pRi2659 (SEQ ID 118)
ATCTGGTAATATAGCAAAACG*TGCTCAAAAATCGCT*TCAAAGCTCTTGTACTTAGCTC
GTTTACACCACAATATATCCTGCCACCCC pRiA4 (SEQ ID 119)
TACATTTTATATT*CGATAAAGCATGCGT*TAAAACGACTTCGCATGTCCATATCTAATCT
GTTTACATCACAATATATCCTGCCACCCAAGGAGCGACGCCTTCTGGCC

B

>831 (SEQ ID 123)
AAATCTGAT*TGATAAAGGATCGAT*CCTCTAGAGTCGACCTGCAGTACTTACGTACAATT
GTTTACACCACAATATATCCTGCCACCGGATATATTGCCTAGGAGCCAGCCAACAGCT
CCCCGACC

>829 (SEQ ID 124)
AAATCTGAT*TGATAAAGGATCGAT*CCTCTAGAGTCGACCTGCAGTACTTACGTACAATT
GTTTACACCACAATATATCCTGCCACCCGTAGGAGCCAGCCAACAGCTCCCCGACC

C pSIM108 (SEQ ID 125)
TCCTTCATAGCTACACTTTCTAAAGGTACG*ATAGATTTTGGATCA*ACCACACACACTTC
GTTTACACCGGTATATATCCTGCCAAAGCTTCCAGCCAGCCAACAGCTCCCCGACC pSIM843B (SEQ ID 126)
GTAAAAAATAA*AAGTGAAAATTCAAT*GAATTAACACAAATATAAATGTAATATAAAATT
GTATACCTCTGTATACATCCTGCGGCCAAGCTTCCAGCCACGTAGGAGCCAGCCAACA
GCTCCCCGACC pSIM849 (SEQ ID 127)
AATGGAGGTAAGTGTTTCTGCTCAGTGCTGATAGATGTAAATATCTCTGTTATGAAGCC
GTATACCTCTGTATACATCCTGCCGGGATGTATACCCTAGGCCAGCCAGCCAACAGCT
CCCCGACC pSIM781 (SEQ ID 128)
TGTTGAAGGCTTGGATGTGATTAAGAAGGCCGAGGCTGTTGGATCTAGTTCTTGAAGTT
CATTACCAACAAATATATCCTGGCCCCCCTAGGAGCCAGCCAACAGCTCCCCGACC

| | Transformation-% | | |
|---|---|---|---|
| | T | TB | B |
| pTi15955 | 26±8 | 55±9 | 19±6 |
| pTiC58 | ND | | |
| pRi2659 | ND | | |
| pRiA4 | ND | | |
| >831 | 41±3 | 52±5 | 7±2 |
| >829 | 17±2 | 68±5 | 15±4 |
| pSIM108 | 41±5 | 48±6 | 11±3 |
| pSIM843B | 34±4 | 53±6 | 13±2 |
| pSIM849 | 10±2 | 83±7 | 7±2 |
| pSIM781 | 11±1 | 58±3 | 31±2 |

FIGURE 5: "Transposon" jumps from non-integrating T-DNA into plant genome
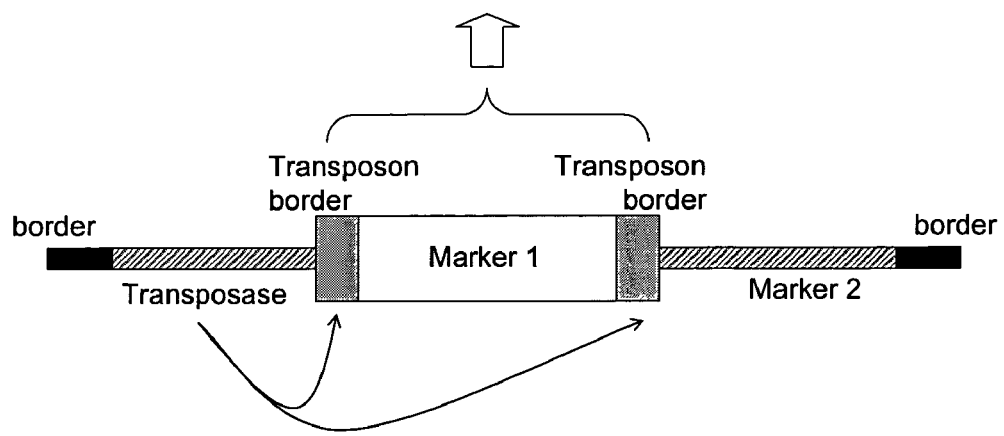
Transformation process:
(1) Infect explants
(2) T-DNA is transferred from Agro to plant cell nucleus
(3) Select for plant cells containing Marker 1 (transposon)
(4) Select against plant cells containing marker 2 (T-DNA)
(5) Regenerate plants only containing the transposon (SEQ ID 133 is in inverse complementary orientation in pSIM795)

PLANT-SPECIFIC GENETIC ELEMENTS AND TRANSFER CASSETTES FOR PLANT TRANSFORMATION

CROSS-REFERENCE TO RELATED PATENT APPLICATIONS

This application is a continuation-in-part of U.S. regular application Ser. No. 11/220,408, which claims priority to U.S. provisional application Ser. Nos. 60/607,586, filed on Sep. 8, 2004, 60/684,525, filed on May 26, 2005, and 60/698,938, filed on Jul. 14, 2005, which are all incorporated herein by reference.

FIELD OF THE INVENTION

Described herein are nucleic acid molecules and sequences, particularly those identified and obtained from plants, that are useful for transferring and integrating one polynucleotide into another via bacterial-mediated transformation.

BACKGROUND OF THE INVENTION

Bacterial-mediated transformation via, for example, *Agrobacterium* or *Rhizobium*, entails the transfer and integration of a polynucleotide from a bacterial plasmid into the genome of a eukaryotic organism. The region of DNA within the bacterial plasmid that is designated for such manipulation is called the transfer DNA ("T-DNA").

A T-DNA region is delimited by left and right "border" sequences, which are each about twenty-five nucleotides in length and oriented as imperfect direct repeats of the other. T-DNA transfer is initiated by an initial single stranded nick at the so-called right border site and is terminated by a subsequent secondary nick at the left border site. It is the resultant single-stranded linear DNA molecule that is transported, by the activity of other proteins, into the plant cell and ultimately integrated into the plant genome.

After initial cleavage at the right border, virD2 covalently binds to the 5'-side, and the DNA unwinds towards the left border where a second cleavage reaction occurs. The released single stranded DNA, traditionally referred to as the "T-strand," is coated with virE2 and processed for transfer via type IV type secretion (Lessl and Lanka, (1994) Cell 77: 321-324, 1994; Zupan and Zambryski, Plant Physiol 107: 1041-1047, 1997).

Since border sequences alone do not support a highly effective DNA transfer, extended border regions, generally comprising about 200 or more base pairs of *Agrobacterium* tumor-inducing (Ti) plasmid DNA, are used to transform plant cells. Two non-border sequences that are located within these extended border regions have been shown to promote DNA transfer, namely the 'overdrive' domain of pTi15955 (van Haaren et al., Nucleic Acids Res. 15: 8983-8997, 1987) and a DNA region containing at least five repeats of the 'enhancer' domain of pRiA4 (Hansen et al., Plant Mol. Biol., 20:113-122, 1992).

One issue associated with the use of conventional *Agrobacterium* border regions is the infidelity of DNA transfer. For instance, primary cleavage reactions at the right border are often not followed by secondary cleavage reactions at the left border. This "border skipping" leads to the transfer of T-DNAs that are still connected to the rest of the plasmid. Such plasmid backbone transfer is undesirable because these sequences typically comprise antibiotic resistance genes. Plasmid backbone transfer can also be a consequence of inadvertent right border activity at the left border.

A second issue concerns the use of conventional and poorly characterized *Agrobacterium* border regions, which permit only very little optimization of transfer frequencies. This leads to poor transformation rates, and high input costs for the production of large numbers of transformed plants.

Furthermore, the presence of foreign T-DNA sequences in food crops is often perceived as undesirable, and the application of genetic engineering has therefore been limited to a small number of crops that are destined for feed, oil, fibers, and processed ingredients. Public concerns were addressed through development of an all-native approach to making genetically engineered plants, as disclosed by Rommens et al. in WO2003/069980, US-2003-0221213, US-2004-0107455, and WO2005/004585, which are all incorporated herein by reference. Rommens et al. teach the identification and isolation of genetic elements from plants that can be used for bacterium-mediated plant transformation. Thus, Rommens teaches that a plant-derived transfer-DNA ("P-DNA"), for instance, can be isolated from a plant genome and used in place of an *Agrobacterium* T-DNA to genetically engineer plants.

The concept of P-DNA mediated transformation has previously been demonstrated in potato. A 400-base pair potato P-DNA delineated by regions that share sequence identity with the left border of nopaline strains and the right border of octopine strains was effectively transferred from *Agrobacterium* to plant cells (Rommens et al., Plant Physiol 135: 421-431, 2004).

The potato P-DNA was subsequently used to introduce a silencing construct for a tuber-specific polyphenol oxidase (PPO) gene into potato. Resulting intragenic plants displayed tolerance against black spot bruise sensitivity in impacted tubers.

The present invention provides new plant-specific DNA elements that replace bacterial borders, and are particularly useful for all-native DNA transformation methods.

The present invention also reveals the organization of the extended regions that are involved in the initiation of DNA transfer by mediating primary DNA cleavage, and describes the sequence requirements and spacing of genetic elements that support high activity of the described elements. Furthermore, the invention shows how manipulations of regions that surround enzyme cleavage sites can enhance the fidelity of DNA transfer.

SUMMARY OF THE INVENTION

One aspect of the present invention is a plant transformation cassette, comprising a first polynucleotide positioned between a second and third polynucleotide, wherein (i) both the second and third mediate single-stranded or double-stranded DNA cleavage, which can either be sequence specific or non-specific, and either (ii) at least one of the second and third polynucleotide is not identical in nucleotide sequence to an *Agrobacterium* transfer-DNA border sequence or to a plant-derived transfer DNA border sequence. Non-specific DNA cleavage means that there is not any one site-specific cleavage sequence. For instance, with respect to an OriT sequence, the OriT mediates cleavage of the DNA at various positions and not necessarily at a precise site within the actual OriT sequence.

In one embodiment, (a) the second polynucleotide is selected from the group consisting of (i) a right border sequence of an *Agrobacterium* T-DNA, (ii) a plant-derived border sequence, and (iii) a homoendonuclease recognition site, and (b) the third polynucleotide is selected from the group consisting of (i) a left border sequence of an *Agrobacterium* T-DNA, (ii) a plant-derived border sequence, (iii) a homoendonuclease recognition site, and (iv) an origin of conjugative plasmid DNA transfer.

In another embodiment, the third polynucleotide is an origin of conjugative plasmid DNA transfer. In one embodiment, the origin of conjugative plasmid DNA transfer is an origin of transfer selected from the group consisting of, but not limited to, *Agrobacterium, Rhizobium, Corynebacterium, Escherichia,* or *Klebsiella*.

In another embodiment, the third polynucleotide is an origin of conjugative plasmid DNA transfer and the second polynucleotide is an *Agrobacterium* Right Border, a plant-derived Border alternative, or a homoendonuclease recognition site.

In another embodiment, the origin of conjugative plasmid DNA transfer comprises a sequence with at least 70% identity to at least a fragment of the sequence depicted in SEQ ID NO: 219, and which is a functional origin of transfer.

In one embodiment, the cassette further comprises a fourth polynucleotide, wherein the fourth polynucleotide (i) is positioned between the second and third polynucleotide, (ii) mediates single-stranded or double-stranded DNA cleavage, and (iii) is not identical in nucleotide sequence to an *Agrobacterium* transfer-DNA border sequence or to a plant-derived transfer DNA border sequence.

In one embodiment, the fourth polynucleotide is an origin of conjugative DNA transfer.

In another embodiment, the first polynucleotide is positioned between two origins of conjugative DNA transfer.

Another aspect of the present invention is a plasmid, which comprises any one of the cassettes described herein. In one embodiment, the plasmid comprises in its backbone one or more of an expression cassette for (i) a cytokinin gene or (ii) a homoendonuclease gene.

In another embodiment, the plant transformation cassette comprises at least one recognition site for a homoendonuclease. In one embodiment, the recognition site is a recognition site for an I-CeuI or I-TevI homoendonuclease enzyme.

In another embodiment, the plasmid backbone comprises at least one expression cassette for a homoendonuclease gene. In one embodiment, the homoendonuclease gene is selected from the group consisting of the I-CeuI gene or a I-TevI gene.

In another embodiment, the homoendonuclease gene is modified to reduce bacterial toxicity and/or enhance single-stranded DNA nicking rather than double-stranded DNA cleavage. An example of such a modification leads to the substitution of threonine at position 122 to alanine in I-TevI.

Another aspect of the present invention is a method for transforming a plant cell, comprising contacting a plant cell with a bacterial strain containing any one of the plasmids described herein. In one embodiment, the bacterial strain is a strain selected from the group consisting of *Agrobacterium tumefaciens, Agrobacterium rhizogenes, Rhizobium trifolii, Rhizobium leguminosarum, Phyllobacterium myrsinacearum, SinoRhizobium meliloti,* and *MesoRhizobium loti*.

Another aspect of the present invention is a transposable element cassette that comprises a first polynucleotide, which comprises a non-autonomous transposable element, positioned between a second and third polynucleotide, wherein the second and third polynucleotides each mediate single-stranded or double-stranded DNA cleavage. In one embodiment, the ends of the non-autonomous transposable element share at least 70% sequence identity with the ends of a known transposable element that are required for its transposition, whereby the known transposable element is selected from a group that includes, but is not limited to, the maize Ac element, the maize Ds1 element, the maize En/Spm element, the common morning glory Tip100 element, the pearl millet PacI element, and the *Arabidopsis* Tag1 element. In another embodiment, the sequence of the transposable element comprises a sequence with at least 70% identity to the sequence depicted in SEQ ID NO: 138. In one embodiment, the cassette further comprises a transposase gene that (i) is operably linked to regulatory elements so that it can be expressed and (ii) encodes a protein that can excise the non-autonomous transposable element.

One other aspect of the present invention is a transposable element cassette together with a cassette for a transposase source, wherein the transposable element cassette comprises (1) a non-autonomous transposable element flanked by sequences that mediate single-stranded or double-stranded DNA cleavage, and wherein the cassette for the transposase source comprises (i) a first polynucleotide positioned between (ii) a second polynucleotide and (iii) third polynucleotide, wherein (a) both the second and third polynucleotide each mediate single-stranded or double-stranded DNA cleavage and are selected from the group consisting of an *Agrobacterium* border sequence, a plant-derived border sequence, an endonuclease recognition site sequence, and an origin of DNA transfer sequence, and (b) the first polynucleotide comprises a transposase gene that (i) is operably linked to regulatory elements so that it can be expressed and (ii) encodes a protein that mediates excision of the non-autonomous transposable element from any one of the transposable element cassettes described herein. In one embodiment, the non-autonomous transposable element further comprises a selectable marker gene. In another embodiment, the selectable marker gene is the neomycin phosphotransferase gene. Other common selectable marker genes appropriate for plant transformation can be used. In a further embodiment, the ends of the non-autonomous transposable element are at least 70% identical to the ends of the maize Ac element.

In one embodiment, the transposable element cassette further comprises (1) a right border sequence, a plant-derived border sequence, or an endonuclease recognition site sequence, (2) a non-autonomous transposable element comprising (a) a desired polynucleotide, and (b) a selectable marker gene, and (3) a left border sequence, or a plant-derived border sequence or an origin of conjugative DNA transfer sequence.

In another embodiment, the transposable element cassette further comprises (1) a right border sequence, a plant-derived border sequence, or an endonuclease recognition site sequence, (2) a non-autonomous transposable element inserted between a promoter and a selectable marker gene, and (3) a left border sequence, or a plant-derived border sequence or an origin of conjugative DNA transfer sequence. In one embodiment, the transposable element comprises a visual or selectable marker gene.

Another aspect of the present invention is a method for transforming a plant cell with a non-autonomous transposable element, comprising contacting a plant cell with a bacterial strain containing a plasmid that contains a transposable element cassette, wherein the bacterial strain is a strain selected from the group consisting of *Agrobacterium tumefaciens, Agrobacterium rhizogenes, Rhizobium trifolii, Rhizobium leguminosarum, Phyllobacterium myrsinacearum, SinoRhizobium meliloti,* and *MesoRhizobium loti*, and wherein the transformed plant cell that not contain any sequences from the cassette other than the transposable element.

Another aspect of the present invention is a method for transforming a plant cell with a non-autonomous transposable element, comprising contacting a plant cell with either (i) one bacterial strain containing a first cassette and a second cassette, or (ii) two bacterial strains containing a first cassette and a second cassette, wherein the bacterial strain(s) is/are selected from the group consisting of *Agrobacterium tumefaciens*, *Agrobacterium rhizogenes*, *Rhizobium trifolii*, *Rhizobium leguminosarum*, *Phyllobacterium myrsinacearum*, *SinoRhizobium meliloti*, and *MesoRhizobium loti*, and wherein the transformed plant cell that not contain any sequences from the cassette other than the transposable element.

In one embodiment, the first cassette comprises a first polynucleotide, which comprises a non-autonomous transposable element, positioned between a second and third polynucleotide, wherein the second and third polynucleotides serve as sites for single-stranded or double-stranded DNA cleavage.

In one embodiment, the second cassette comprises (i) a first polynucleotide positioned between (ii) a second polynucleotide and (iii) third polynucleotide, wherein (a) both the second and third polynucleotide serve as sites for single-stranded or double-stranded DNA cleavage and are selected from the group consisting of an *Agrobacterium* border sequence, a plant-derived border sequence, an endonuclease recognition site sequence, and an origin of DNA transfer sequence, and (b) the first polynucleotide comprises a transposase gene that (i) is operably linked to regulatory elements so that it can be expressed and (ii) encodes a protein that mediates excision of the non-autonomous transposable element from the first cassette.

One aspect of the present invention is a DNA sequence, comprising a polynucleotide sequences, designated as a "cleavage sites", that comprise the consensus sequence depicted in SEQ ID NO: 84 and which are not identical to an *Agrobacterium* transfer-DNA border sequence, nor to a previously isolated border or border-like sequence.

In one embodiment, a cleavage site is selected from the group consisting of SEQ ID NOs: 8, 9, 11-13, 15-17, 28-37, 38-51, 85-86, 189, 190, 194-196, and 198. In one embodiment, the cleavage site represents a synthetic sequence, and is selected from the group consisting of SEQ ID NOs: 8, 9 and 11-13. The present invention contemplates a transformation cassette that comprises two cleavage sites. One of those sites may be termed the "primary cleavage site," while the other may be a "secondary cleavage site." See FIG. 4.

In another embodiment, the cleavage site is generated by substituting at least one nucleotide of a cleavage site or cleavage site-like sequence selected from the group consisting of SEQ ID NOs: 8, 9, 11-13, 15-17, 28-86, 190, and 193-198.

In another embodiment, the cleavage site represents a contiguous sequence of a plant genome, and is selected from the group consisting of SEQ ID NOs: 15-17, 28-37, 38-50, and 85-86.

In yet another embodiment, the cleavage site is derived from a variant of a sequence selected from the group consisting of SEQ ID NOs: 8, 9, 11-13, 15-17, 28-37, 38-51, 85-86, 189, 190, 194-196. That is, a variant of any one of these particular sequences is encompassed by the present invention so long as the variant sequence permits cleavage by a pertinent transformation enzyme and/or enzyme complex involved in bacterium-mediated transformation. Hence, a variant sequence may share about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, or about 50%, or about less than 50% sequence identity with of any one of SEQ ID NOs: 8, 9, 11-13, 15-17, 28-37, 38-51, 85-86, 189, 190,194-196, so long as the variant sequence can still be cleaved according to the present invention.

Another aspect of the present invention is a transfer cassette, comprising such a cleavage site positioned upstream from a desired polynucleotide.

In one embodiment, the cleavage site in the transfer cassette is selected from the group consisting of SEQ ID NOs: 8, 9, 11-13, 15-17, 28-37, 38-50, 85-86, 189, 190, and 194-196.

In one embodiment, the transfer cassette comprises two cleavage sites defined by a first polynucleotide and a second polynucleotide, whereby the first polynucleotide may comprise a sequence for an "initial cleavage site" that is positioned upstream from the desired polynucleotide. The second polynucleotide may comprise a sequence for a "final cleavage site" that is positioned downstream from the desired polynucleotide. The two cleavage sites may be positioned as perfect or imperfect direct repeats.

The transfer cassette may further comprise a nucleotide sequence downstream from the initial cleavage site, whereby this "DI region" is a DNA sequence that (a) comprises at least about 30 base pairs immediately downstream from the initial cleavage site, (b) comprises a sequence that shares at least 70% sequence identity with the DR domain depicted in SEQ ID NO: 107, that is positioned within about 60 base pairs from the initial cleavage site, (c) optionally contains multiple sequences that are identical or inverse complementary to SEQ ID NO: 115, (d) is not identical to a region that flanks a T-DNA right border in *Agrobacterium* Ti or Ri plasmids, and (e) supports cleavage activity. The DI region may enhance the initial cleavage activity by at least 25% compared to the corresponding sequence of the Ti or Ri plasmid, which does not comprise the same DI region.

In one embodiment the DI region may share at least 70% sequence identity with SEQ ID NO: 22, 108-114.

In one embodiment, the transfer cassette further comprises a nucleotide sequence upstream from the final cleavage site, whereby this "UF region" is a DNA sequence that (a) comprises at least 40 base pairs immediately upstream from the final cleavage site, (b) comprises at least 55% adenine or thymine residues (AT-rich), (c) comprises a sequence that has at least 70% sequence identity to either the UL domain depicted in SEQ ID NO: 120 or the inverse complement of SEQ ID NO: 120 within a distance of about 50 base pairs from the final cleavage site, (d) optionally comprises a putative binding site for integration host factor that has at least 70% sequence identity to the consensus sequence [A/T]-AT-CAANNNNTT-[A/G] (SEQ ID NO: 129) or has at least 70% sequence identity to the inverse complement of SEQ ID NO: 129, and that is positioned within 200 base pairs from the final cleavage site or left border, (e) is not identical to a region that flanks a T-DNA border in *Agrobacterium* Ti or Ri plasmids, and (f) supports initial cleavage site activity. In one embodiment, the UF region enables transformation frequencies that are increased, such as by at least 25%, compared to the corresponding sequence of a Ti or Ri plasmid.

In one embodiment, the UF region may share at least 70% sequence identity to the sequences depicted in SEQ ID NO: 184-186 and 211-214.

In another embodiment, the transfer cassette further comprises both a DI and UF element.

Another aspect of the present invention is a transformation vector comprising any one of such transfer cassettes, wherein the region of the plasmid backbone that is "upstream from the initial cleavage" (UI region) comprises at least a 48-nucleotide sequence that contains adenine-rich trinucleotides interspaced by nucleotides that represent, in at least six cases, a cytosine or thymine (pyrimidine) residue, whereby the most downstream pyrimidine represents either the first base of the initial cleavage site or the base at position −4 relative to the initial cleavage site. The UI region is not identical to a region that flanks a T-DNA border of an *Agrobacterium* or binary plasmid. The UI region supports initial cleavage activity and may enable transformation frequencies that are increased, such as by at least 25%, compared to the corresponding sequence of a Ti or Ri plasmid.

In one embodiment, the UI region of the transformation vector comprises a nucleotide sequence that has greater than 70% sequence identity to the sequence depicted in SEQ ID NOs: 199-208.

In another embodiment, the region of the plasmid backbone that is associated with the final cleavage site (AF region) is a DNA sequence that (a) comprises at least part of the final cleavage site or left border and at about two to 40 base pairs flanking downstream DNA, (b) comprises at least four tightly linked clusters of two or more cytosine bases separated by 1-11 other nucleotides, CCN1-11CCN1-11CCN1-11CC (SEQ ID NO: 122), (c) is not identical to a region that flanks a T-DNA border in *Agrobacterium* Ti or Ri plasmids, and (d) supports initial cleavage activity. In one embodiment, the AF region enables transformation frequencies that are, for example, at least 25% compared to the corresponding sequence of a Ti or Ri plasmid.

In one embodiment, the AF region of the transformation vector comprises a nucleotide sequence that has greater than 70% sequence identity to the sequence depicted in SEQ ID NOs: 187, 188, and 215-218.

The present invention is not limited to the percentage by which initial or final cleavage activity is enhanced by any particular transformation element described herein. For instance, any of the transformation elements described herein may enhance the initial or final cleavage activity by 100% or more than 100%, or about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 15%, or about 5% or at least about 1%, compared to a control that does not comprise the desired transformation element.

The present invention also contemplates transformation cassettes and plasmids, whereby not every transformation element in the construct enhances cleavage activity. Thus, not every element in a cassette described herein must enhance cleavage activity or transformation efficiency in order for it to be useful.

In another aspect of the present invention, a transformation vector is provided, which comprises (A) a transfer cassette, which comprises, from 5' to 3', (i) an initial cleavage site, (ii) a DI region, (iii) a UF region, and (iv) a final cleavage site, and (B) in the transformation plasmid backbone, at least one of (i) a UI region, and (ii) a AF region.

In one aspect, the relevant sequences for DNA transfer of such a transformation vector are shown in SEQ ID NO: 131 and 132.

In one embodiment, the transformation vector further comprises a desired polynucleotide positioned between DI and UF region.

In another embodiment, the transformation vector contains at least one *Agrobacterium* border as alternative to a cleavage site.

In one embodiment, a putative cleavage site is identified by screening DNA databases using programs such as BLASTN or a similar program and search motifs such as depicted in SEQ ID NO: 130.

In another embodiment, a putative cleavage site is isolated by applying PCR-based methods described in the Examples.

In yet another embodiment, a DI region or UF region is identified by screening DNA databases with programs such as BLASTN (Altschul et al., Nucleic Acids Res. 25: 3389-3402, 1997) using desired domains as queries.

In one embodiment, a method of identifying a functionally active cleavage site is provided comprising the steps: (a) identifying a putative cleavage site, (b) annealing two primers in such a way that a double strand DNA sequence is generated comprising the putative cleavage site, optionally flanked by the sticky ends of specific restriction enzyme sites, (c) ligating this DNA fragment with a linearized plasmid that contains replication origins for both *E. coli* and *Agrobacterium*, (d) introducing the new plasmid into *Agrobacterium*, (e) infecting explants of a plant that is amenable to *Agrobacterium*-mediated transformation with the resulting *Agrobacterium* strain, (f) applying tissue culture methods for transformation, proliferation, and, if necessary, regeneration (g) allowing callus and/or shoot formation, (h) counting the average number of calli and/or shoots per explant, and comparing the resulting frequencies with those of conventional controls, (i) selecting putative cleavage sites that support transformation.

In one embodiment, the putative cleavage site may be found to enhance the transformation efficiency in comparison to an identical plasmid, which does not contain the putative cleavage site. For instance, a putative cleavage site may enhance the transformation efficiency by about 100% or more than 100%, or about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 15%, or about 5% or at least about 1%, compared to a control that does not comprise the putative cleavage site.

In one embodiment, a method of identifying a functionally active DI or UF region is provided comprising the steps; (a) identifying a putative DNA region, (b) isolating the region from plant DNA using methods such as PCR, (c) using this region to replace the functional region of a transformation vector, (d) introducing the modified plasmid into *Agrobacterium*, (e) infecting explants of a plant that is amenable to *Agrobacterium*-mediated transformation with the resulting *Agrobacterium* strain, (f) applying tissue culture methods for transformation and proliferation, (g) allowing callus formation, (h) counting the average number of calli per explant, and comparing the resulting frequencies to those obtained with a conventional control plasmid that does not comprise the putative DNA region, and (i) identifying a DNA region that supports transformation.

In one embodiment, a putative DNA region may be found to enhance the transformation efficiency in comparison to an identical plasmid, which does not contain the putative DNA region. For instance, a putative DNA region may enhance the transformation efficiency by about 100% or more than 100%, or about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 15%, or about 5% or at least about 1%, compared to a control that does not comprise the putative DNA region.

In one embodiment, the step of identifying the putative DNA region may be accomplished by hybridization studies, where a random or degenerate nucleic acid probe or oligonucleotide is used to identify sequences from a genome that can be subsequently tested for transformation efficacy. For instance, such a probe may be employed in a Southern blot of genomic DNA isolated from a plant, where the probe is essentially based on one of the transformation elements described herein, e.g., a UF region of the present invention.

Alternatively, a preparation of DNA may be subjected to PCR using primers that are specific to a particular transformation element described herein. On the other hand, the primers may be random primers or degenerate primers based on a desired transformation element, that are employed in a PCR reaction of DNA. The subsequently amplified PCR product(s) can be isolated by standard procedures, e.g., via excising it from an electrophoretic gel, and then tested according to the present invention for transformation efficacy.

In one embodiment, at least one, if not all, of the nucleotide sequences of the transfer cassette are endogenous to a plant. That is, in one embodiment, at least one, if not all, of the nucleotide sequences in the transfer cassette are native to a plant, or are isolated from the same plant, the same plant species, or from plants that are sexually interfertile with the plant to be transformed. In one embodiment, the plant is a monocotyledonous plant and selected from the group consisting of wheat, turf grass, maize, rice, oat, wheat, barley, sorghum, orchid, iris, lily, onion, banana, sugarcane, and palm.

In another embodiment, the plant is a dicotyledonous plant and selected from the group consisting of potato, tobacco, tomato, avocado, pepper, sugarbeet, broccoli, cassava, sweet potato, cotton, poinsettia, legumes, alfalfa, soybean, pea, bean, cucumber, grape, *brassica*, carrot, strawberry, lettuce, oak, maple, walnut, rose, mint, squash, daisy, and cactus.

Another aspect of the present invention is a method for transforming a plant cell, comprising introducing a transformation vector, which comprises any one of the transfer cassettes described herein, into a plant cell.

In one embodiment, the plant cell is located in a plant. In another embodiment, the plant is selected from the group consisting of wheat, turf grass, maize, rice, oat, wheat, barley, sorghum, orchid, iris, lily, onion, banana, sugarcane, palm, potato, tobacco, tomato, avocado, pepper, sugarbeet, broccoli, cassava, sweet potato, cotton, poinsettia, legumes, alfalfa, soybean, carrot, strawberry, lettuce, oak, maple, walnut, rose, mint, squash, daisy, and cactus.

In another embodiment, the transformation plasmid is introduced into the plant cell via a bacterium. In one embodiment, the bacterium is from *Agrobacterium, Rhizobium*, or *Phyllobacterium*. In a further embodiment, the bacterium is selected from the group consisting of *Agrobacterium tumefaciens, Rhizobium trifolii, Rhizobium leguminosarum, Phyllobacterium myrsinacearum, SinoRhizobium meliloti*, and *MesoRhizobium loti*.

In a preferred embodiment, at least one, if not all, of the nucleotide sequences in the transfer cassette are isolated from the same plant, the same plant species, or plants that are sexually interfertile. In one embodiment all of the nucleotide sequences are isolated from the same plant, the same plant species, or from plants that are sexually interfertile.

In one embodiment, a cassette is provided, which comprises (1) a first polynucleotide, comprising a sequence that is (i) nicked when exposed to an enzyme involved in bacterial-mediated plant transformation and (ii) not identical to a bacterial border sequence; (2) a second polynucleotide, which may be (i) an imperfect or perfect repeat of the first polynucleotide, or (ii) a bacterial T-DNA border; (3) a desired polynucleotide; and (4) at least one of (a) UI region, (b) DI region, (c) UF region, and (d) AF region.

In one embodiment, the first polynucleotide comprises a sequence that is native to a plant genome. In another embodiment, the first polynucleotide consists essentially of a sequence that is native to a plant genome.

In a preferred embodiment, the first polynucleotide is targeted by a vir gene-encoded protein. In one embodiment, the vir gene-encoded protein is VirD2.

In another embodiment, the first polynucleotide conforms to the consensus sequence depicted in SEQ ID NO: 84. In a preferred embodiment, the first polynucleotide comprises a sequence depicted in any one of the group consisting of SEQ ID NOs: 8, 9, 11-13, 15-17, 28-37, 38-51, 85-86, 189, 190, 194-196, and 198.

In another embodiment, the first polynucleotide comprises a sequence with at least 70% sequence identity to the sequence of any one of SEQ ID NO: 28, 85, or 86. In a further embodiment, the first polynucleotide comprises a sequence that shares at least 70% sequence identity with a sequence depicted in any one of SEQ ID NOs: 28-30.

In one embodiment, the first polynucleotide comprises a sequence that shares at least 70% sequence identity with the sequence depicted in SEQ ID NO: 32.

In one embodiment, the first polynucleotide comprises a sequence that shares at least 70% sequence identity with the sequence depicted in SEQ ID NO: 33.

In one embodiment, the first polynucleotide comprises a sequence that shares at least 70% sequence identity with the sequence depicted in any one of SEQ ID NOs: 34-36.

In one embodiment, the first polynucleotide comprises a sequence that shares at least 70% sequence identity with the sequence depicted in SEQ ID NO: 37.

In one embodiment, the first polynucleotide comprises a sequence that shares at least 70% sequence identity with the sequence depicted in any one of SEQ ID NOs: 195-196.

In one embodiment, the first polynucleotide comprises a sequence that shares at least 70% sequence identity with the sequence depicted in any one of SEQ ID NOs: 51 and 194.

In one embodiment, the first polynucleotide comprises a sequence that shares at least 70% sequence identity with the sequence depicted in any one of SEQ ID NOs: 189-190.

In one embodiment, the first polynucleotide comprises 1, 2, 3, 4, 5, 6, 7, 8, 9, or 10 or more nucleotides that are different in comparison to an *Agrobacterium* T-DNA border sequence.

In one embodiment, the first polynucleotide is greater than 70% identical in sequence to an *Agrobacterium* T-DNA border sequence.

In another embodiment, the UI region comprises a sequence that shares at least 70% sequence identity with at least one of SEQ ID NOs: 199-208.

In another embodiment, the DI region element comprises a sequence that that shares at least 70% sequence identity with at least one of SEQ ID NOs: 22, 108-114.

In another embodiment, the UF region element comprises a sequence that that shares at least 70% sequence identity with at least part of at least one of SEQ ID NOs: 184-186 and 211-214. In another embodiment, the AF region comprises a sequence that shares at least 70% sequence identity with at least one of SEQ ID NOs: 187, 188, or 215-218.

The present invention encompasses variant sequences of the transformation elements described herein and is not limited to the percentage sequence identity that any particular transformation element may share with any particular sequence described herein. Thus, the present invention encompasses sequences for any of the transformation elements described herein, e.g., a UI region, DI region, UF region, or AF region, that shares about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 15%, or about 5% or at least about 1% sequence identity with a corresponding sequence identified herein.

Another aspect of the present invention contemplates transformation elements such as a UI region, DI region, UF region, or AF region, that does not comprise a nucleotide sequence that is identical to a corresponding region from a bacterium plasmid, such as from a tumor-inducing plasmid from *Agrobacterium* or *Rhizobium*.

In another embodiment, the AF region element comprises at least 70% sequence identity with at least part of at least one of SEQ ID NO: 187, 188, and 215-218.

In another embodiment, the desired polynucleotide is positioned between the first and second polynucleotides, and wherein the desired polynucleotide is located downstream from a first polynucleotide cleavage site that functions in initial cleavage.

In a preferred embodiment, the cassette comprises a UI region positioned upstream from the first polynucleotide cleavage site and a AF region that is downstream from the second polynucleotide cleavage site.

In one particular embodiment, the portion of the cassette that comprises the UI and DI regions comprise the sequence depicted in SEQ ID NO: 131. In one embodiment, the portion of the cassette that comprises the UF and AF regions comprises the sequence depicted in SEQ ID NO: 132.

In one preferred embodiment, all of the DNA sequences between the first and second polynucleotides are plant DNA. In this regard, the plant DNA is endogenous to (1) a monocotyledonous plant selected from the group consisting of wheat, turf grass, maize, rice, oat, wheat, barley, sorghum, orchid, iris, lily, onion, banana, sugarcane, and palm; or (2) a dicotyledonous plant selected from the group consisting of potato, tobacco, tomato, avocado, pepper, sugarbeet, broccoli, cassava, sweet potato, cotton, poinsettia, legumes, alfalfa, soybean, carrot, strawberry, lettuce, oak, maple, walnut, rose, mint, squash, daisy, and cactus, cucumber, melon, canola, apple, or pine.

In another embodiment, the cassette further comprises at least one of (1) an overdrive element, comprising a sequence that is at least 70% identical in sequence to SEQ ID NO: 88; (2) a pyrimidine-rich element, comprising a sequence that shares at least 70% sequence identity with any one of SEQ ID NOs: 199-208 but which is not identical to an *Agrobacterium* plasmid sequence that flanks a right border; (2) an AT-rich element, comprising a sequence that shares at least 70% sequence identity to at least part of any one of SEQ ID NOs: 184-186 and 211-214; and (4) a cytosine cluster, comprising a sequence at least 70% sequence identity to at least part of any one of SEQ ID NOs: 187-188 and 215-218.

The present invention also provides a plant transformation cassette, which comprises at least one of (1) a polynucleotide comprising a sequence depicted in any one of the group consisting of SEQ ID NOs: 8, 9, 11-13, 15-17, 28-50, 85, 86, and 190 or any other cleavage site sequence disclosed herein, wherein the 3'-end of the polynucleotide abuts a cytosine cluster, e.g., wherein the sequence comprising the 3'-end of the polynucleotide and DNA downstream thereof, comprises the sequence depicted in SEQ ID NO: 122; and (2) a polynucleotide comprising a sequence depicted in any one of the group consisting of SEQ ID NOs: 8, 9, 11-13, 15-17, 28-50, 85, and 86 or any other cleavage site disclosed herein, wherein the 5'-end of the polynucleotide abuts a UI region.

In one embodiment, the cytosine cluster comprises a sequence that shares at least 70% sequence identity with any one of the sequences in SEQ ID NOs: 187-188.

In another embodiment, the UI region comprises a sequence that shares at least 70% sequence identity with any one of the sequences in SEQ ID NOs: 199, 209, and 210.

In another embodiment, a plant transformation cassette is provided, which comprises at least one of (1) a polynucleotide comprising a sequence depicted in any one of the group consisting of SEQ ID NOs: 8, 9, 11-13, 15-17, 28-50, 85, 86, and 190, wherein the 3'-end of the polynucleotide abuts a cytosine cluster; (2) a polynucleotide comprising (i) a sequence depicted in any one of the group consisting of SEQ ID NOs: 8, 9, 11-13, 15-17, 28-37, 38-51, 85-86, 189, 194-196, and 198, and (ii) a DNA sequence positioned downstream of the sequence of (i), wherein the sequences of (i) and (ii) together comprise a cytosine cluster; and (3) a polynucleotide comprising a sequence depicted in any one of the group consisting of SEQ ID NOs: 8, 9, 11-13, 15-17, 28-37, 38-51, 85-86, 189, 194-196, and 198, wherein the 5'-end of the polynucleotide abuts a pyrimidine-rich element. In one embodiment, the cytosine cluster comprises a sequence that shares at least 70% sequence identity with any one of the sequences in SEQ ID NOs: 187-188. In another embodiment, the pyrimidine-rich element comprises a sequence that shares at least 70% sequence identity with any one of the sequences in SEQ ID NOs: 21 and 199-208.

Another aspect of the present invention is a method for transforming a plant cell, which comprises introducing any one of the cassettes or plant transformation cassettes described herein into a plant cell. Such a cassette may be positioned within a plant transformation plasmid, such as a Ti- or Ri-plasmid.

Thus, in one particular embodiment, a cassette of the present invention is placed in a vector, which is derived from a tumor-inducing cassette from an *Agrobacterium*, *Rhizobium*, or *Phyllobacterium* bacterium, and which is suitable for plant transformation.

In one embodiment, the bacterium is selected from the group consisting of *Agrobacterium tumefaciens*, *Rhizobium trifolii*, *Rhizobium leguminosarum*, *Phyllobacterium myrsinacearum*, *SinoRhizobium meliloti*, and *MesoRhizobium loti*.

In another embodiment of this method, the vector housing the desired cassette is maintained in a strain of one of these bacteria and it is the bacterium strain that is used to infect the plant cell and thereby introduce the cassette or plant transformation cassette into the plant cell.

In one embodiment, the plant cell is located in either (1) a monocotyledonous plant or explant thereof selected from the group consisting of wheat, turf grass, maize, rice, oat, wheat, barley, sorghum, orchid, iris, lily, onion, banana, sugarcane, and palm; or (2) a dicotyledonous plant or explant thereof selected from the group consisting of potato, tobacco, tomato, avocado, pepper, sugarbeet, broccoli, cassava, sweet potato, cotton, poinsettia, legumes, alfalfa, soybean, carrot, strawberry, lettuce, oak, maple, walnut, rose, mint, squash, daisy, and cactus.

In one particular embodiment, a tomato plant is transformed using a cassette in which the first polynucleotide in the cassette comprises a sequence that shares at least 70% sequence identity with any one of the sequences of SEQ ID NO: 28-30.

In another embodiment, an alfalfa plant is transformed using a cassette in which the first polynucleotide comprises a sequence that shares at least 70% sequence identity to the sequence depicted in SEQ ID NO: 32.

In another embodiment, a barley plant is transformed using a cassette in which the first polynucleotide comprises a sequence that shares at least 70% sequence identity to the sequence depicted in SEQ ID NO: 33.

In another embodiment, a rice plant is transformed using a cassette in which the first polynucleotide comprises a sequence that shares at least 70% sequence identity to the sequence depicted in SEQ ID NOs: 34-36.

In another embodiment, a wheat plant is transformed using a cassette in which the first polynucleotide comprises a sequence that shares at least 70% sequence identity to the sequence depicted in SEQ ID NO: 37.

In another embodiment, a soybean plant is transformed using a cassette in which the first polynucleotide comprises a sequence that shares at least 70% sequence identity to the sequence depicted in any one of SEQ ID NOs: 195-196.

In another embodiment, a maize plant is transformed using a cassette in which the first polynucleotide comprises a sequence that shares at least 70% sequence identity to the sequence depicted in any one SEQ ID NOs: 51 and 194.

In another embodiment, a *Brassica* plant is transformed using a cassette in which the first polynucleotide comprises a sequence that shares at least 70% sequence identity to one of the sequences depicted in SEQ ID NOs: 189 or 198. In one embodiment, the plant to be transformed is a *Brassica* plant.

The present invention does not limit which polynucleotide sequence can be used to transform a particular plant. Thus, a first polynucleotide that comprises a sequence that shares at least 70% sequence identity to the sequence depicted in any one of SEQ ID NOs: 51 and 194, can be used to transform a potato plant, instead of maize. Hence, the present invention contemplates various permutations of transformation elements and their usefulness in transforming a variety of plants and organisms. According to the present invention, an animal cell may be transformed using any of the cassettes or plasmids described herein. Hence, in one embodiment, an animal cell may be transformed with genetic elements that are native to the animal and its species, thereby providing an "all-native" approach to transforming animal cells and animals.

In one particular embodiment, the monocotyledonous or dicotyledonous explant is a seed, germinating seedling, leaf, root, stem, cutting, or bud.

According to these methods, the bacterium that is used to perform the plant transformation can be an *Agrobacterium*, *Rhizobium*, or *Phyllobacterium* bacterium. In one embodiment, the bacterium is selected from the group consisting of *Agrobacterium tumefaciens*, *Rhizobium trifolii*, *Rhizobium leguminosarum*, *Phyllobacterium myrsinacearum*, *SinoRhizobium meliloti*, and *MesoRhizobium loti*.

In one embodiment, the bacterial T-DNA border of the cassette described herein is from *Agrobacterium tumefaciens*, *Rhizobium trifolii*, *Rhizobium leguminosarum*, *Phyllobacterium myrsinacearum*, *SinoRhizobium meliloti*, or *MesoRhizobium loti*.

Another aspect of the present invention is a cassette, which comprises (1) a first polynucleotide, comprising a sequence that is nicked when exposed to an enzyme involved in bacterial-mediated plant transformation and; (2) a second polynucleotide that has greater than 70% sequence identity to any one of SEQ ID NOs: 133-137. In one embodiment, the cassette further comprises a desired polynucleotide. In another embodiment the first polynucleotide is a bacterial T-DNA right border sequence. In another embodiment, the first polynucleotide is not identical in sequence to a bacterial T-DNA right border sequence. The sequence of the first polynucleotide may comprise the sequence depicted in any one of SEQ ID NOs: 8, 9, 11-13, 15-17, 28-50, 85, 86, 189, 190, and 194-196.

In another aspect, a transposase-transposon, plant transformation cassette is provided, which comprises (i) left and right transfer-DNA border sequences; (ii) a non-autonomous transposable element; and (iii) a transposase gene, wherein the non-autonomous transposable element and the transposase gene are positioned between the left and right border sequences.

In one embodiment, the plant transformation cassette comprises at least one of the border sequences comprising a sequence that is (i) nicked when exposed to an enzyme involved in bacterial-mediated plant transformation and (ii) is not identical to a bacterial border sequence. The sequence of the first polynucleotide may comprise the sequence depicted in any one of SEQ ID NOs: 8, 9, 11-13, 15-17, 28-50, 85, 86, 189, 190, and 194-196.

In one embodiment, in this cassette, at least one of the border sequences is a bacterial T-DNA border. In another embodiment, the cassette further comprises a desired polynucleotide positioned within the non-autonomous transposable element.

In one embodiment, the terminal ends of the non-autonomous transposable element are those from maize transposable element Ac.

In a further embodiment, the desired polynucleotide is positioned at least 80-200 nucleotides from either terminal end of the non-autonomous transposable element, such as an Ac element. In one embodiment, one terminal end of the Ac element comprises the sequence depicted in SEQ ID NO: 139 and wherein the other terminal end of the Ac element comprises the sequence depicted in SEQ ID NO: 140. In one embodiment, SEQ ID NO: 139 is at the 5'-end of the Ac element, while SEQ ID NO: 140 is at the 3'-end of the Ac element.

In a preferred embodiment, the non-autonomous transposable element is an Ac, Spm, or Mu transposable element.

In one embodiment, the transposase gene is operably linked to a regulatory elements that can express the transposase gene.

This transposase-transposon cassette may be in a plasmid that is present in a bacterium strain selected from the group consisting of *Agrobacterium tumefaciens, Rhizobium trifolii, Rhizobium leguminosarum, Phyllobacterium myrsinacearum, SinoRhizobium meliloti*, and *MesoRhizobium loti*. Hence, one method of the present invention is a method for transforming a plant with a desired polynucleotide, comprising infecting a plant with such a bacterium strain that contains the transposase-transposon cassette.

Another aspect of the present invention is a method for transforming a plant, comprising infecting a plant with any one of the transposon-transposase cassettes of the present invention.

Another aspect of the present invention is a method for transforming a plant, comprising (1) transforming a plant with a transformation plasmid that is suitable for bacterium-mediated plant transformation, wherein the plasmid comprises a transfer-DNA that is delineated by (i) left and right transfer-DNA border sequences, and which comprises (ii) a non-autonomous transposable element, which comprises a desired polynucleotide, and a (iii) a transposase gene, wherein the non-autonomous transposable element and the transposase gene are positioned between the left and right border sequences, and (2) selecting a plant that stably comprises in its genome the non-autonomous transposable element but not the transfer-DNA.

In one embodiment, at least one of the border sequences of this method comprises a sequence that is (i) nicked when exposed to an enzyme involved in bacterial-mediated plant transformation and (ii) not identical to a bacterial border sequence.

In another embodiment, the sequence of at least one of the border sequences comprises the sequence depicted in any one of SEQ ID NOs: 8, 9, 11-13, 15-17, 28-37, 38-51, 85-86, 189, 190, 194-196, and 198.

In another embodiment, the step of selecting a plant comprises positively selecting for a plant that comprises the non-autonomous transposable element and counter-selecting against a plant that comprises the transfer-DNA. In another embodiment, the non-autonomous transposable element comprises the terminal ends of any one of an Ac, Spm, or Mu transposable element. In one embodiment, one terminal end of the Ac element comprises the sequence depicted in SEQ ID NO: 139 and wherein the other terminal end of the Ac element comprises the sequence depicted in SEQ ID NO: 140. In another embodiment, the transposase gene is operably linked to regulatory elements that permit expression of the transposase gene in a plant cell.

In another embodiment, the plasmid that is used to infect the plant is maintained in a bacterium strain selected from the group consisting of *Agrobacterium tumefaciens, Rhizobium trifolii, Rhizobium leguminosarum, Phyllobacterium myrsinacearum, SinoRhizobium meliloti*, and *MesoRhizobium loti*. Accordingly, the present invention also encompasses a method for transforming a plant with a desired polynucleotide, comprising infecting a plant with one of these bacterium strains that contains the transposon-transposase plasmid.

In another embodiment, a cassette is provided, which comprises (1) a first polynucleotide, comprising a sequence that is (i) nicked when exposed to an enzyme involved in bacterial-mediated plant transformation and (ii) not identical to a bacterial border sequence; (2) a second polynucleotide, which may be (i) an imperfect or perfect repeat of the first polynucleotide, or (ii) a bacterial T-DNA border; and (3) a region comprising a virC2 gene, which may be flanked by regulatory sequences.

In one embodiment, the region that comprises the virC2 gene, comprises the sequence depicted in SEQ ID NO: 167. In another embodiment, the cassette is in a plasmid suitable for bacterium-mediated transformation.

Another aspect of the present invention is a method for transforming a plant with a desired polynucleotide, comprising infecting the plant with a bacterium strain comprising any plasmid described herein, wherein the bacterium strain selected from the group consisting of *Agrobacterium tumefaciens, Rhizobium trifolii, Rhizobium leguminosarum, Phyllobacterium myrsinacearum, SinoRhizobium meliloti*, and *MesoRhizobium loti*.

In one embodiment, one or more of the polynucleotides, regions, elements, or domains described herein are not 100% identical in nucleotide sequence to a corresponding bacterium sequence. For instance, a polynucleotide comprising a sequence for a cleavage site according to the present invention, is not 100% identical across its length to an *Agrobacterium* right border sequence.

A transformation cassette may comprise, therefore, sequences that facilitate plant transformation, some, if not all, of which may or may not be identical to a corresponding bacterium sequence. Alternatively, the transformation cassette may comprise one or more bacterial sequences. Thus, the present invention contemplates various permutations of nucleic acid molecules that cover transformation cassettes with no bacterial sequences as well as those that do. For instance, a plant-derived cleavage site might be used in conjunction with a left border sequence from an *Agrobacterium* T-DNA.

Another aspect of the present invention, is a method for identifying a polynucleotide sequence that is involved in bacterium-mediated plant transformation, comprising:

(i) isolating a candidate sequence from a source of genetic material;

(ii) operably replacing one of (a) the first or second polynucleotide, (b) the UI region, (c) the DI region, (d) the UF region, or (e) the AF region of the cassette of claim 1, with the candidate sequence;

(iii) infecting a plant with the cassette using bacterium-mediated transformation; and (iv) determining whether the plant is stably transformed with the desired polynucleotide, wherein a plant that is transformed with the desired polynucleotide indicates that the candidate sequence is involved in bacterium-mediated plant transformation.

BRIEF DESCRIPTION OF THE DRAWINGS

FIG. 2. Sequences flanking right border alternatives. (A) Upstream sequences display a conserved organization of cytosine/thymine residues separated by adenine-rich trinucleotide spacers. The overdrive sequence of pTi15955 is underlined (dotted). Direct repeats are indicated with grey arrows. Transformation efficacies are shown between parentheses as percentages of controls, and represent the mean±SE of three experiments. "+1" indicates the position of the first base of the right border or right border alternative. ND=not determined. (B) Helical stability profile (kcal/mol) across the extended 2-kb St02 region of pSIM551 with 60-bp step size and 120-bp window size. (C) Downstream sequences comprise a DR domain (bold) at a distance of one to 27 nucleotides from the border. Plasmids pSIM781, 793, and 843 contain DNA fragments from a potato homolog of AY566555, a potato homolog of AY972080, and an alfalfa homolog of *Medicago truncatula* AC131026, respectively. Plasmid pSIM582 contains Le01 flanked by the same tomato DNA sequence that flanks the element in its original genomic context. The 5'-GCCC motif is underlined. Transformation frequencies are shown between parentheses as percentages of controls, and represent the mean±SE of three experiments.

FIG. 3. DNA sequences flanking left borders and left border alternatives. Upstream DNA is italicized with UL domain indicated in bold. Left borders and left border alternatives are highlighted in grey. Cytosine clusters are boxed. Frequencies of transgenic plants containing the designated transfer DNA delineated by borders or border alternatives ('T'), the transfer DNA still attached to backbone sequences ('TB'), and backbone-only ('B') are shown on the right and represent the mean±SE of three experiments. ND=not determined.

FIG. 5. Schematic of a transposon-transposase construct of the present invention.

DETAILED DESCRIPTION OF THE PREFERRED EMBODIMENTS

Figure 1:
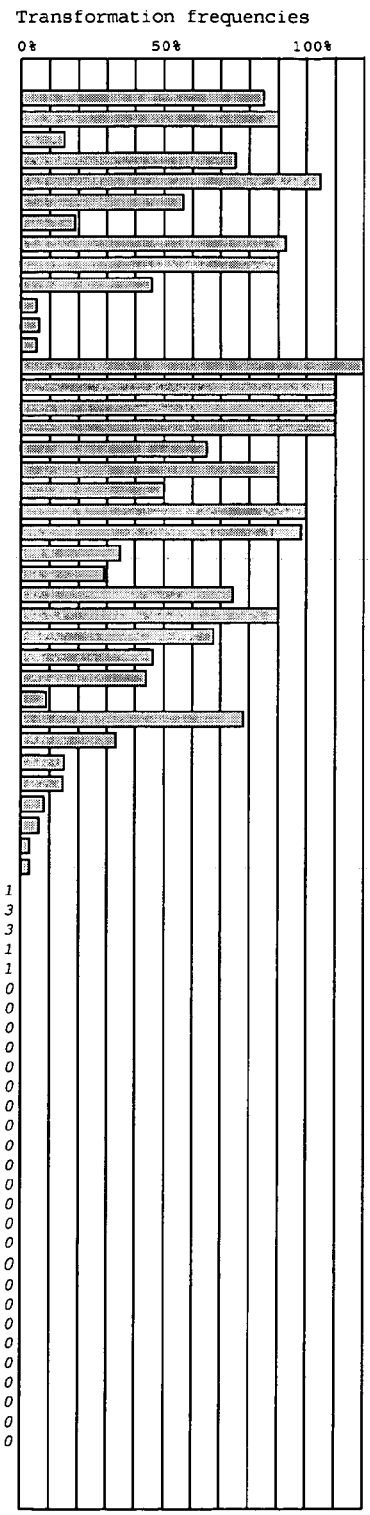
FIG. 1. Sequence requirements for 25-bp cleavage sites. Mismatches to the consensus of *Agrobacterium* Right Borders (CON1) are bold and underlined. Horizontal bars show transformation frequencies compared to those supported by the conventional Right Border Rb02 and the synthetic control cleavage site Ct01, and represent the mean of at least three experiments. The accession numbers of sequences identified in public databases are shown between parentheses. Sequences that were isolated by employing PCR/inverse PCR approaches are indicated with asterisks. (A) *Agrobacterium* Right Borders, indicated as Rb, are derived from plasmids of *A. tumefaciens* (Rb01, Rb02), *A. rhizogenes* (Rb03, Rb04, Rb05, Rb06 and Rb07), and *A. vitis* (Rb04). (B) Synthetic elements are indicated with Sy. (C) The sequences of plant-derived cleavage sites or cleavage site-like sequences are designated with the initials of the species name followed by a number. (D) The overall consensus for both functional Right Borders and cleavage sites is indicated by CON2.

The present invention provides a variety of DNA sequences that are capable of initiating and facilitating the transfer of one polynucleotide into another via standard plant transformation methods. Also identified by the present invention are particular elements within these sequences that help to improve the frequency and integrity of DNA integration. It is an aspect of the present invention that the DNA sequences for any or all of the described transformation elements originate from, or are endogenous to, a plant genome. These transformation elements can be generically described as follows below.

Cleavage site: a function of the cleavage site is to serve as a recognition site for nuclease proteins or protein complexes that may include virD2 and catalyze a single strand DNA nick within the element during *Agrobacterium*-mediated processing.

A desired polynucleotide of interest, which is destined for integration into another nucleic acid molecule, may be linked to at least one of such cleavage sites. For example, the desired polynucleotide may be inserted into a plasmid that can be maintained in *Agrobacterium* and has been engineered to contain these elements, such that the desired polynucleotide is ultimately flanked by one or two cleavage sites.

When there exist two cleavage sites, one may be regarded as being mainly involved in initial cleavage, while the other may be regarded as typically supporting final cleavage. The cleavage sites may be identical in sequence, whereby their functional difference is mediated by specific characteristics of flanking DNA. The transfer DNA contains the initial cleavage site upstream from the final cleavage site. Upstream, with respect to the position of a nucleic acid sequence, means 5'- to the 5'-end of any particular nucleic acid sequence. Downstream, with respect to the position of a nucleic acid sequence, means 3'- to the 3'-end of any particular nucleic acid sequence. All sequences described in this invention refer to the DNA strand that corresponds to the transfer DNA. The non-transfer strand contains the inverse complement of the final cleavage site upstream from the inverse complement of the initial cleavage site.

When a desired polynucleotide is flanked by upstream and downstream elements, it is advantageous for the elements to be oriented as either perfect or imperfect direct repeats of each other.

The sequence of the cleavage site may conform to a consensus sequence, such as that depicted in SEQ ID NO: 84 whereby the sequence of the cleavage site is not identical to an *Agrobacterium* Right Border or Left Border.

(SEQ ID NO:84)
[A/C/G]-[A/C/T]-[A/C/T]-[G/T]-A-[C/G]-NNNNNN-A-
[G/T]-A-[A/C/T]-[A/G]-TCCTG-[C/G/T]-[A/C/G]-N

The consensus sequence analysis indicates that a DNA sequence that is useful for transferring one polynucleotide into another can accommodate nucleotide degeneracy, especially at its 5'-terminus.

According to the consensus sequence, a cleavage site may be 25 nucleotides in length. The present invention is not limited to this length, however, but also contemplates longer and shorter cleavage sites that function as described herein. That is, regardless of their length, the cleavage sites should facilitate cleavage for subsequent integration of a desired polynucleotide to which it is linked into another nucleic acid molecule. Accordingly, elements that are 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 26 nucleotides, 27 nucleotides, 28 nucleotides, 29 nucleotides, and 30 nucleotides elements are envisioned as variants to the 25 nucleotide-long consensus elements described herein.

The functional activity of a putative cleavage site can be tested by inserting it into a "test plasmid" described in the Examples, and using an *Agrobacterium* strain carrying the resulting vector to transform plants such as tobacco. Transformation frequencies achieved with this vector can then be compared to those of conventional benchmark vectors that contain at least one *Agrobacterium* T-DNA Right Border to determine the efficacy of the putative cleavage site to mediate DNA transfer.

Examples of highly efficient synthetic cleavage sites are shown as SEQ ID NOs: 8, 9, 11-13, and 15-17. Similarly efficient plant-derived cleavage sites are depicted in SEQ ID NOs: 28-37 and 85-86. Additional plant-derived cleavage sites that display at least 5% of the activity of Right Borders are shown in SEQ ID NOs: 38-50.

Assessment of the functional activity of a putative cleavage site is more elaborate. Test vectors used for this purpose contain both a functional site for initial cleavage (or Right Border) and the putative site for final cleavage as described in the Examples. Upon transformation and molecular analysis, plants are separated in two different classes. One class of plants only contains the transfer DNA delineated by cleavage sites. This class of transformation events is designated "desired." The second class of plants contains the transfer DNA still linked to plasmid backbone sequences. The smaller the percentage of events belonging to this latter "undesired" class, the better the final cleavage site functions in terminating DNA transfer.

In reference to the DNA strand that comprises the transfer DNA, the position of all DNA regions that are described herein can be identified as upstream and downstream of cleavage sites. The regions include:

(1) The UI region. A UI region may include one or more of the following characteristics:
(a) comprises the first base pair of the initial cleavage site and at least about 47 base pairs immediately upstream from this cleavage site,
(b) is part of a larger sequence that can be predicted by using methods described by, e.g., Huang and Kowalski, 2003, to contain a helical stability that is below the average helical stability, i.e., the sequence may typically requires less energy for unwinding than a random DNA sequence comprising the same number of base pairs,
(c) is part of an adenine-rich (>25% adenine resides) sequence,
(d) comprises at least one adenine-cytosine dinucleotide.
(e) comprises a 45-nucleotide sequence that contains adenine-rich (>25%) trinucleotides interspaced by nucleotides that represent, in at least six cases, a cytosine or thymine (pyrimidine) residue, whereby the most downstream pyrimidine represents either the first base of the initial cleavage site or the base at position −4 relative to the initial cleavage site. See also SEQ ID NOs: 90-97 and 99, and FIGS. 2A and B.
(f) may comprise a sequence that shares at least 70% sequence identity with the overdrive depicted in SEQ ID NO: 88,
(g) is not identical to a region that flanks a T-DNA border in *Agrobacterium* Ti or Ri plasmids.

The UI region may support or enhance any level of initial cleavage activity. For instance, a UI region may enhance the initial cleavage activity by at least 25% compared to the corresponding sequence of the Ti or Ri plasmid.

(2) The DI region. A DI region may include one or more of the following characteristics:
(a) comprises at least 45 base pairs immediately downstream from the initial cleavage site,
(b) comprises a DR domain at a distance of 0-50 base pairs from the initial cleavage site, wherein the DR domain may comprise the sequence depicted in SEQ ID NO: 107,
(c) optionally contains multiple sequences that are identical or inverse complementary to SEQ ID 115 (CCCG),
(d) is not identical to a region that flanks a T-DNA border in *Agrobacterium* Ti or Ri plasmids, and
(e) supports or enhances any level of initial cleavage activity. For instance, a DI region may enhance the initial cleavage activity by at least 25% compared to the corresponding sequence of the Ti or Ri plasmid.

(3) The UF region. A UF region may include one or more of the following characteristics:
(a) comprises at least 40 base pairs immediately upstream from the final cleavage site,
(b) comprises at least 55% adenine or thymine residues (AT-rich),
(c) comprises a sequence that shares at least 70% sequence identity to the UL domain depicted in SEQ ID NO: 120 or to its inverse complement within a distance of about 50 base pairs from the final cleavage site,
(d) optionally comprises a putative binding site for integration host factor with the consensus sequence [A/T]-AT-CAANNNNTT-[A/G] (SEQ ID NO: 129),
(e) is not identical to a region that flanks a T-DNA border in *Agrobacterium* Ti or Ri plasmids, and
(f) supports or enhances any level of initial cleavage activity. For instance, a UF region may enhance the initial cleavage activity by at least 25% compared to the corresponding sequence of the Ti or Ri plasmid.

(4) the AF region. An AF region may include one or more of the following characteristics:
(a) comprises at least part of the final cleavage site and at about two to 40 base pairs flanking downstream DNA,
(b) comprises at least four tightly linked clusters of two or more cytosine bases separated by 1-11 other nucleotides, CCN1-11CCN1-11CCN1-11CC (SEQ ID NO: 122),
(c) is not identical to a region that flanks a T-DNA border in *Agrobacterium* Ti or Ri plasmids, and (d) supports or enhances any level of initial cleavage activity. For instance, an AF region may enhance the initial cleavage activity by at least 25% compared to the corresponding sequence of the Ti or Ri plasmid.

The cytosine cluster domain is thought to form into tertiary quadruplexes at slightly acid or neutral pH, in a similar manner as described for mammalian cytosine clusters. See Zarudnaya et al., Nucleic Acids Res 31: 1375-1386, 2003, and Neidle and Parkinson, Curr Opin Struct Biol 13: 275-283, 2003. It is possible that the specific folding associated with cytosine cluster regions either facilitates or impairs DNA unwinding and/or final cleavage.

Figure 4:
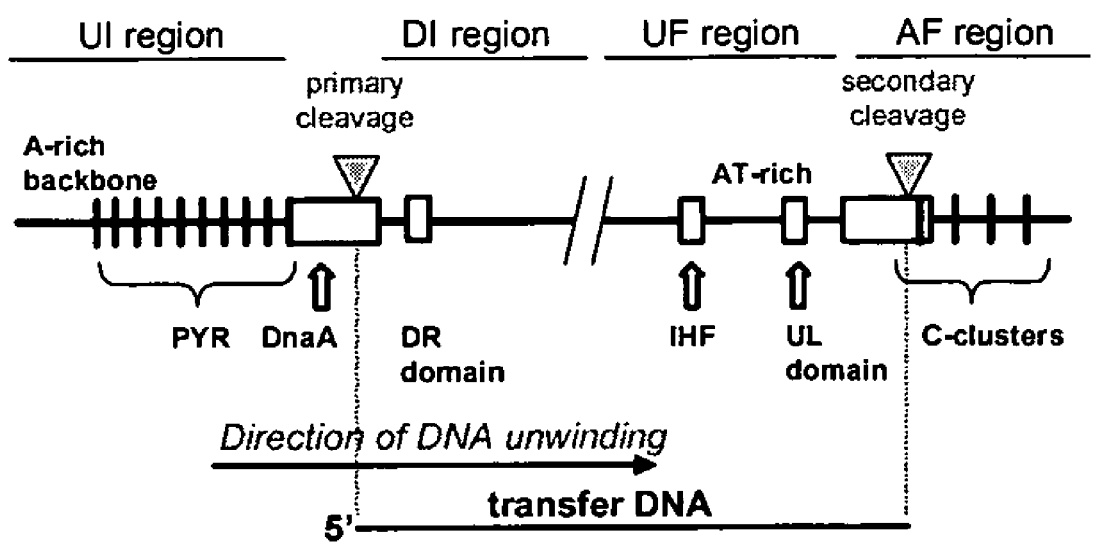
FIG. 4. General organization of extended border regions. Putative sites for DnaA and IHF are indicated with open vertical arrows. The primary cleavage and secondary cleavage sites are represented by open boxes. The cleavage sites could be considered to correspond to transfer-DNA right and left borders, respectively. The direction in which DNA unwinds is indicated with a dashed horizontal arrow.
Figure 6A:
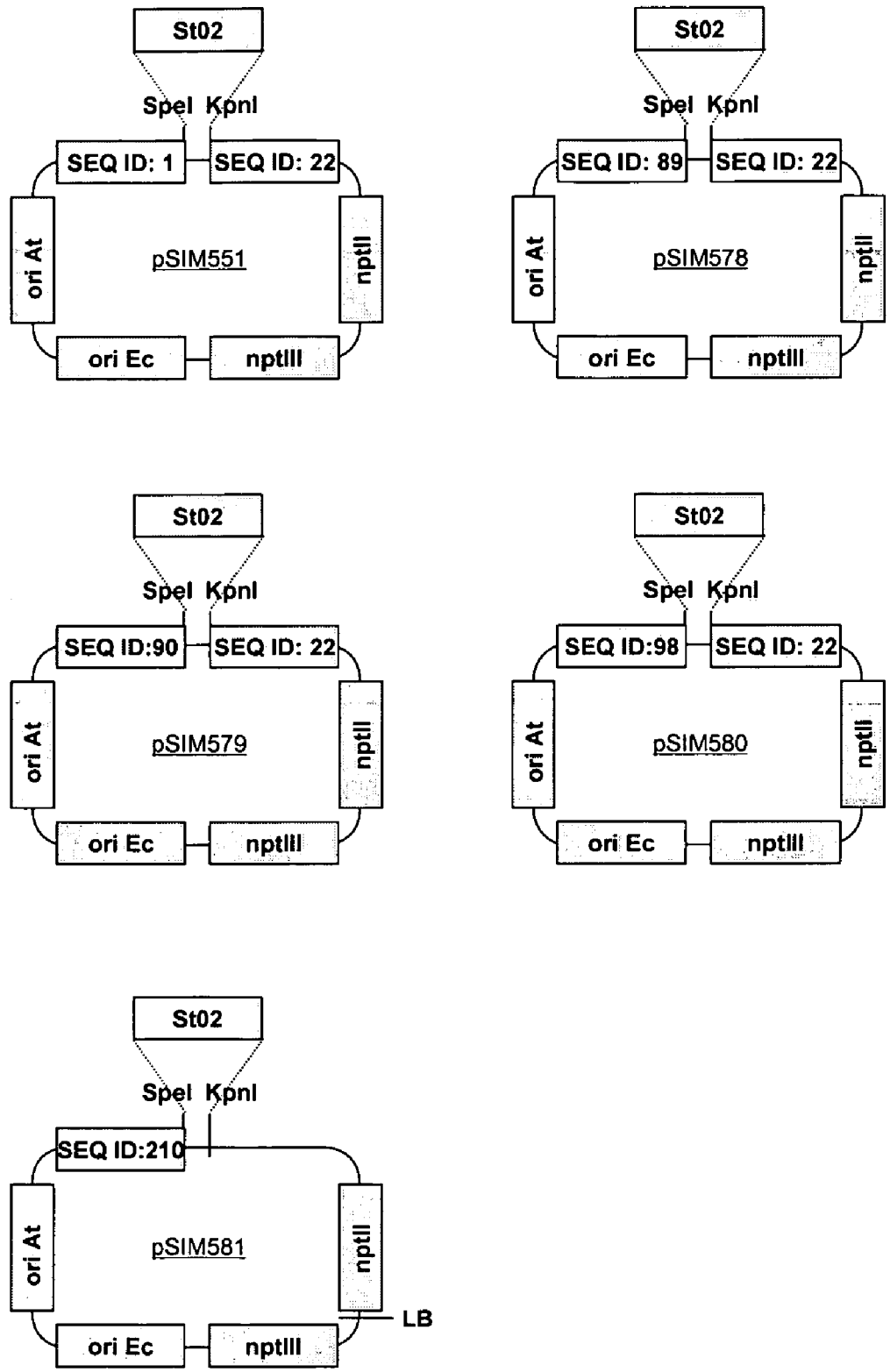
FIG. 6. Plasmid maps: (A) pSIM551, pSIM578, pSIM579, pSIM580, and pSIM581; (B) pSIM843B, pSIM108, pSIM831, pSIM829, pSIM401, and pSIM794; (C) pSIM1026, pSIM1008, pSIM781, pSIM844, and pSIM827. "Ori Ec" denotes an origin of replication from bacteria, including *E. coli*. "Ori At" denotes an origin of replication from bacteria, including *Agrobacterium tumifaciens*.
Figure 6B:
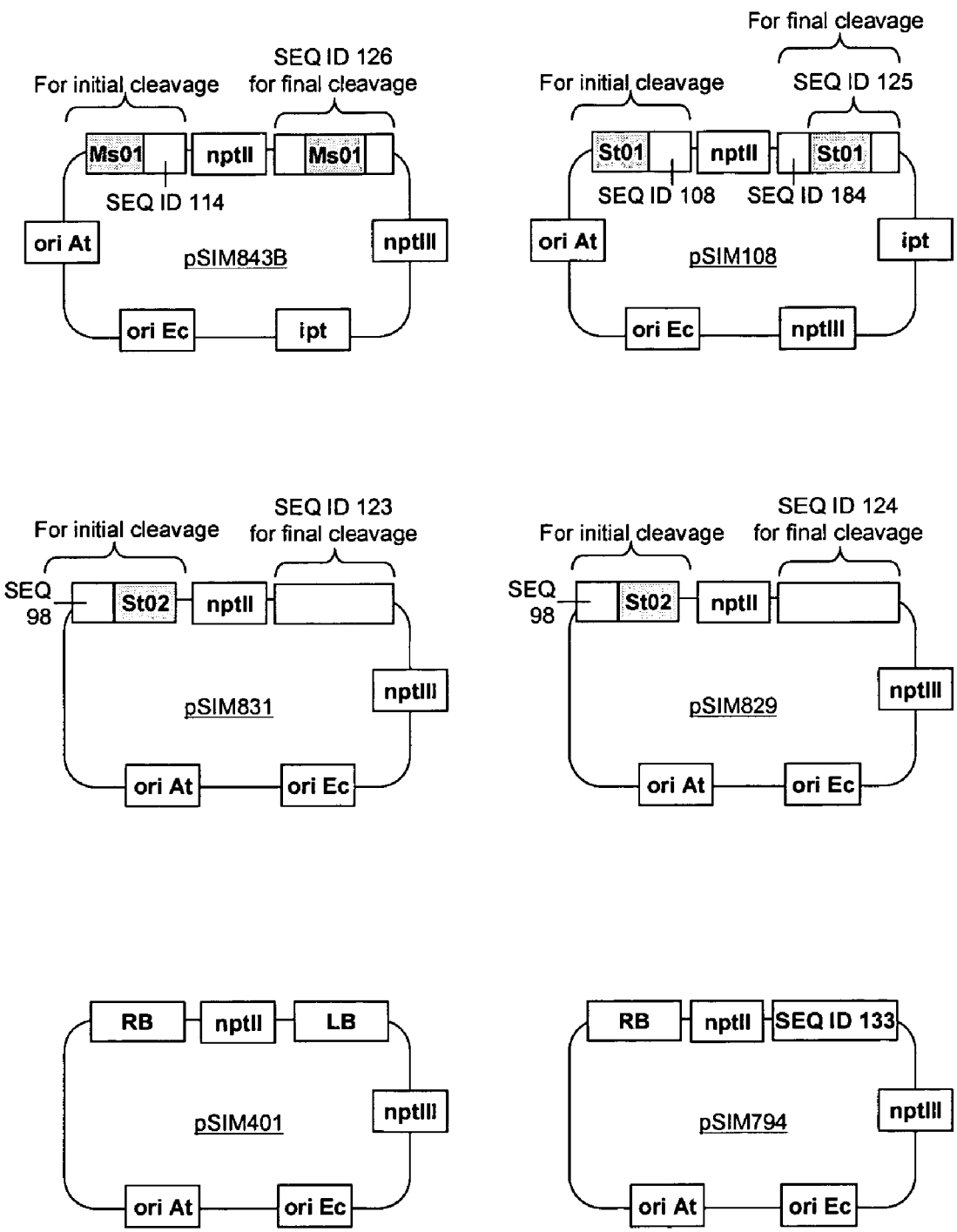
Figure 6C:
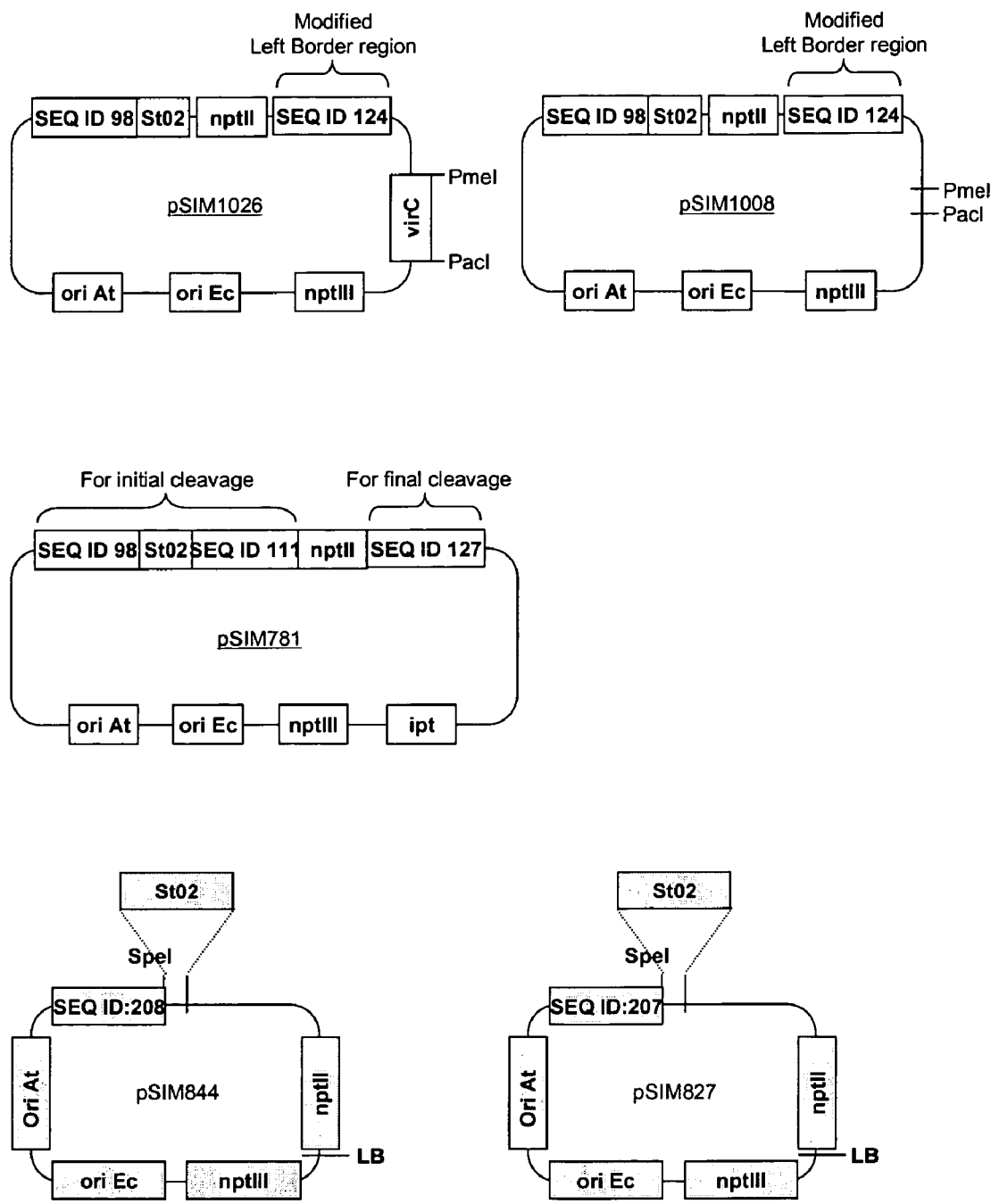

The enzymes necessary for implementing *Agrobacterium*-mediated cleavage include virD2 nicking the top strand of this schematic representation. FIG. 4 is a schematic of the transfer cassette within a plasmid for use in *Agrobacterium*-mediated transformation. The elements are oriented in a manner that corresponds to the sequences described herein. Their orientation also corresponds to the strand that is transferred from *Agrobacterium* to plant cells. It is possible to apply the mirror image of this arrangement in combination with the inverse complement of the sequences shown herein, whereby "downstream" becomes "upstream" and vice versa. Typically, the first enzyme nick is made by virD2 and accessory proteins within the initial cleavage site. Sometimes, however, the pertinent enzyme complex does not effectively make a second nick within the final cleavage site. In this, situation, therefore, the entire top strand of the plasmid becomes linearized, and is transferred to the plant cell.

On the other hand, effective nicking at both the initial cleavage site and the final cleavage site produces a single-stranded DNA molecule that is terminated by residual portions of the cleavage sites. It is desirous that this particular DNA molecule be integrated into a plant genome.

Source of Elements and DNA Sequences

Any or all of the elements and DNA sequences that are described herein may be endogenous to one or more plant genomes. Accordingly, in one particular embodiment of the present invention, all of the elements and DNA sequences, which are selected for the ultimate transfer cassette are endogenous to, or native to, the genome of the plant that is to be transformed. For instance, all of the sequences may come from a potato genome. Alternatively, one or more of the elements or DNA sequences may be endogenous to a plant genome that is not the same as the species of the plant to be transformed, but which function in any event in the host plant cell. Such plants include potato, tomato, and alfalfa plants. The present invention also encompasses use of one or more genetic elements from a plant that is interfertile with the plant that is to be transformed.

In this regard, a "plant" of the present invention includes, but is not limited to angiosperms and gymnosperms such as potato, tomato, tobacco, avocado, alfalfa, lettuce, carrot, strawberry, sugarbeet, cassava, sweet potato, soybean, pea, bean, cucumber, grape, *brassica*, maize, turf grass, wheat, rice, barley, sorghum, oat, oak, eucalyptus, walnut, and palm. Thus, a plant may be a monocot or a dicot. "Plant" and "plant material," also encompasses plant cells, seed, plant progeny, propagule whether generated sexually or asexually, and descendents of any of these, such as cuttings or seed. "Plant material" may refer to plant cells, cell suspension cultures, callus, embryos, meristematic regions, callus tissue, leaves, roots, shoots, gametophytes, sporophytes, pollen, seeds, germinating seedlings, and microspores. Plants may be at various stages of maturity and may be grown in liquid or solid culture, or in soil or suitable media in pots, greenhouses or fields. Expression of an introduced leader, trailer or gene sequences in plants may be transient or permanent.

One or more traits of a tuber-bearing plant of the present invention may be modified using the transformation sequences and elements described herein. A "tuber" is a thickened, usually underground, food-storing organ that lacks both a basal plate and tunic-like covering, which corms and bulbs have. Roots and shoots grow from growth buds, called "eyes," on the surface of the tuber. Some tubers, such as caladiums, diminish in size as the plants grow, and form new tubers at the eyes. Others, such as tuberous begonias, increase in size as they store nutrients during the growing season and develop new growth buds at the same time. Tubers may be shriveled and hard or slightly fleshy. They may be round, flat, odd-shaped, or rough. Examples of tubers include, but are not limited to ahipa, apio, arracacha, arrowhead, arrowroot, baddo, bitter cassava, Brazilian arrowroot, cassava, Chinese artichoke, Chinese water chestnut, coco, cocoyam, dasheen, eddo, elephant's ear, girasole, goo, Japanese artichoke, Japanese potato, Jerusalem artichoke, jicama, lilly root, ling gaw, mandioca, manioc, Mexican potato, Mexican yam bean, old cocoyam, potato, saa got, sato-imo, seegoo, sunchoke, sunroot, sweet casava, sweet potatoes, tanier, tannia, tannier, tapioca root, topinambour, water lily root, yam bean, yam, and yautia. Examples of potatoes include, but are not limited to Russet Potatoes, Round White Potatoes, Long White Potatoes, Round Red Potatoes, Yellow Flesh Potatoes, and Blue and Purple Potatoes.

Tubers may be classified as "microtubers," "minitubers," "near-mature" tubers, and "mature" tubers. Microtubers are tubers that are grown on tissue culture medium and are small in size. By "small" is meant about 0.1 cm-1 cm. A "minituber" is a tuber that is larger than a microtuber and is grown in soil. A "near-mature" tuber is derived from a plant that starts to senesce, and is about 9 weeks old if grown in a greenhouse. A "mature" tuber is one that is derived from a plant that has undergone senescence. A mature tuber is, for example, a tuber that is about 12 or more weeks old.

In this respect, a plant-derived transfer-DNA ("P-DNA") border sequence of the present invention is not identical in nucleotide sequence to any known bacterium-derived T-DNA border sequence, but it functions for essentially the same purpose. That is, the P-DNA can be used to transfer and integrate one polynucleotide into another. A P-DNA can be inserted into a tumor-inducing plasmid, such as a Ti-plasmid from *Agrobacterium* in place of a conventional T-DNA, and maintained in a bacterium strain, just like conventional transformation plasmids. The P-DNA can be manipulated so as to contain a desired polynucleotide, which is destined for integration into a plant genome via bacteria-mediated plant transformation. See Rommens et al. in WO2003/069980, US-2003-0221213, US-2004-0107455, and WO2005/004585, which are all incorporated herein by reference.

Thus, a P-DNA border sequence is different by 1, 2, 3, 4, 5, 6, 7, 8, 9, 10, 11, 12, 13, 14, 15, 16, 17, 18, 19, 20, or more nucleotides from a known T-DNA border sequence from an *Agrobacterium* species, such as *Agrobacterium tumefaciens* or *Agrobacterium rhizogenes*.

A P-DNA border sequence is not greater than 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51% or 50% similar in nucleotide sequence to an *Agrobacterium* T-DNA border sequence.

Methods were developed to identify and isolate transfer DNAs from plants, particularly potato and wheat, and made use of the border motif consensus described in US-2004-0107455, which is incorporated herein by reference.

In this respect, a plant-derived DNA of the present invention, such as any of the sequences, cleavage sites, regions, or elements disclosed herein is functional if it promotes the transfer and integration of a polynucleotide to which it is linked into another nucleic acid molecule, such as into a plant chromosome, at a transformation frequency of about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 15%, or about 5% or at least about 1%.

Any of such transformation-related sequences and elements can be modified or mutated to change transformation efficiency. Other polynucleotide sequences may be added to a transformation sequence of the present invention. For instance, it may be modified to possess 5'- and 3'-multiple cloning sites, or additional restriction sites. The sequence of a cleavage site as disclosed herein, for example, may be modified to increase the likelihood that backbone DNA from the accompanying vector is not integrated into a plant genome.

Any desired polynucleotide may be inserted between any cleavage or border sequences described herein. For example, a desired polynucleotide may be a wild-type or modified gene that is native to a plant species, or it may be a gene from a non-plant genome. For instance, when transforming a potato plant, an expression cassette can be made that comprises a potato-specific promoter that is operably linked to a desired potato gene or fragment thereof and a potato-specific terminator. The expression cassette may contain additional potato genetic elements such as a signal peptide sequence fused in frame to the 5'-end of the gene, and a potato transcriptional enhancer. The present invention is not limited to such an arrangement and a transformation cassette may be constructed such that the desired polynucleotide, while operably linked to a promoter, is not operably linked to a terminator sequence.

In addition to plant-derived elements, such elements can also be identified in, for instance, fungi and mammals. See, for instance, SEQ ID NOs: 173-182. Several of these species have already been shown to be accessible to *Agrobacterium*-mediated transformation. See Kunik et al., Proc Natl Acad Sci USA 98: 1871-1876, 2001, and Casas-Flores et al., Methods Mol Biol 267: 315-325, 2004, which are incorporated herein by reference. Thus, the new BOA elements may be used to extend the concept of all-native DNA transformation (Rommens, Trends Plant Sci 9: 457-464, 2004) to organisms, such as eukaryotes, other than plants.

When a transformation-related sequence or element, such as those described herein, are identified and isolated from a plant, and if that sequence or element is subsequently used to transform a plant of the same species, that sequence or element can be described as "native" to the plant genome.

Thus, a "native" genetic element refers to a nucleic acid that naturally exists in, originates from, or belongs to the genome of a plant that is to be transformed. In the same vein, the term "endogenous" also can be used to identify a particular nucleic acid, e.g., DNA or RNA, or a protein as "native" to a plant. Endogenous means an element that originates within the organism. Thus, any nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species. In other words, a native genetic element represents all genetic material that is accessible to plant breeders for the improvement of plants through classical plant breeding. Any variants of a native nucleic acid also are considered "native" in accordance with the present invention. In this respect, a "native" nucleic acid may also be isolated from a plant or sexually compatible species thereof and modified or mutated so that the resultant variant is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in nucleotide sequence to the unmodified, native nucleic acid isolated from a plant. A native nucleic acid variant may also be less than about 60%, less than about 55%, or less than about 50% similar in nucleotide sequence.

A "native" nucleic acid isolated from a plant may also encode a variant of the naturally occurring protein product transcribed and translated from that nucleic acid. Thus, a native nucleic acid may encode a protein that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in amino acid sequence to the unmodified, native protein expressed in the plant from which the nucleic acid was isolated.

As used herein, "sequence identity" or "identity" in the context of two nucleic acid or polypeptide sequences includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol.*

*Sci.,* 4: 11-17 (1988) e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237-244 (1988); Higgins and Sharp, *CABIOS* 5: 151-153 (1989); Corpet, et al., *Nucleic Acids Research* 16: 10881-90 (1988); Huang, et al., *Computer Applications in the Biosciences* 8: 155-65 (1992), and Pearson, et al., *Methods in Molecular Biology* 24: 307-331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995); Altschul et al., *J. Mol. Biol.*, 215:403-410 (1990); and, Altschul et al., *Nucleic Acids Res.* 25:3389-3402 (1997).

Software for performing BLAST analyses is publicly available, e.g., through the National Center for Biotechnology Information (ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.,* 17:149-163 (1993)) and XNU (Clayerie and States, *Comput. Chem.,* 17:191-201 (1993)) low-complexity filters can be employed alone or in combination.

Multiple alignment of the sequences can be performed using the CLUSTAL method of alignment (Higgins and Sharp (1989) *CABIOS.* 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

Transformation Bacterium

Bacteria species and strains other than those of *Agrobacterium*, e.g., *Agrobacterium tumefaciens*, can be used to transform a plant according to the present invention. For instance, any genera within the family Rhizobiaceae can be used in place of *Agrobacterium* to transform a plant. For instance, members of the *Rhizobium* and *Phyllobacterium* genera can be used to transform a plant according to the present invention. Examples include, but are not limited to, *Rhizobium trifolii, Rhizobium leguminosarum, Phyllobacterium myrsinacearum, SinoRhizobium meliloti, MesoRhizobium loti* bacterial strains, which can be used to transform a plant according to the present invention. See Broothaerts et al., Nature, 433, pp. 629-633, 2005, which is incorporated herein by reference.

Transfer Cassette Embodiments

The present invention does not require the presence of all of the elements described herein in the transfer cassette. Any number of permutations of these elements are envisioned. For instance, a transfer cassette may comprise a desired polynucleotide, which is flanked by cleavage sites only.

Alternatively, another transfer cassette may comprise a desired polynucleotide, which is flanked by cleavage sites and which also comprises one or more of the DI and UF regions. The various elements may be arranged as described herein and as depicted in FIG. 4, but other arrangements are possible and envisioned by the present invention.

The present invention contemplates, therefore, various permutations of the transformation elements disclosed herein, as well as the use of variant forms of any of the corresponding sequences disclosed herein. See the section on "variants" below.

It may be desirable to select particular elements, and sequences or variant sequences that correspond to those elements, which are effective in transforming a particular plant species. That is, it is possible to use the information disclosed herein, as well as the particular sequences disclosed herein, to optimize transformation efficiency between different organisms or plants of different species.

In this regard, the present invention contemplates transforming a plant with one or more transformation elements that genetically originate from a plant. The present invention encompasses an "all-native" approach to transformation, whereby only transformation elements that are native to plants are ultimately integrated into a desired plant via transformation. In this respect, the present invention encompasses transforming a particular plant species with only genetic transformation elements that are native to that plant species. The native approach may also mean that a particular transformation element is isolated from the same plant that is to be transformed, the same plant species, or from a plant that is sexually interfertile with the plant to be transformed.

On the other hand, the plant that is to be transformed, may be transformed with a transformation cassette that contains one or more genetic elements and sequences that originate from a plant of a different species. It may be desirable to use, for instance, a cleavage site, UI, DI, UF, or DF region sequence that is native to a potato genome in a transformation cassette or plasmid for transforming a tomato or pepper plant, for example.

The present invention is not limited, however, to native or all-native approach. A transformation cassette or plasmid of the present invention can also comprise sequences and elements from other organisms, such as from a bacterial species.

Desired Polynucleotides

The origin of the genetic sequences that make up the transformation cassette also may apply to the sequence of a desired polynucleotide that is to be integrated into the transformed plant. That is, a desired polynucleotide, which is located between the primary or initial and secondary or final cleavage site sequences of the present invention, may or may not be "native" to the plant to be transformed. As with the other transformation elements, a desired polynucleotide may be isolated from the same plant that is to be transformed, or from the same plant species, or from a plant that is sexually interfertile with the plant to be transformed. On the other hand, the desired polynucleotide may be from a different plant species compared to the species of the plant that is to be transformed. Yet, the present invention also encompasses a desired polynucleotide that is from a non-plant organism.

A desired polynucleotide of the present invention may comprise a part of a gene selected from the group consisting of a PPO gene, an R1 gene, a type L or H alpha glucan phosphorylase gene, an UDP glucose glucosyltransferase gene, a HOS1 gene, a S-adenosylhomocysteine hydrolase gene, a class II cinnamate 4 hydroxylase gene, a cinnamoyl-coenzyme A reductase gene, a cinnamoyl alcohol dehydrogenase gene, a caffeoyl coenzyme A O-methyltransferase gene, an actin depolymerizing factor gene, a Nin88 gene, a Lol p 5 gene, an allergen gene, a P450 hydroxylase gene, an ADP-glucose pyrophosphorylase gene, a proline dehydrogenase gene, an endo-1,4-beta-glucanase gene, a zeaxanthin epoxidase gene, a 1-aminocyclopropane-1-carboxylate synthase gene, an Rb resistance gene, a Bf2 resistance gene, a Fad2 gene, and an Ant-1 gene. Such a desired polynucleotide may be designed and oriented in such a fashion within a transformation cassette of the present invention, so as to reduce expression within a transformed plant cell of one or more of these genes. See, for instance, Rommens et al. in WO2003/069980, US-2003-0221213, US-2004-0107455, and WO2005/004585, which are all incorporated herein by reference.

Thus, a desired polynucleotide of the present invention may be used to modify a particular trait in a transformed plant that is normally manifested by an untransformed plant. For instance, a desired polynucleotide may be placed into a transformation cassette of the present invention to enhance the health and nutritional characteristics of the transformed plant or it may be used, for instance, to improve storage, enhance yield, enhance salt tolerance, enhance heavy metal tolerance, increase drought tolerance, increase disease tolerance, increase insect tolerance, increase water-stress tolerance, enhance cold and frost tolerance, enhance color, enhance sweetness, improve vigor, improve taste, improve texture, decrease phosphate content, increase germination, increase micronutrient uptake, improve starch composition, and improve flower longevity.

Transformation Vector Embodiments

The present invention does not require the presence of all of the elements described herein in the transformation vector. Any number of permutations of these elements are envisioned. For instance, a transformation vector may comprise both a transfer cassette and one or more UI and AF regions. The elements may be arranged as described herein and as depicted in FIG. 4, but other arrangements are possible and envisioned by the present invention.

Transformation of a plant is a process by which DNA is stably integrated into the genome of a plant cell. "Stably" refers to the permanent, or non-transient retention and/or expression of a polynucleotide in and by a cell genome. Thus, a stably integrated polynucleotide is one that is a fixture within a transformed cell genome and can be replicated and propagated through successive progeny of the cell or resultant transformed plant. Transformation may occur under natural or artificial conditions using various methods well known in the art. See, for instance, METHODS IN PLANT MOLECULAR BIOLOGY AND BIOTECHNOLOGY, Bernard R. Glick and John E. Thompson (eds), CRC Press, Inc., London (1993); Chilton, Scientific American, 248)(6), pp. 36-45, 1983; Bevan, Nucl. Acids. Res., 12, pp. 8711-8721, 1984; and Van Montague et al., Proc R Soc Lond B Biol Sci., 210(1180), pp. 351-65, 1980. Plants also may be transformed using "Refined Transformation" and "Precise Breeding" techniques. See, for instance, Rommens et al. in WO2003/069980, US-2003-0221213, US-2004-0107455, WO2005/004585, US-2004-0003434, US-2005-0034188, WO2005/002994, and WO2003/079765, which are all incorporated herein by reference.

Transformation may rely on any known method for the insertion of nucleic acid sequences into a prokaryotic or eukaryotic host cell, including the bacterium-mediated transformation protocols described herein, such as *Agrobacterium*-mediated transformation, or alternative protocols, such as by viral infection, whiskers, electroporation, heat shock, lipofection, polyethylene glycol treatment, micro-injection, and particle bombardment.

"Activity of the final cleavage site" is determined by comparing the number of transformed plants only containing the DNA that is positioned between initial and final cleavage site with the total number of transformed plants. The final cleavage site determines the fidelity of DNA transfer.

"Activity of the initial cleavage site" is assessed by determining the transformation frequency of a plasmid carrying this cleavage site. Activity is dependent on both the sequence of the initial cleavage site itself and the sequence of flanking DNA. Activities are often expressed as a percentage of the activity of conventional Right Borders. Effective initial cleavage sites display at least 50% of the activity of Right Borders if flanked by DNA sequences that support their activity. Using methods and strains described in this invention, transformation frequencies for conventional right borders average about 10-20 calli/tobacco explant.

"Bacterium-mediated plant transformation" is the modification of a plant by infecting either that plant or an explant or cell derived from that plant with a bacterium selected from the group consisting of *Agrobacterium* sp., *Rhizobium* sp., *Phyllobacterium* sp., *SinoRhizobium* sp., and *MesoRhizobium* sp. to transfer at least part of a plasmid that replicates in that bacterium to the nuclei of individual plant cells for subsequent stable integartion into the genome of that plant cell.

"Cassette" is a DNA sequence that may comprise various genetic elements.

"Cleavage site" is a DNA sequence that is structurally different but functionally similar to T-DNA borders. A cleavage site comprises a sequence that is nicked when exposed to an enzyme involved in bacterium-mediated plant transformation. It can represent a synthetic sequence that may not be present in the genome of a living organism or it can represent a sequence from a living organism such as a plant, animal, fungus, or bacterium.

"Conventional binary plasmid" is a plasmid that ca be maintained in both *E. coli* and *A. tumefaciens*, and contains T-DNA right and left borders that are flanked by at least 10 base pairs of DNA that flank these elements in *Agrobacterium* Ti or Ri plasmids.

"Final cleavage site" is a DNA sequence that is structurally or sequentially different, but functionally similar to, the Left Border of *Agrobacterium* Ti plasmids by comprising a sequence mediating a second cleavage reaction and, thus, defining the end point of the transfer DNA. An effective final cleavage site allows transfer of DNA sequences that do not include sequences downstream from the final cleavage site, i.e., plasmid backbone sequences.

"A flanking sequence" is a sequence immediately next to another sequence.

"Initial cleavage site" is a DNA sequence that is structurally different but functionally similar to the Right Border of *Agrobacterium* Ti plasmids by comprising a sequence that functions as initial cleavage site and, thus, defines the start point of the transfer DNA. An effective initial cleavage site supports or enhances plant transformation compared to a conventional Right Border.

"Non-autonomous transposable element" as used herein is a transposable element that comprises the ends that are required for transposition but which does not encode the protein that is required for transposition. Thus, a non-autonomous transposable element will transpose only if the gene encoding the protein required for transposition is expressed from either a different position in the genome or from a plasmid or DNA fragment that resides in the same plant cell.

A "terminal end of a transposable element" is a sequence at the 5' or 3' end of a transposable element that is required for non-autonomous transposition. Such sequences may comprise about 100 to about 300 nucleotides.

"T-DNA border" is a polynucleotide of approximately 25-base pairs in length that comprises a sequence that can be nicked when exposed to an enzyme or enzyme complex involved in bacterium-mediated plant transformation and that can define the single stranded DNA fragment that is transferred from the bacterium to the plant cell.

"UF region" is a DNA sequence that (a) comprises at least 40 base pairs immediately upstream from either the final cleavage site or left border, (b) comprises at least 55% adenine or thymine residues (AT-rich), (c) comprises a sequence which has at least 70% sequence identity to the UL domain depicted in SEQ ID NO: 120 or its inverse complement, within a distance of 50 base pairs from the final cleavage site, (d) optionally comprises a putative binding site for integration host factor with the consensus sequence [A/T]-ATCAANNNNTT-[A/G] (SEQ ID NO: 129) that is positioned within 200 base pairs from the final cleavage site or left border, (e) is not identical to a region that flanks a T-DNA border in *Agrobacterium* Ti or Ri plasmids, and (f) supports or enhances activity of the initial cleavage site.

"UI region" is a DNA sequence that (a) comprises the first base pair of either the initial cleavage site or right border and at least about 47 base pairs immediately upstream from this cleavage site; (b) is part of a larger sequence that can be predicted by using methods described by, e.g., Huang and Kowalski, 2003, to contain a helical stability that is below the average helical stability, i.e., the sequence may typically requires less energy for unwinding than a random DNA sequence comprising the same number of base pairs; (c) is part of an adenine-rich (>25% adenine resides) sequence; (d) comprises at least one adenine-cytosine dinucleotide; (e) comprises a 45-nucleotide sequence that contains adenine-rich (>25%) trinucleotides interspaced by nucleotides that represent, in at least six cases, a cytosine or thymine (pyrimidine) residue, whereby the most downstream pyrimidine represents either the first base of the initial cleavage site or the base at position −4 relative to the initial cleavage site. See also SEQ ID NOs: 199-208, and FIGS. 2A and B; (f) may comprise a sequence with at least 70% sequence identity to the overdrive depicted in SEQ ID NO: 88; (g) is not identical to a region that flanks a T-DNA border in *Agrobacterium* Ti or Ri plasmids; and (h) supports or enhances activity of the initial cleavage site.

"UI-like region" is a sequence that resembles a UI region but differs in that it (1) represents *Agrobacterium* sequences flanking a Right Border, or (2) impairs the efficacy of a Right Border or cleavage site. The UI-like region may reduce transformation frequencies to less than that of a conventional Right order-flanking DNA sequence. For instance, it may reduce a transformation frequency to less than about 25%.

"Transformation vector" is a plasmid that can be maintained in *Agrobacterium*, and contains at least one Right Border or initial cleavage site. Infection of explants with *Agrobacterium* strains carrying a transformation vector and application of transformation procedures will produce transformed calli, shoots, and/or plants that contain at least part of the transformation vector stably integrated into their genome. The vector may comprise a selectable marker to aid identification of plants that have been stably transformed.

A "selectable marker" is typically a gene that codes for a protein that confers some kind of resistance to an antibiotic, herbicide or toxic compound, and is used to identify transformation events. Examples of selectable markers include the streptomycin phosphotransferase (spt) gene encoding streptomycin resistance, the phosphomannose isomerase (pmi) gene that converts mannose-6-phosphate into fructose-6 phosphate; the neomycin phosphotransferase (nptII) gene encoding kanamycin and geneticin resistance, the hygromycin phosphotransferase (hpt or aphiv) gene encoding resistance to hygromycin, acetolactate synthase (als) genes encoding resistance to sulfonylurea-type herbicides, genes coding for resistance to herbicides which act to inhibit the action of glutamine synthase such as phosphinothricin or basta (e.g., the bar gene), or other similar genes known in the art.

A "variant," as used herein, such as a variant of any of the nucleic acid molecules or polypeptides described herein, is understood to mean a nucleotide or amino acid sequence that deviates from the standard, or given, nucleotide or amino acid sequence of a particular gene or protein. The terms, "isoform," "isotype," "homolog," "derivative," and "analog" also refer to "variant" forms of a nucleotide or an amino acid sequence. An amino acid sequence that is altered by the addition, removal or substitution of one or more amino acids, or a change in nucleotide sequence, may be considered such a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software.

The present invention encompasses a variant that has one or more point mutations compared to one of the sequenced disclosed herein. For instance, any one of the cleavage site sequences depicted by SEQ ID NOs: 8, 9, 11-13, 15-17, 28-37, 38-51, 85-86, 189, 194-196, may comprise one or more point mutations. That mutated variant may then be readily tested for activity or its effect on transformation efficiency, simply by replacing the original sequence with the mutated version and determining whether the sequence is cleaved and whether the efficiency of transformation is maintained, increased, or decreased.

Similarly, any of the sequences disclosed herein for a UI, DI, UF, or AF region may be mutated and similarly tested for activity and effect on transformation efficiency.

Thus, the present invention is not limited to the sequences disclosed herein that correspond to a particular transformation element. Rather, actual sequences can be used in any permutation to create useful and effective transformation cassettes and plasmids, or one or more of the component transformation elements may be mutated, tested for activity, and then incorporated into a desired transformation cassette or plasmid.

In this regard, a variant sequence of the present invention, such as a variant of a cleavage site or UI, DI, UF, or AF region, may be a functional homolog of a particular sequence. By this it is understood that a cleavage site that is a variant of, for instance, one of SEQ ID NOs: 8, 9, 11-13, 15-17, 28-37, 38-51, 85-86, 189, 194-196, but which still can be cleaved by an enzyme, is a functional derivative of the original sequence. By the same token, the present invention encompasses functional derivatives of any of all of the transformation elements, e.g., UI, DI, UF, and AF regions, disclosed herein.

A variant sequence of the present invention also encompasses shorter and longer sequences of those specific sequences disclosed herein. For instance, the cleavage site sequence depicted in SEQ ID NO: 8 may be positioned within a larger fragment of DNA, which may or may not be plant DNA. The subsequently larger fragment may then be inserted into a transformation cassette or plasmid. Thus, the present invention is not limited to manipulating only a polynucleotide that consists of a particular SEQ ID NO: sequence. Accordingly, one may use one of the sequences of the present invention, such as SEQ ID NO: 8, to identify and isolate another sequence homolog from a plant or any other organism genome. It may be desirable to isolate a fragment of that genomic DNA that includes sequences flanking the homolog of interest. The larger fragment, within which is included the same or similar homolog to a desired sequence described herein, may then be tested according to the methods described herein for functional activity, i.e., it may be tested to determine what effect, if any, it has on transformation efficiency in comparison to a control system that does not include the larger fragment homolog. Thus, a "variant" of any of the sequences described herein, not only that exemplified by SEQ ID NO: 8, be it a sequence for a cleavage site or for a UI, DI, UF, or AF region, for instance, encompasses longer versions of the corresponding sequences disclosed herein.

Conversely, a "variant" of the present invention also encompasses polynucleotides that are shorter than a corresponding sequence of the present invention. That is a variant polynucleotide may be "a part of" a sequence disclosed herein. It is well within the purview of the skilled person to make truncated versions of a sequence disclosed herein. For instance, the present invention contemplates truncating a cleavage site, for instance, by any number of nucleotides and then testing that cleavage site for activity. For example, one may truncate the cleavage site depicted in SEQ ID NO: 8 by removing the 5 nucleotides from the 3'-end of SEQ ID NO: 8 and then test that truncated fragment of SEQ ID NO: 8 for cleavage activity. That is, one may test to see if a pertinent enzyme can still cleave the truncated SEQ ID NO: 8, by virtue of assaying for the cleavage directly or by ascertaining the effect of the truncated SEQ ID NO: 8 on transformation efficiency compared to a control system, which employs the full-length sequence of SEQ ID NO: 8.

A truncation may be made at either end or within a particular sequence described herein. Thus, a variant that comprises a part of, say, SEQ ID NO: 8, may be any part of SEQ ID NO: 8. SEQ ID NO: 8 is only used here as an example. Any of the sequences disclosed herein may be truncated in such fashion and then tested for subsequent activity and/or transformation efficiency.

Any of the sequences described herein can be chemically synthesized. That is, it may not be necessary to physically isolate and purify a particular sequence from an organism genome prior to use. For this reason, a "truncated" version of a sequence described herein may be obtained by terminating chemical synthesis at any desired time point during manufacture.

Thus, a variant that is a "part of" a sequence disclosed herein may be made directly using chemical synthesis techniques rather than physically obtained from the actual polynucleotide in question. The same strategy applies for the longer variant forms: it is possible to chemically synthesize a polynucleotide, within which comprises a particular sequence described herein.

The following examples serve to illustrate various embodiments of the present invention and should not be construed, in any way, to limit the scope of the invention.

All references cited herein, including patents, patent application and publications, are hereby incorporated by reference in their entireties, where previously specifically incorporated or not.

Having now fully described this invention, it will be appreciated by those skilled in the art that the same can be performed within a wide range of equivalent parameters, concentrations and conditions, without undue experimentation. This application is intended to cover any variations, uses, or adaptations of the invention, following in general the principles of the invention, that include such departures from the present disclosure as come within known or customary practice within the art to which the invention pertains and as may be applied to the essential features hereinbefore set forth.

Example 1

Initial Cleavage Sites

Isolated plant sequences were used as effective initial cleavage sites to mediate DNA transfer as well as effective final cleavage sites to limit the co-transfer of vector backbone sequences. In fact, backbone transfer frequencies with plant-derived cleavage sites that were linked to upstream AT-rich regions and downstream C-cluster regions were lower than obtained with conventional Left Borders. The DNA sequences described herein permits the construction of efficient all-native transfer DNAs that can be used for the production of intragenic potato, tomato, and alfalfa plants.

Cleavage Sites

Initial cleavage sites function in the initiation of DNA transfer and are positioned in transformation plasmids at the junction of (i) the 5'-end of sequences destined for transfer from *Agrobacterium* to plant cells (the transfer DNA) and (ii) plasmid backbone sequences required for maintenance of the plasmid in *Agrobacterium*. Their sequences deviate from that of the *Agrobacterium* Right Borders shown in SEQ ID NOs: 1-7 denoted Rb01-Rb07, respectively. Examples of synthetic initial cleavage sites are depicted in SEQ ID NOs: 8-13, which are denoted Sy01-Sy13.

To test the functional activity of putative initial cleavage sites, such sequences were linked to (i) an upstream 109-base pair *Agrobacterium* pTi15955 sequence preceding the conventional right border (SEQ ID NO: 1), and (ii) a DI region shown in SEQ ID NO: 22. This construct was inserted into a plasmid containing an expression cassette for the neomycin phosphotransferase (nptII) selectable marker gene. *Agrobacterium* strains carrying the resulting 'single element' test vector were subsequently used to infect tobacco explants.

Two weeks after infection, the average numbers of calli per explant were compared to those produced with a control plasmid containing Rb01 (15.3±0.5). As shown in FIG. 1, all putative cleavage sites enabled DNA transfer. However, base substitutions C6A, A13C, C19G, C20G, and T21A of cleavage site Sy03, Sy07, Sy11, Sy12, and Sy13, respectively, lowered transformation frequencies more than five-fold.

Sequence requirements for initial cleavage were further determined by testing the efficacy of plant sequences that resemble the *Agrobacterium* consensus (FIG. 1). In addition to the cleavage site of a previously characterized *Solanum tuberosum* (potato) P-DNA (Rommens et al., Plant Physiol 135: 421-431, 2004), designated here as St01 (SEQ ID NO: 23), a large number of new elements were identified by searching publicly available databases including those maintained by "The National Center For Biotechnology Information" using, for instance, the "Motif Alignment and Search Tool" (Bailey and Gribskov, J Comput Biol 5: 211-21, 1998) and "advanced BLASTN" (Altschul et al., Nucleic Acids Res 25: 3389-3402, 1997). Search motifs included CAGGATATA GTA (SEQ ID NO: 130), using parameters such as (i) penalty for nucleotide mismatch=−1, and (ii) expect=105. All hits were further analyzed to determine whether they uncovered sequences resembling CON1 and/or CON2. Additional databases that were searched include those covering Solanaceae (sgn.comell.edu/), Compositae (compositdb.ucdavis.edu/), and *Medicago truncatula* (genome.ou.edu/medicago.html). Alternatively, border-like sequences were isolated from genomes by employing a polymerase chair reaction (PCR) approach. For this purpose, plant DNAs (2 µg), partially digested with SauIIIA, were ligated with 192-bp BamHI-EcoRV fragments of pBR322. The resulting DNAs were used as templates for amplification with a degenerate primer, SEQ ID NO: 24, and an anchor primer, SEQ ID NO: 25, with 49° C. annealing temperature and 2.5-minute extension time. Subsequent PCRs were performed with the amplified DNAs ligated with pGEM-T as templates using the degenerate primer together with either SP6 or T7 primers at a slightly higher annealing temperature (52° C.). The products of these reactions were inserted into pGEM-T and sequenced to design primers for conventional inverse PCRs to determine the actual putative cleavage site sequences.

Among the new plant-derived cleavage sites, only the *Arabidopsis thaliana* At01 element (SEQ ID NO: 26) fully matched the *Agrobacterium* right border consensus.

However, this element displayed only 65% of the activity of the conventional Right Border Rb02. The lower activity of At01 suggests that the guanine base at position +4 (G4) is not as effective as T4.

Most cleavage sites contain at least one mismatch with the consensus sequence of *Agrobacterium* Right Borders (CON1) shown in FIG. 1 and depicted in SEQ ID NO: 27:

(SEQ ID NO:27 )
[A/C/G][A/T][A/T][G/T]AC[A/C/T]N[C/G/T][A/C/G]

[A/C/G][A/C/G]ATATATCCTG[C/T]CA

Despite the presence of one to three mismatches with CON1, the following cleavage site displayed at least 50% activity. This result demonstrates that *Agrobacterium* appears to not have exploited the full potential of border sequence variation. See SEQ ID NOs: 28-37. Other cleavage sites include those depicted in SEQ ID NOs: 38 and 39. Cleavage sites that displayed activities between about 50% and 5% are depicted in SEQ ID NOs: 40-50.

Mismatches and/or point deletions in 31 cleavage site-like sequences from a variety of plant species resulted in either low activity (less than about 5%) or no detectable activity at all. See the sequences depicted in SEQ ID NOs: 38, 39, 52-83, 193, and 197.

By comparing tested Right Borders, cleavage sites, and cleavage site-like elements, a consensus, CON2, was identified. See FIG. 1D and SEQ ID NO: 84:

(SEQ ID NO:84)
5'-[A/C/G]-[A/C/T]-[A/C/T]-[G/T]-A-[C/G]-NNNNNN-A-

[G/T]-A-[A/C/T]-[A/G]-TCCTG-[C/G/T]-[A/C/G]-N.

Mismatches that reduced transformation frequencies most dramatically include, apart from those mentioned above, A5G and C6G.

The high activity of tomato Le01 prompted us to search for homologs in related plant species. Identification of identical copies in pepper (Ca01, SEQ ID NO: 85) and potato (St02, SEQ ID NO: 86) DNAs indicates that a single cleavage site can be used for all-native DNA transformation of at least three different *Solanceous* plant species, potentially facilitating the governmental approval process. We also identified a potato homolog of tomato Le05. However, the reduced efficacy of that cleavage site may limit its applicability for plant transformation.

To obtain an effective cleavage site for use in maize, we can modify Zm01 (SEQ ID NO: 50) by replacing a single base pair. Substitution of the guanine residue at position 3 by a thymine residue will yield a Zm01-derived cleavage site, designated Zm01M1 (SEQ ID NO: 51).

Similarly, an effective *Brassica* cleavage site can be obtained by modifying SEQ ID NO; 52 to create SEQ ID 189, or by modifying SEQ ID NO: 197 to produce SEQ ID NO: 198.

Efficient cleavage sites for soybean can be obtained by modifying Gm01 (SEQ ID NO: 38) and Gm02 (SEQ ID NO: 39) to create Gm01M1 (SEQ ID NO: 195) and Gm02M1 (SEQ ID NO: 196), respectively.

Example 2

Spacing Requirements for an Extended Overdrive Domain

The effective test plasmid pSIM551 contained St02 linked to the sequences that contain a 31-bp fragment of pTi15955 inserted between novel sequences. The DNA region comprising this sequence and the first nucleotide of Le01 is the part of SEQ ID NO: 87 depicted in SEQ ID NO: 199, and represents a UI region. This arrangement placed the cleavage site for potato at a distance of 12 base pairs from the overdrive, an element that was reported to promote DNA transfer (van Haaren et al., 1987) and depicted in SEQ ID NO: 88.

Although the overdrive element is believed to function in a position independent manner (Shurvinton and Ream, 1991), we found that a single base pair insertion between St02 and upstream DNA (SEQ ID NO: 89) in pSIM578 reduced transformation frequencies of pSIM579 about two-fold (FIG. 3A). Furthermore, the 5'-CAA trinucleotide insertion into the UI region of pSIM579 (SEQ ID NO: 90) had an even greater negative effect on the efficacy of transformation, lowering it to 35%.

To study the molecular basis of the apparent overdrive-St02 spacing requirement, we compared the UI region of pSIM551 (SEQ ID NO: 199) with corresponding T-DNA flanking regions of *Agrobacterium* plasmids (SEQ ID NOs: 91-97 shown in SEQ ID NOs: 200-206). The aligned sequences generally contained cytosine or thymine residues at conserved four-nucleotide intervals, separated by adenine-rich (46%) trinucleotide segments (FIG. 3A). This arrangement resulted in a high occurrence of AC dinucleotide repeats (27%) approaching that of the overdrive element itself (42%).

Whereas the sequences upstream from (1) the Right Borders of *Agrobacterium* plasmids and (2) the UI region of pSIM551 comprised at least six pyrimidine residues at conserved positions, the impaired activity of pSIM578 and 579 was correlated with UI regions that contained five and four such residues, respectively (FIG. 2A). Additional evidence for the importance of correctly spaced pyrimidines was obtained by analyzing the UI region of pSIM580, which contained the pentanucleotide 5'-ACCAA insertion between St02 and upstream DNA (part of SEQ ID NO: 98 shown in SEQ ID NO: 207). Maintenance of six pyrimidines at conserved positions in this plasmid was associated with the same DNA transfer activity as that of the original vector pSIM551 (FIG. 2A).

To further test the functional significance of correctly spaced pyrimidines, the UI region of pSIM551 was replaced by a sequence that displayed 77% identity with the *Agrobacterium* pRi2659 sequences upstream from the right border (Hansen et al., 1992). Immediate linkage with St02 yielded a UI region (part of SEQ ID NO: 99 shown in SEQ ID NO: 208) in pSIM844 that supported high transformation frequencies (125%) (FIG. 2A). However, disruption of the pyrimidine spacing by a single base pair insertion resulted in a UI-derived region of pSIM827 (part of SEQ ID NO: 100 shown in SEQ ID NO: 207) that lowered transformation frequencies to 7%.

Having correlated the original spacing of pyrimidines with efficient DNA transfer, we now also tested the functional relevance of adenine-rich spacers. For this purpose, the UI region of pSIM551 was replaced with a tomato DNA fragment carrying nine pyrimidines at conserved positions but lacking a high percentage of adenine residues in the intervals (part of SEQ ID NO: 101 shown in SEQ ID NO: 210). The resulting vector pSIM581 displayed only 15% of the transformation efficacy of pSIM551, indicating that adenine-rich intervals or AC repeats play a role in the functional activity of the UI region (FIG. 2A).

Since adenine-rich DNA is often associated with low helical stability regions, we determined the helical stability profile of pSIM551 using WEB THERMODYN (Huang and Kowalski, 2003). This analysis identified a 120-bp sequence immediately upstream from the St02 cleavage site and including the UI region to represent the lowest helical stability region of the pSIM551 backbone (FIG. 2B and data not shown). The association of an easily unwound DNA region immediately upstream from the RBA may be functionally relevant because *Agrobacterium* Ti and Ri plasmids contain similar low helical stability regions at their Right Borders. For instance, pTiC58 contains a 120-bp region preceding the border with a stability of 116 kcal/mol. Analogous to the association of low helical stability regions with the initiation of plasmid replication (Natale et al., 1993), these upstream DNAs may be involved in the initiation of DNA transfer. We conclude that the overdrive is part of a larger UI-like region that is conserved among *Agrobacterium* plasmids. This domain supports St02-mediated DNA transfer if correctly spaced relative to the initial cleavage site, and may be involved in local DNA unwinding. The sequence that comprises the first nucleotide of the initial cleavage site and at least about 47 nucleotides of flanking upstream DNA is designated UI region.

Example 3

The Role of Sequences Downstream from Initial Cleavage Sites

Given that upstream DNA sequences adjacent to the border region influenced transformation efficacy, we sought to test the effect of downstream modifications. As shown in FIG. 2C, analyses of the sequences downstream from Right Borders and depicted in SEQ ID NOs: 102-106 identified decamers that shared the consensus 5'-[A/C/T]-[A/C]-[A/C/T]-[A/G/T]-[A/T]-T-[A/C]-G-[G/T]-[G/T] (SEQ ID NO: 107) with the 5'-part of the overdrive, and were positioned at a distance of one to 27 nucleotides from the right border. This "downstream from right border" (DR) domain was also identified in both the potato-derived transfer DNA (Rommens et al., 2004) of pSIM108 (SEQ ID 108) and DI regions of test vectors such as pSIM551 (SEQ ID NO: 109) (FIG. 2C). An increase in the spacing between Le01 and DR domain from 24 nucleotides in the DI region of pSIM551 to 48 nucleotides in pSIM920 (SEQ ID NO: 110) lowered transformation frequencies by 40% (FIG. 3C), indicating that the supporting function of DR domain on border activity is spacing dependent.

Because downstream DNA sequences represent the actual transfer DNA that is intended for plant transformation, we replaced the original bacterial sequences of pSIM551 with two unique potato DNA fragments. The pSIM551-derivative pSIM793 (SEQ ID NO: 113), which contained a DR domain at 27 nucleotides from Le01 yielded about the same transformation frequency as pSIM551. In contrast, the potato DNA fragment of pSIM582 (SEQ ID NO: 112), which contained a DR domain with several mismatches to the consensus, displayed only 59% activity. Interestingly, replacement of Le01-flanking DNA sequences by an alfalfa DNA fragment that contained two different DR domains (SEQ ID NO: 114) triggered unusually high transformation frequencies for the resulting vector pSIM843 (168%) (FIG. 3C). This high activity may also be due, in part, to the specific sequence of the upstream DNA of pSIM843, which contains eight 5'-GCCC (SEQ ID NO: 115) repeats. We conclude that sequences flanking right border alternatives play an important role in supporting plant DNA transfer. These sequences comprise upstream ACR and downstream DR domains.

Example 4

Substitution of Left Borders by Right Border Alternatives

The above-described studies had shown that CON2-matching 25-bp elements function as effective right border alternatives if flanked by sequences that support their activity. As shown in SEQ ID NOs: 116-119, functional differences exist, and there is divergent sequence organization, at and around, the left and right border sites. In contrast to right borders, for instance, left borders:

(1) are preceded by AT-rich DNAs each comprising an "upstream from left border" (UL) domain on either DNA strand with the consensus sequence

```
                                         (SEQ ID NO:120)
A[C/T]T[C/G]A[A/T]T[G/T][C/T][G/T][C/G]A[C/T][C/T]
[A/T];
```

(2) share a more conserved consensus sequence:

```
                                         (SEQ ID NO:121)
5'-[A/G]TTTACA[A/C/T][A/C/T][A/C/T][C/G]AATATATCCT
GCC[A/G]; and
```

(3) are linked to downstream plasmid backbone DNA by cytosine clusters ("C-clusters") that conform to the consensus CCN1-11CCN1-11CCN1-11CC (SEQ ID NO: 122) (FIG. 3A).

Direct evidence for the role of the C-cluster organization in supporting left border activity was obtained by comparing the fidelity of DNA transfer for pSIM831 and 829. Both vectors contained an expression cassette for the nptII gene preceded by DNA regions comprising St02 as right border alternative, and were confirmed to support the same high transformation frequencies as pSIM551 (data not shown). The vectors also contained almost identical DNA regions for secondary cleavage, shown in SEQ ID NOs: 123 and 124, respectively, which differed only in that pSIM829 contained a 10-bp insertion in the fourth left border-associated C-cluster (FIG. 3B).

The effect of this small change was assessed by classifying regenerated shoots in three groups based on PCR analyses. The first 'T' group only contained the intended transfer DNA, and would therefore be predicted to have arisen from primary cleavage events at the right border followed by secondary cleavage at the left border. Plants containing both the transfer DNA and additional backbone DNA sequences were classified in a second "TB" group, and most likely represented events where the second copy of the border alternative failed to function in terminating DNA transfer. The third 'B' group of events only contained backbone DNA, and probably arose from initial cleavage reactions at the second St02 copy. This genotype classification demonstrated that pSIM831 was more than twice as effective as pSIM829 (41% vs. 17%) in producing 'T' events (FIG. 3B).

The sequence comprising at least part of the final cleavage site and at least one nucleotide of flanking downstream DNA, and comprising a C-cluster region, is designated AF region.

Efficacy of right border alternatives as sites for secondary cleavage was studied by testing pSIM108 and 843B. The vectors contained St01 and Ms01, respectively, as right border alternative. The downstream region of pSIM108, shown in SEQ ID 125, contained (1) AT-rich (62%) DNA (SEQ ID NO: 184), comprising a putative binding site for integration host factor with the consensus 5'-[A/T]-ATCAANNNNTT-[A/G] (SEQ ID NO: 129), and derived from the terminator of the potato ubiquitin-3 gene (Garbarino et al., 1994) containing a UL domain, and (2) a second copy of St01 associated with plasmid backbone DNA comprising five C-clusters (SEQ ID NO: 125).

Similarly, the DNA region intended for secondary cleavage in pSIM843B (SEQ ID NO: 126) contained a second copy of Ms01 preceded by an AT-rich (87%) alfalfa DNA fragment, and followed by downstream C-clusters (FIG. 3B). Vector pSIM401, which contained the extended left border region of pTiC58, was used as control. PCR genotyping demonstrated that both pSIM108 and 843B yielded even higher frequency of backbone-free transformation events (41.1 and 33.9%) than obtained with the control (26.0%), thus indicating that right border alternatives can be used to replace left borders.

A modification of pSIM843B that both eliminated the UL domain and altered the spacing of C-clusters yielded a UF region that lowered the frequency of desired 'T' transformation events for the resulting vector pSIM849 (SEQ ID NO: 127) to 10.2% (FIG. 3B). This reduced frequency was associated with an about two-fold increased transfer of DNAs that are still attached to their vector backbones, indicating that the modifications of flanking DNA interfered with effective secondary cleavage at the second Ms01 copy. Similar alterations of the UF region of pSIM108 resulted in a sequence (SEQ ID NO: 127) that reduced transformation efficacy about four-fold (FIG. 3B).

Sequences of UF regions of pSIM108, pSIM843B and pSIM781 are depicted in SEQ ID NOs: 184-186.

Collectively, this data demonstrate that right border alternatives can be used to replace left borders if associated with upstream UL domain and downstream C-clusters. Even small changes in this organization were found to have a profound effect on the frequency of backbone-free plant transformation. Replacement of the internal nptII gene expression cassette of pSIM843B by alfalfa DNA would make it possible to produce intragenic alfalfa plants.

The full region of pSIM843B for efficient initial cleavage comprises UI region, Ms01, and DI region, and is shown in SEQ ID NO: 131. The full region of pSIM843B for efficient final cleavage comprises UF region, Ms01, and AF region, and is shown in SEQ ID NO: 132.

Example 5

Cleavage Sites from Eukaryotes Other than Plants

In addition to plant-derived cleavage sites, such elements can also be identified in, for instance, fungi and mammals. See, for instance, SEQ ID NOs. 173-182. Several of these species have already been shown to be accessible to *Agrobacterium*-mediated transformation (Kunik et al., Proc Natl Acad Sci USA 98: 1871-1876, 2001; Casas-Flores et al., Methods Mol Biol 267: 315-325, 2004). Thus, the new elements may be used to extend the concept of all-native DNA transformation (Rommens, Trends Plant Sci 9: 457-464, 2004) to eukaryotes other than plants.

The present invention also contemplates methods for identifying other polynucleotide sequences that can be used in place of the specific sequences described herein. For instance, it is possible to identify polynucleotide sequences that can replace cleavage sites, as well as polynucleotide sequences that can replace the regions that are upstream and downstream of the cleavage sites.

A sequence that is upstream of the cleavage site is removed and a different polynucleotide is inserted. The sequence of the different polynucleotide may or may not be known. With all the other elements in place to facilitate appropriate transformation in the transfer cassette and plasmid, the insertion is tested to determine if the different polynucleotide facilitates transformation. The assay makes it possible to identify alternative polynucleotide sequences that can be used to build an effective transfer cassette. Accordingly, one may transform a plant with a transformation plasmid in which a candidate polynucleotide sequence has been inserted in place of one of the established sequences described herein. Successful plant transformation is monitored and the inserted DNA further characterized.

Hence, various elements described herein can be replaced with candidate DNA sequences to test whether those candidate DNA sequences are useful as alternative functional elements for successful plant transformation (see FIG. 4).

Example 6

Alternative Final Cleavage Sites

In an effort to replace the Left Border by a universal sequence that would allow an efficient production of plants only containing the intended transfer DNA, we considered the cleavage systems that mediate intercellular transfer of plasmid DNA during bacterial conjugation. These systems share analogies with the mechanism that directs bacterium-to-plant cell DNA transfer: most proteins involved in cleavage are plasmid-encoded and some of the recognition sites share a similar organization or display a weak level of sequence homology (Waters et al., 1991).

One such system is that of the *Salmonella typhimurium* IncI1 plasmid R64. Initiation and termination of the transfer of this plasmid occurs at a specific origin of transfer, oriT. This sequence consists of two units, the nick region and a 17-base pair repeat sequence, that are recognized by the relaxosome proteins nikB and nikA, respectively (Feruya and Komano, 2000).

Here, the fidelity of transfer of DNA fragments that are delineated by a Right Border and oriT was studied. We demonstrate that oriT mediates efficient but imprecise DNA cleavage, that is Right Border-dependent and nikb helicase-independent. Since most cleavage events occur within about 200 base pairs upstream from oriT, binary vectors comprising a plant-derived Right Border alternative sequence together with oriT can be used for all-native plant DNA transformation. For a review of *Agrobacterium* mediated DNA transfer and the role of origins of transfer, see Zechner er al., 2000, Conjugative DNA transfer process, pp 87-174. In; The horizontal gene pool. Bacterial plasmids and gene spread. Herwood Academic publishers, Amsterdam, The Netherlands, which is incorporated herein by reference. Various OriT sequences can be identified by performing sequence comparison searches of publicly available nucleotide databases, such as GenBank and EMBL, to identify sequences that are identical or share sequence identity with a known OriT sequence. The present invention permits use of those other various OriT sequences in any of the cassettes and constructs disclosed herein. For instance, once one such sequence has been identified, it can be cloned into the appropriate cassette to replace an existing and functional OriT, and then that candidate OriT sequence tested to see if it facilitates DNA clevage, compared to a control cassette, which is known to contain an active functional OriT cleavage sequence.

OriT Mediates Secondary DNA Cleavage

Vector pSIM580 contains a Right Border region that consists of the potato-derived element St02 flanked by the upstream low-helical stability region of pTiC58 and a downstream expression cassette for the selectable marker gene encoding neomycin phosphotransferase (nptII). Infection of tobacco (*Nicotiana tabacum*) explants with an *Agrobacterium* LBA4404 strain carrying this vector resulted in transformation frequencies that are similar to those of conventional binary vectors containing the Right and Left Border of the *Agrobacterium* T-DNA. This result confirms previous findings that St02 functions as effective site for DNA cleavage.

A 92-base pair R64 DNA fragment containing the cleavage site for conjugative DNA transfer (nucleotides 53798-53889 of Genbank accession AB027308) flanked by minimally-required supporting DNA sequences (oriT) was inserted downstream from the nptII gene expression cassette to create vector pSIM1144. Upon transformation with *Agrobacterium* strains carrying pSIM580 and pSIM1144, respectively, tobacco plants were molecularly analyzed for the presence of DNA segments on either side of where oriT was inserted in pSIM1144. As expected, both segments were identified in all plants transformed with the single-border plasmid pSIM580. However, only 71% of plants derived from the pSIM1144 transformation had this genotype. Absence of the second DNA segment in the remainder of plants indicated the occurrence of oriT-dependent secondary cleavage. Interestingly, the frequency of pSIMI1144-mediated backbone-free DNA transformation was similar to that of the 'two T-DNA border' control vector pSIM109 (Table 4).

The above results suggested that DNA transfer termination was mediated by oriT. To determine whether this element also could enable the initiation of DNA transfer, a new vector was tested that contained the nptII gene expression cassette inserted between two oriTs. Infection of tobacco explants with *Agrobacterium* strains carrying this vector, pSIM 1129, did not result in any transformation events (Table 4). This result demonstrates that oriT does not display Right Border activity and is dependent on the presence of a Right Border alternative to function as Left Border replacement. This Right Border-dependence indicates that oriT-mediated cleavage only occurs in unwound and possibly single-stranded DNA.

OriT-Mediated Cleavage Requirements for T-DNA Versus Conjugative Plasmid DNA Transfer The backbone-free transformation obtained with St02-oriT vectors was unexpected in light of the requirements for plasmid DNA conjugation. In *E. coli*, single-stranded DNA cleavage at oriT requires the catalyzing activity of the 5'-relaxase domain of nikB. Because *Agrobacterium* does not encode this protein, oriT-mediated T-DNA cleavage appears to be nikB-independent. To determine a possible role for nikB, we performed a functional test of the pSIM1144-derived vector pSIM794, which contains an expression cassette for the nikB relaxase domain in its backbone DNA. Employment of this vector resulted in a similar frequency of backbone-free tobacco transformation as shown before for pSIM1144 (Table 4).

Vector pSIM795 is identical to pSIM794 except that the oriT sequence was positioned in the opposite direction. Since orientation determines which strand is nicked and transferred during conjugation, we expected that the strand cleaved at the Right Border would not undergo a secondary cleavage event. Surprisingly, the new vector was found to function in a similar way to pSIM794 (Table 4) Thus, secondary DNA cleavage is independent of the orientation of oriT.

Another difference in oriT's function became apparent from the fact that oriT only functioned in mediating the termination of T-DNA transfer. In contrast, bacterial conjugation requires oriT as site for both the initiation and termination of DNA transfer. To study whether the presence of an additional copy of oriT would facilitate DNA excision, we produced the pSIM1144-derived vectors, namely pSIM783 and pSIM785, respectively. These modifications did not greatly alter the frequency of backbone-free transformation (Table 4). Confirming that cleavage is independent of nikB, insertion of this gene into the backbone of pSIM783 and 785, creating pSIM784 and 786, respectively, did not greatly affect backbone-free transformation frequencies (Table 4).

Collectively, our results indicate that the mechanism of oriT-mediated secondary cleavage is different from that of plasmid conjugation initiated by oriT.

OriT-Mediated Cleavage

The positions of oriT-mediated cleavage sites were first assessed by determining the size of integrated transfer DNAs. For this purpose, DNA from 24 backbone-free pSIM794 plants was subjected to PCR analysis. As shown in FIG. 3A, the T-DNA breakpoints of 12 plants were positioned within a 120-bp DNA segment immediately upstream from oriT. In these cases, the plants contained almost the entire sequence from Right Border to oriT. Shorter transfer DNAs were present in eight additional plants with breakpoints ranging from at least 120 to more than 700 bp upstream from oriT (FIG. 3A).

Sequence analysis of three randomly-chosen plants demonstrated that all these plants contained a cytosine residue as last nucleotide of the integrated transfer DNA (FIG. 3B). Assuming the absence of nuclease activity during DNA transfer, this finding implied a conservation of the nucleotide at the 5'-end of the DNAs that are (i) nicked at T-DNA borders, (ii) nicked at oriT during bacterial conjugaton, and (iii) nicked in the vicinity of oriT prior to *Agrobacterium*-mediated DNA transfer to plants.

Efficient Backbone-Free Potato Transformation

The efficiency of secondary cleavage at conventional Left Borders of vectors such as pSIM109 is even lower in potato (15%) than tobacco (25-35%). This result demonstrates that the fidelity of Left Border activity is dependent on which plant species is infected. Since oriT efficacy in *Agrobacterium* was not assumed to be influenced by plant factors, a test was performed to demonstrate that oriT could be a more effective mediator of secondary cleavage than the Left Border for DNA transfer to potato. The test entailed infecting potato stem explants with vector pSIM1144. PCR analysis of the resulting plants demonstrated a backbone-free transformation frequency of 44%. As expected, this frequency was similar to that determined for pSIM1144-transformed tobacco, and more than two-fold higher than for potato plants transformed with the conventional vector. Our results show that oriT can be used as an effective alternative to Left Borders in both tobacco and potato. Since cleavage generally occurs within several hundreds of nucleotides upstream from oriT, effective plant transformation should employ vectors that contain a DNA spacer between the genes of interest and the end of the transfer DNA.

Instead of using Left Borders or cleavage sites that conform to SEQ ID NO: 84, it is also possible to use the sequence depicted in SEQ ID NO: 133, or a fragment thereof, as a final cleavage site. Actual single stranded DNA cleavage often occurs between the 14th and 15th nucleotide. However, it is also possible that transferred DNA comprises either more or less than 14 nucleotides of SEQ ID NO: 133.

Binary vectors that contain (1) either a Right Border or initial cleavage site upstream from a polynucleotide and (2) SEQ ID NO: 133 as final cleavage site. downstream from this polynucleotide can be used to efficiently transfer the polynucleotide, often still flanked by about three base pairs of the 3'-terminus of the Right Border or initial cleavage site and about 14 base pairs (CCCGAAAAACGGGA) (SEQ ID NO: 191) of the alternative final cleavage site. Together, the transferred sequence can be designated "transfer DNA."

Given the size of plant genomes, only plant species with very small genomes may not contain the 14 base pair sequence of SEQ ID NO: 133 that is, transferred, as part of the transfer DNA, from the binary vector to the plant cell. For instance, *Arabidopsis* contains ACCGAAAAACGGGA (SEQ ID NO: 192) instead of SEQ ID NO: 191. The mismatch at position "1" would represent a single point mutation, which is acceptable for all-native DNA transformation because point mutations occur spontaneously in plant genomes. Furthermore, it is possible to use parts of SEQ ID NO: 133 as alternative final cleavage site. For instance, SEQ ID NO: 134 to SEQ ID NO: 137, or functional fragments thereof, may be used.

Interestingly, the fidelity of DNA transfer with vectors that contain SEQ ID NO: 133 as an alternative final cleavage site is higher than similar vectors that contain a conventional Left Border region instead. Table 1 shows the genotypes of tobacco plants derived from an infection with *Agrobacterium* LBA4404 carrying specific plasmids. Plasmid pSIM794 contains an expression cassette for the neomycin phosphotransferase (nptII) gene inserted between a conventional Right Border and SEQ ID NO: 133. Plasmid pSIM795 contains the same plasmid except that SEQ ID NO: 133 is positioned in the inverse complementary (antisense) position. The benchmark vector contains conventional Left and Right Borders (pSIM109), and the previously discussed pSIM1008 was used as control vector. See Table 1. The use of alternative final cleavage site makes it unnecessary to use associated UF and AF regions.

We have shown that DNA segments positioned between Right Border and oriT can be effectively transferred to plant cells. With the nick site at the Right Border functioning as start point for DNA transfer, sequences within ~200-bp upstream from oriT were generally identified as end points. By facilitating DNA transfer without being transferred itself, oriT is an excellent tool for all-native DNA transformation. Therefore, it is possible to use such a transformation cassette to genetically manipulate plants without integrating any superfluous foreign DNA into the plant genome.

A candidate protein catalyzing the oriT-dependent secondary cleavage is virD2, which potentially cleaves at the nick site of the oriT of plasmid RP4. This nick site shares sequence homology with that of both T-DNA borders and the R64 oriT that was used in our studies. Although R64 oriT-dependent cleavage lacks specificity in Agrobacterium, the 5'-terminus of cleavage sites appear to contain, like those of RP4 and T-DNA borders, a cytosine residue. The observed imprecise cleavage indicates that the cleavage protein is not directed to one particular site. Binding in the vicinity of R64 oriT may be promoted by proteins such as integration host factor that are involved in virtually all forms of nucleoid manipulation. However, there are no proteins that would specifically anchor virD2 at the nick site of oriT. The R64 nikA protein is not expressed in Agrobacterium and would also not complex with Agrobacterium proteins such as virD2, and virD1 would not find an appropriate binding site within oriT. The requirement of accessory proteins for sequence and strand specific cleavage is not without precedent. The RP4 relaxase TraI requires TraJ and TraK as specificity determinants, and the orf20 cleavage protein of the conjugative transposon Tn916 looses its cleavage specificity in the absence of its accessory integrase protein.

The catalyzing effect of oriT on secondary cleavage may be due to the presence of protein binding site within oriT that supports the cleavage of an endonuclease such as virD2. For instance, oriT is known to contain a binding site for integration host factor, a protein involved in virtually all forms of nucleoid manipulation including DNA unwinding. It is possible that this protein supports DNA cleavage at left borders in a similar way as reported previously for oriT.

Instead of the R64, it is also possible to use the oriTs of Agrobacterium or Rhizobium strains. Such elements are known to reside on short DNA fragments (for instance, Genbank accessions AF010180, AF242881, AF528525). Other sequences that may be used as alternatives for Left Borders include the oriTs of plasmids of, for instance, Corynebacterium (X99132), Escherichia (DQ269444, Y14016, AB011548), and Klebsiella (AF300473). Thus, any oriT may be used to mediate secondary cleavage of T-DNAs.

It is also possible to employ oriT-like sequences to support secondary cleavage. Such sequences represent low helical stability regions (Huang and Kowalski, Nucleic Acids Res 31: 3819-3821, 2003). Such regions can be tested for efficacy by producing vectors containing a Right Border and the candidate region for secondary cleavage, and testing transgenic plants for the absence of backbone.

SEQ ID 219 shows the oriT region of Agrobacterium strain C58 that can be used instead of a Left Border.

Combination Vectors

It is possible to create a DNA cleavage region that combines an oriT sequence with either a second oriT or any Left Border or Left Border alternative.

SEQ ID NO: 220 shows a sequence comprising two oriT sequences followed by a spacer.

SEQ ID NO: 221 shows a sequence comprising oriT and a modified potato-derived Left Border alternative, followed by a spacer.

SEQ ID NO: 222 shows a sequence comprising oriT and another potato-derived Left Border alternative, followed by a spacer.

It is also possible to employ vectors that contain, from 5' to 3', (i) either a Right Border or Right Border alternative to initiate preliminary cleavage, (ii) oriT to mediate secondary cleavage, and (iii) either a second oriT or a left Border or Left Border alternative to mediate tertiary cleavage. Agrobacterium strains carrying plasmids with this configuration can be used to transform plants with the DNA segment delineated by oriTs.

Figure 7:
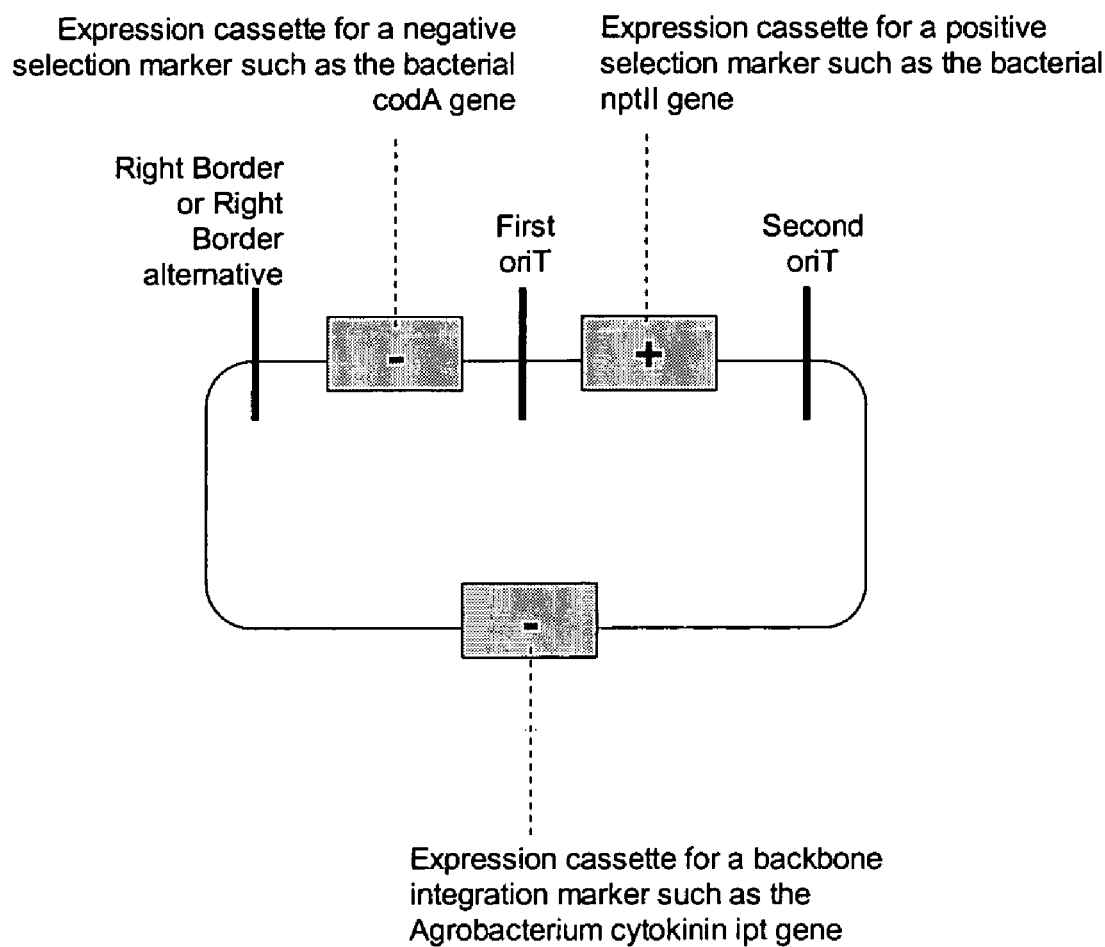
FIG. 7. A schematic diagram of an OriT construct.
Figure 8:
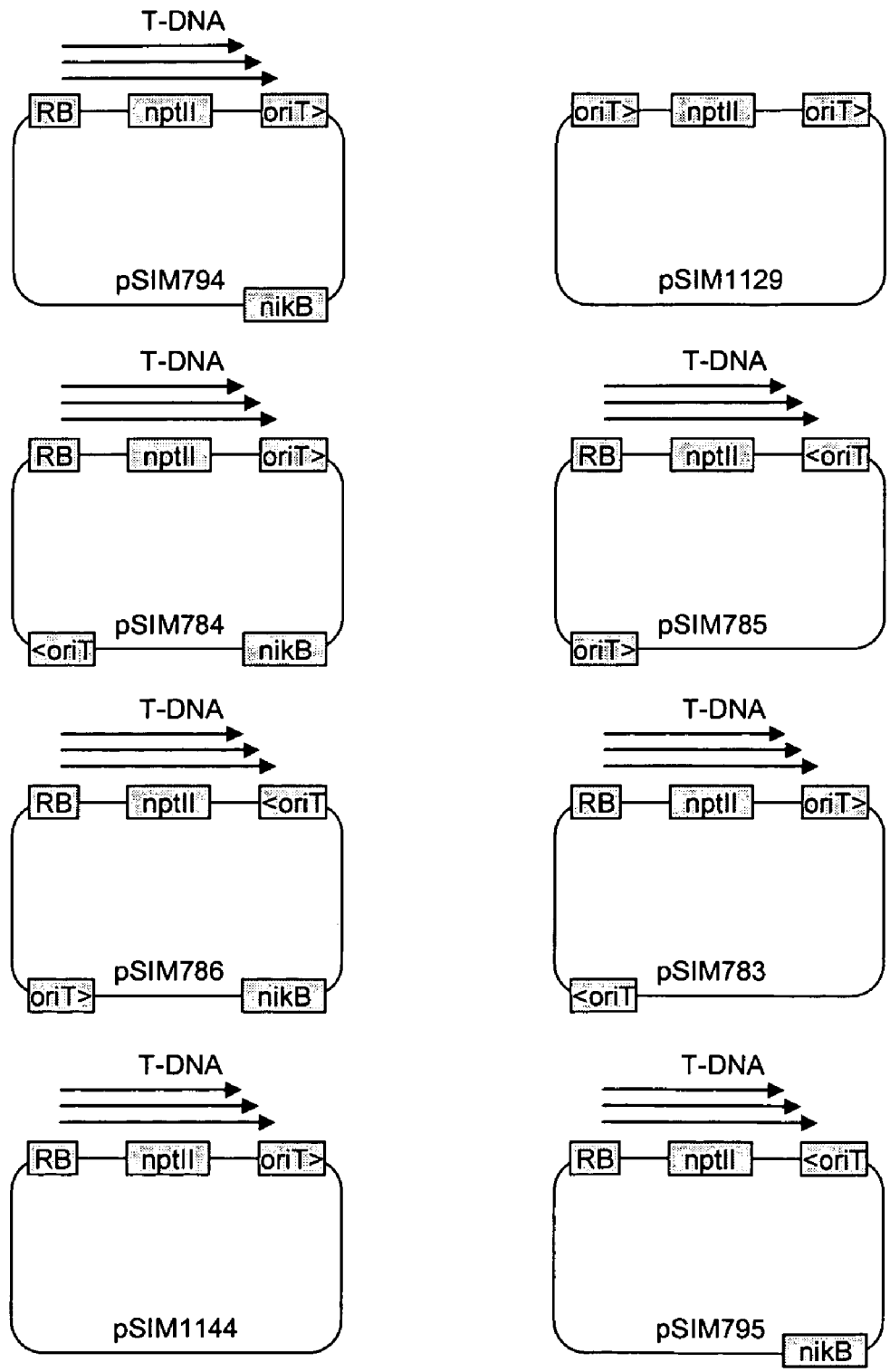
FIG. 8. Schmatic diagrams of pSIM794, pSIM1129, pSIM 784, pSIM785, pSIM786, pSIM783, pSIM1144 and pSIM795. The black arrows illustrate that the DNA strand may be cleaved at a various sites when employing an OriT sequence in the construct to yield cleaved DNA strands that differ in size.

Identification of transformed plants can be facilitated by inserting (i) a negative selectable marker such as the bacterial codA gene between Right Border and first oriT, (ii) a positive selectable marker between first and second oriT, and (iii) a negative selectable marker such as the bacterial ipt gene between second oriT and Right Border. FIG. 7 shows such a configuration.

Example 7

T-DNA-Delivered Transposon-Based Transformation

Agrobacterium-mediated plant transformation is based on the transfer of single stranded plasmid DNA segments (T-DNAs) from Agrobacterium to the nuclei of infected plant cells. Upon transfer, the virE2-coated linear DNA is temporarily protected from nuclease attack. However, only about 25% of transferred T-DNAs are not degraded. That subset of virE2-coated transfer T-DNA escapes degradation by integrating into double-stranded chromosome breaks through illegitimate recombination. Such breaks occur at random positions that generally represent CG-low and repetitive DNA. Frequently low expression levels of T-DNA-based transgenes have been linked to higher order genome structures and RNA silencing.

In contrast to passive T-DNA integration, transposable elements such as the maize (Zea mays) Activator (Ac) integrate by employing a specialized form of DNA recombination that occurs by a cut-and-paste mechanism and may involve a DNA intermediate. Excision of the transposable element could be initiated by the assembly of an active synaptic complex in which the two ends of the element are paired and held together by bound Ac-transposase subunits. Reinsertion occurs when the 3' hydroxyl at each end of the excised element performs a nucleophilic attack on the host DNA, producing an integration intermediate that contains single-strand gaps in the flanking host DNA sequence. In the final stage of the transposition process, the non-complementary ends of the broken donor DNA molecule are processed and rejoined and the gaps are filled at the insertion site. These repair processes generate a small excision site footprint, often comprising a few base pairs of transposon end sequence, as well as a characteristic duplication of the target octonucleotide at the insertion site.

The Ac element encodes an 807-amino acid transposase that binds specifically to multiple motifs positioned near the termini of the transposon. Separation of the two functions of Ac creates a two-component transposition system. An expression cassette for the transposase gene represents the first component, and the second component exists of a non-autonomous Dissociation (Ds) element that contains the ends required for non-autonomous transposition. Ds elements frequently transpose from their original positioning T-DNAs into single- or low-copy CG-rich regions associated with genes. This site preference generally supports high expression levels of genes positioned within the elements. To stabilize the optimized expression, plants need to be self or cross fertilized for segregation of transposase source from Ds in progeny plants. This requirement makes it difficult to apply the Ds transposition method to crops that are vegetatively propagated and suffer from inbreeding depression such as potato.

The need to introduce transposable elements into plants by transforming them with T-DNAs can be circumvented by having the elements transpose from extragenous DNA into the plant genome. The only currently available method is based on the polyethylene glycol-mediated co-transformation of *Nicotiana plumbaginifolia* with plasmids containing Ds and Ac-transposase, respectively. However, treatment of two million protoplasts yielded only nine plants that contained a Ds insertion while apparently lacking any plasmid DNA (Houba-Herin et al., Plant J; 6: 55-66, 1994). This low frequency indicates that it would be difficult to apply the method for commercial purposes, especially for plants that are either not as accessible to protoplast transformation as *N. plumbaginifolia* or are difficult to regenerate from protoplasts. Various studies describe that Ds elements also excise, at low frequencies, from replicating geminiviruses in transfected plants (Laufs et al., Proc Natl Acad Sci USA 87: 7752-7756; Shen and Hohn, Plant J 2: 35-42, 1992; Shen et al., Plant Mol Biol 36: 387-92). However, transformation frequencies for this alternative method are unclear and are likely to be extremely low or nonexistent because excision has not been linked to subsequent integration into the plant genome.

Here, we describe a new transformation method that is based on Ds transposition from non-integrating T-DNAs. By using the T-DNA as a vehicle for delivery of the transposable element into the nucleus and then selecting against T-DNA integration, frequencies of single-copy and plasmid-free transformation were obtained that are only three-fold lower than obtained with conventional T-DNA transformation in potato.

Instead of using either borders or cleavage sites as sequences that define the ends of the polynucleotide intended for plant transformation, it is also possible to use the termini of plant transposable elements. Until now, transposon-based transformation systems were based on either protoplast transformation (Houba-Herin et al., 1994) or geminivirus vectors (Laufs et al., 1990; Shen and Hohn, 1992; Wirtz et al., 1997; Shen et al., 1998). Both these systems are extremely inefficient, and have not been pursued for commercial purposes. In contrast to conventional transposon-based transformation, we employ the transfer DNA to deliver the transposable element into the plant nucleus. Excision from the transferred DNA, followed by integration into the plant genome, results in effective plant transformation.

The plasmid used to demonstrate the efficacy of T-DNA-delivered transposon-based (TDTB) transformation contains the conventional Left and Right Border regions of *Agrobacterium*. Between these border regions, the following elements were inserted: (1) an expression cassette for the transposase gene of the maize transposable element Ac (SEQ ID NO: 138), (2) a non-autonomous transposable element designated 'transposon' comprising an expression cassette for the neomycin phosphotransferase (nptII) gene positioned between the 5' and 3' ends of the Ac element depicted in SEQ ID NOs: 139 and 140, and (3) an expression cassette for the cytosine deaminase (codA) gene. See FIG. 5. Transgenic plants were created as follows:

Tobacco explants (4,500) were infected with an *Agrobacterium* strain carrying the plasmid described above. The infected explants were co-cultivated and transferred to medium containing kanamycin (100 mg/L) to select for plant cells expressing the nptII gene. After one month, shoots were transferred to fresh media that also contained the non-toxic 5-fluorocytosine (5-FC). Stable integration of the entire transfer DNA would result in constant expression of the codA gene and subsequent conversion of 5-FC into toxic 5-fluorouracil (5-FU). Thus, only transformed shoots that did not express the codA gene would be expected to survive this selection step. A total of 141 shoots were harvested after selection periods of 10, 20, 30 and 45 days on 5-FC, and PCR analyzed to determine whether the shoots carried integrated T-DNAs still harboring the transposon at its original resident position or whether they carried the transposon integrated into plant DNA (Table 2). The following primer sets were used for this purpose:

(1) indicative for the presence of the transposon: (NPTII)

```
(SEQ ID NO:141):    AGGAAGGAATTCCCCCGGATCAGC
(SEQ ID NO:142):    AGGAGCAAGGTGAGATGACAGG
```

(2) indicative for the presence of the T-DNA: (CodA)

```
(SEQ ID NO:143):    GAATCAGCTAATCAGGGAGTGTG
(SEQ ID NO:144):    GCCATGCGCGTTGTTTCACATCG
```

(3) indicative for the presence of a T-DNA carrying a non-excised transposon (the "full donor site"): 637 bp for F1-R1; 848 bp for F 1-R2)

```
P1A (SEQ ID NO:145):    GCATGCTAAGTGATCCAGATG (F1)
P1B (SEQ ID NO:146):    CTGCAGTCATCCCGAATTAG (R1)
```

P1A and P1B amplify the upstream "full donor site", representing the junction between T-DNA and 5'-transposon end, (651 bp) and

```
P2A (SEQ ID NO:147):    GGAATTCGCGTAGACTTATATGGC (F2)
P2B (SEQ ID NO:148):    TGATGACCAAAATCTTGTCATCCTC (R2)
```

P2A and P2B amplify the downstream "full donor site", representing the junction between 3'-transposon and T-DNA.

(4) indicative for the presence of a T-DNA that lost the transposon due to excision (the "empty donor site", 656 bp):

```
P3A (SEQ ID NO:149):GCATGCTAAGTGATCCAGATG (F1)
P3B (SEQ ID NO:150):TGATGACCAAAATCTTGTCATCCTC (R2)
```

Twenty-four plants contained both a full and empty donor site, indicating that the transposon in these plants excised from a stably integrated T-DNA. These plants were not considered for further studies.

In contrast, thirteen contained the transposon and lacked a full donor site. DNA gel blot analysis of these plants demonstrated that eleven of them contained the nptII gene and lacked the codA gene, indicating that they did not contain a stably integrated T-DNA. As shown in Table 2, most of these eleven plants were obtained from the 30-day 5-FC selection experiment.

Eight of eleven plants that lacked any T-DNA or backbone DNA sequences contained a single transposon insert. Because tobacco transformation results, on average, in the integration of two T-DNAs most of which still linked to backbone DNA, the frequency of single-copy and backbone-free transgenic plants is higher for TDTB transformation.

To confirm the integration of excised transposons into plant genomes, we determined the sequence of transposon-plant DNA junctions. Upstream junctions were isolated by (i) digesting DNA of the transgenic lines, (ii) circularizing this DNA using T4 DNA ligase, (iii) employing the resulting DNAs as template for a first PCR using the primer pair TR1 and TD1 (SEQ ID NOs: 151 and 152), and (iv) using the resulting template with the primer pair TR2 and TD2 for a second PCR (SEQ ID NOs: 153 and 154).

Similarly, the primer pair RTR1 and RTD1 (SEQ ID NOs: 155 and 156) was used for first round amplifications of the downstream junction, and the resulting template was used with RTR2 and RTD2 for second round amplifications (SEQ ID NOs: 157 and 158).

Sequence analysis of the junction fragments confirmed that the transposon had in each case excised from the non-integrating T-DNA and integrated into a unique position in plant DNA. As expected, the integrated transposons were flanked by eight-base pair direct repeats, created by duplication of the eight-base pair integration site.

Instead of T-DNAs, it is also possible to use plasmids that can be maintained in *Agrobacterium* and/or *Rhizobium* and contain at least one cleavage site. Instead of the transposon ends employed here, it is also possible to use the termini of other transposable elements that are functional in plants.

These experiments demonstrate that Ds elements can transpose from transferred and non-integrating T-DNAs into the plant genome. By infecting 4,500 potato stem explants, a total of 18 independent transposon transformation events were obtained. Assuming that 25% of explants contained one plant cell that received a T-DNA (1,125 plant cells) and that 75% of these transferred T-DNAs (844) did not integrate into the plant cell genome, the rate of desired transposition events/T-DNA can be estimated at ~0.02. The actual rate may be lower because plant cells are known to often receive more than one T-DNA. It may be possible to increase transposition rates by substituting the promoter that is used to drive the transposase gene. One interesting promoter is the 35S promoter of cauliflower mosaic virus, which was shown to trigger early excision events. Alternatively, the selection system could be optimized to facilitate the identification of plants only containing Ds. For instance, the Ds element could be placed between promoter and nptII gene. Upon transformation, a transient selection on kanamycin could then be used in a similar manner as described previously for marker-free transformation (Rommens et al., Plant Physiol 135: 421-431, 2004) to select for excision events. By inserting a visual marker such as the green fluorescent protein gene within Ds, regenerating shoots could subsequently be screened for the presence of the transposable element.

Given the low transposition frequency from extrachromosomal T-DNAs, it is not surprising that almost all transformed plants contained a single copy of the Ds element. However, our results differ from earlier findings on Ds transposition from plasmid DNA (Houba-Herin et al., Plant J; 6: 55-66, 1994). Although these studies indicated an even lower frequency of transposition from plasmid DNA, transformed plants contained, on average, two copies of the transposed Ds.

Plant 269-112 is unique in that it contains two Ds elements. These elements may have independently transposed from two co-transferred and non-integrating T-DNAs. However, it is also possible that copy number was doubled by the occurrence of a second transposition event from replicated into unreplicated DNA in a similar manner as shown before for Ds transposition in maize.

One group of three plants was found to contain Ds, CodA, and the intermediary 3'-FDS but lack the 5'-FDS and EDS. These plants may have been created by independent integration of both Ds and a truncated T-DNA. Alternatively, the absence of upstream sequences was a consequence of Ds excision attempts. Such activities would result in adjacent deletions that have been reported for both plant and bacterial transposons.

Conventional potato transformation is known to yield frequencies of 20% transformed shoots/explant whereby 35% of shoots contain a single T-DNA copy and 85% contain additional superfluous backbone DNA sequences. Thus, the frequency of desirable plants produced by transposon-based transformation is only three-fold lower than that of conventional methods.

The two-component Ds/Ac-transposase system described here do not represent the only tool kit for transposon-based transformation. Various plant species were shown to contain elements that belong to the Ac/Ds family. Such elements include, for instance, Tip100 of common morning glory (*Ipomoea purpurea*), Pac1 or pearl millet (*Pennisetum glaucum*), and various elements in sugar cane (*Saccharum officinarum*). Furthermore, it may be possible to employ other transposable element systems such as *Arabidopsis* Tag1 and maize En/Spm. All that is needed for transposon-based transformation are (i) the transposon ends that support non-autonomous transposition and (ii) the transposase gene.

Example 8

Enhanced Fidelity of DNA Transfer with Plasmids Carrying the virC Operon

To study whether virC genes influence the frequency and fidelity of the T-DNA transfer, we isolated the entire virC operon (SEQ ID NO. 167) from *Agrobacterium* via PCR approach using virC operon specific primers 5' GTTTAAACAGCTTCCTCCATAGAAGACGG 3' (SEQ ID NO. 168) and 5' TTAATTAATCGTACGGGGGTGTGATGG 3' (SEQ ID NO. 169). The PCR amplified virC operon was cloned into PmeI-PacI sites of the pSIM1008 plasmid DNA backbone that contains Le01 as initial cleavage site and the conventional Left Border of pTiC58 for secondary cleavage. Stably transgenic tobacco plants produced with the resulting plasmid pSIM1026 were analyzed, and the data were compared with those obtained with plasmid pSIM1008. Table 3 shows that the presence of the virC operon increased the frequency of backbone-free transformation more than two-fold.

Example 9

Restriction Sites as Border Alternative

It is possible to employ extremely rare cutting restriction sites instead of borders as sites for DNA cleavage. This method requires the expression of the associated restriction enzyme during plant infection. The restriction sites need to be sufficiently rare to not interfere with growth of *Agrobacterium*. Preferably, the restriction enzyme may be expressed specifically during plant infection by employing, for instance, infection-inducible promoters such as the promoters of *Agrobacterium* vir genes.

The preferred restriction enzymes are homoendonucleases that nick the DNA. One such enzymes is the I-CeuI homing endonuclease from *Chlamydomonas eugametos* (SEQ ID NO 223 for DNA sequence and SEQ ID NO 224 for amino acid sequence). This gene was operably linked to the promoter of the infection-inducible promoter of *Agrobacterium* virC (SEQ ID NO 225) and the terminator of virC. The resulting expression cassette was inserted into the backbone of a binary vector. Instead of a Right Border, this vector contained the 26-nucleotide recognition site for I-CeuI, shown in SEQ ID NO 226. Because homing endonucleases do not have stringently-defined recognition sites, it is possible to alter SEQ ID 226 without losing efficacy.

Effective cleavage can be obtained by limiting internal Magnesium ($Mg^{2+}$) concentrations, which stimulate single-stranded nicking rather than double-stranded cleavage (Turmel et al., Nucleic Acids Res 23: 2519-2525, 1995).

It is also possible to increase the preference for nicking of a specific strand by using a I-CeuI variant that contains, for instance, a alanine residue instead of a threonine at position 122 (T122A) (SEQ ID NO 227). This variant is not lethal in *E. coli*, which facilitates cloning (Turmel et al., Nucleic Acids Res 25: 2610-2619, 1997).

An alternative homoendonuclease system that can be used to cleave transfer DNAs is, for instance I-TevI (Mueller et al., EMBO J. 14: 5724-5735). Binary vectors contain an expression cassette for the I-TevI gene (Genbank accession NP_049849) in their plasmid backbone and a recognition site (SEQ ID 228 or a functional derivative thereof) as right and/or left border.

Tables

TABLE 1

| Plasmid | Backbone-free transformation with transfer DNA | Transformation with transfer DNA still linked to backbone |
|---|---|---|
| Benchmark vector | 39% | 61% |
| Control vector | 26% | 74% |
| pSIM794 | 55% | 45% |
| pSIM795 | 44% | 56% |

TABLE 2

| Treatment | Number of transformed plants | Only carrying the transposon in plant DNA | Carrying at least one T-DNA comprising the transposon at its original position |
|---|---|---|---|
| 10 days on 5-FC | 39 | 0 (0%) | 4 (10%) |
| 20 days on 5-FC | 51 | 3 (6%) | 12 (24%) |
| 30 days on 5-FC | 35 | 9 (26%) | 5 (14%) |
| 45 days on 5-FC | 16 | 1 (6%) | 3 (19%) |
| Total | 141 | 13 (9%) | 24 (17%) |

TABLE 3

Genotypes of transgenic tobacco plants produced with pSIM1026 and pSIM1008

| Plasmid | Integration of sequences between Leo1 and Left Border only (1) | Integration of sequences comprising both the actual transfer DNA and plasmid backbone sequences (2) | Integration of plasmid backbone sequences only (3) |
|---|---|---|---|
| pSIM1008 | 16.9 ± 1.7 | 67.7 ± 5.3 | 21.7 ± 3.7 |
| pSIM1026 | 39.5 ± 4.1 | 51.5 ± 0.8 | 9.2 ± 3.4 |

(1) Visualized using primers
5' TGCTCCTGCCGAGAAAGTAT 3' (SEQ ID NO: 170) and 5' AGCCAACGCTATGTCCTGAT 3' (SEQ ID NO: 171)
(2) Visualized using primers SEQ ID 170 and SEQ ID 171, SEQ ID 172 and SEQ ID 183
(3) Visualized using primers
5' GAATCAGCTAATCAGGGAG 3' (SEQ ID NO: 172) and 5' GCCATGCGCGTTGTTTCACATCG 3' (SEQ ID NO: 183).

TABLE 4

| Vector | Total Transformants | Intended transfer DNA | Intended transfer DNA & Backbone |
|---|---|---|---|
| pSIM580 | 50 | 0% | 100% |
| pSIM108 | 100 | 35% | 65% |
| pSIM1144 | 100 | 29% | 71% |
| pSIM1129 | 0 | 0% | 0% |
| pSIM794 | 100 | 52% | 48% |
| pSIM795 | 100 | 50% | 50% |
| pSIM783 | 67 | 60% | 40% |
| pSIM785 | 70 | 47% | 53% |
| pSIM784 | 200 | 41% | 59% |
| pSIM786 | 100 | 47% | 53% |

SEQUENCE TABLE

| SEQ ID NO: | NAME (if any) | SEQUENCE |
|---|---|---|
| 1 | Rb01 | GTTTACCCGCCAATATATCCTGTCA |
| 2 | Rb02 | AATTACAACGGTATATATCCTGCCA |
| 3 | Rb03 | CATGACAGGAACATATATCCTGTCA |
| 4 | Rb04 | AATTACAACGGTATATATCCTGTCA |
| 5 | Rb05 | CCTGACCACAAGATATATCCTGTCA |
| 6 | Rb06 | CTAGACAAGGGGATATATCCTGTCA |
| 7 | Rb07 | CATTACTTTAGAATATATCCTGTCA |
| 8 | Sy01 | CTTTACACAACAATATATCCTGTCA |
| 9 | Sy02 | GTCTACACAACAATATATCCTGTCA |
| 10 | Sy03 | GTTTAAACAACAATATATCCTGTCA |
| 11 | Sy04 | GTTTACACAACAAGATATCCTGTCA |
| 12 | Sy05 | GTTTACTCAACAATATATCCTGTCA |
| 13 | Sy06 | GTTAACACAACAATATATCCTGTCA |

-continued

SEQUENCE TABLE

| SEQ ID NO: | NAME (if any) | SEQUENCE |
|---|---|---|
| 14 | Sy07 | GTTTACACAACACTATATCCTGTCA |
| 15 | Sy08 | GTTTACACAACAATATATCCTGGCA |
| 16 | Sy09 | GTTTACACAACAATAAATCCTGTCA |
| 17 | Sy10 | GTTTACACAACAATATGTCCTGTCA |
| 18 | Sy11 | GTTTACACAACAATATATGCTGTCA |
| 19 | Sy12 | GTTTACACAACAATATATCGTGTCA |
| 20 | Sy13 | GTTTACACAACAATATATCCAGTCA |
| 21 | extended UI region of pSIM551 | ACGAACGGATAAACCTTTTCACGCCCTTTTAAATATCCGTT ATTCTAATAAACGCTTCTTTTCTCTTAGAGATCTCAAACAAA CATACACAGCGACTTATTCACAACTAG |
| 22 | DI region of pSIM551 | GGGCCCGGTACCCGGGGATCAATTCCCGATCTAGTAACATA GATGACACCGCGCGCGATAATTTATCCTAGTTTGCGCGCTA TATTTTGTTTTCTATCGCGTATTAAAT |
| 23 | potato St01 | GTTTACATCGGTATATATCCTGCCA |
| 24 | primer | YGR CAG GAT ATA TNN NNN KGT AAA C |
| 25 | anchor primer | GAC CAC ACC CGT OCT GTG |
| 26 | *Arabidopsis* At01 | GTTGACATCACGATATATCCTGTCA |
| 27 | CON1 | [A/C/G][A/T][A/T][G/T]AC[A/C/T]N[C/G/T][A/C/G] [A/C/G][A/C/G]ATATATCCTG[C/T]CA |
| 28 | tomato Le01 | CATTACCAACAAATATATCCTGGCC |
| 29 | tomato Le02 | CTCTACCTCTGAATATATCCTGCGG |
| 30 | tomato Le03 | GCATACCTCTGAATATATCCTGCGG |
| 31 | potato St03 | GTTTACCTTAGCATATATCCTGCAT |
| 32 | alfalfa Ms01 | GTATACCTCTGTATACATCCTGCCG |
| 33 | barley Hv01 | ATATACCAAATGATACATCCTGGCC |
| 34 | rice Os01 | ACTTACTCAAGGATATATCCTGGCT |
| 35 | rice Os0 | CACTACAAAAAATATATCCTGCAT |
| 36 | rice Os03 | ATGTACGTATATATATCCTGTGT |
| 37 | wheat Ta01 | ATATACGGAGCAATATATCCTGTCC |
| 38 | Soybean Gm01 | AAAAACTGTTTTATATATCCTGTCA |
| 39 | Soybean Gm02 | AATAACTCTGAAATATATCCTGTGT |
| 40 | Potato St04, | ACCTACCCCAAAATATATCCTGCCT |
| 41 | tomato Le04 | GGAAACTGTCTAATATATCCTGTGA |
| 42 | tomato Le05 | ACCTACCCCAAAATATATCCTGCCC |
| 43 | tomato Le06 | GTTTAGACTTGTATATATCCTGCCC |
| 44 | tomato Le07 | TCTTAGAACTCAATATATCCTGTAC |
| 45 | tomato Le08 | CGTTAACACTGTATATATCCTGTAA |
| 46 | tomato Le09 | GAATTATTTTGCATATATCCTGTAA |
| 47 | tomato Le10 | TTGTTCCTGGCCATATATCCTGCCA |
| 48 | tomato Le11 | GGTACCATGTAGATATATCCTGCTT |

-continued

SEQUENCE TABLE

| SEQ ID NO: | NAME (if any) | SEQUENCE |
|---|---|---|
| 49 | *M. truncatula* Mt01 | GTATACCTCTGTATACCTCCTGCCG |
| 50 | maize Zm01, | GCGTACGCATTTATATATCCTGTGG |
| 51 | Zm01-derived Zm01M1 | GCTTACGCATTTATATATCCTGTGG |
| 52 | *Brassica rapa* Br01 | CCCTACTGTATAATAAATCCTCTAG |
| 53 | tomato Le10 | TTGTTCCTGGCCATATATCCTGCCA |
| 54 | tomato Le1 | GGTACCATGTAGATATATCCTGCTT |
| 55 | tomato Le12 | GTTCCGGTTGACATATATCCTGACA |
| 56 | tomato Le13 | CACTACCGCCTCATAGTTCCTGCCA |
| 57 | soybean Gm01 | TAAAGCAACACCATATATCCTGACA |
| 58 | *M. truncatula* Mt02 | GATTAGACAAATATTTATCCTGCCA |
| 59 | rice Os04 | CTCTACTACCCGAGATGTCCTGGCA |
| 60 | potato St05* | GTTTGACACGACATATATACTGCAA |
| 61 | potato St06* | GTTTACCGTGGCACTTATGTGATGA |
| 62 | potato St07 | CATTACCAACTATTATATCCTGGCC |
| 63 | tomato Le14 | GTTTACTTGAAGATATCAGCTATGT |
| 64 | tomato Le15 | TTCCATACGAAGAGAAGTCCTGTCA |
| 65 | tomato Le16 | TTCTAGCTGCAAATATATCCTGGCT |
| 66 | tomato Le17 | GTTGACATGGATGAATATCCTGTCA |
| 67 | tomato Le18 | GTTCAGCTTAGCATATATCCTGCAT |
| 68 | tomato Le19 | TTCCAGAAGTAGATATATCCTGTTG |
| 69 | tomato Le20 | TGATTGCATCAAATATATCCTGCCA |
| 70 | tomato Le21 | ATCCCCACCCATTTATATCCTGCCA |
| 71 | tomato Le22 | CATCCCCACCATTTATATCCTGCCA |
| 72 | tomato Le23 | GTCAGGAAGTGAATATATCCTGACA |
| 73 | tomato Le24 | GTTTAAACCAATATATATCCTGATT |
| 74 | tomato Le25 | AGTTATAAACTTATATATCCTGTTG |
| 75 | tomato Le26 | CTAAAGTTGTACATAAATCCTGTCT |
| 76 | tomato Le27 | TTCTACACAAAGACAAATCCTGGCG |
| 77 | tomato Le28 | ATTAACAACGTTAGAAGTCCTGGCG |
| 78 | *M. truncatula* Mt03 | CATGACCCTGCAATATGTCCTGTGG |
| 79 | maize Zm02 | AACTTAAAGATAAGAAGTCCTGGCA |
| 80 | oat As01 | CTGTACAATAGGACAAATCCTGTCG |
| 81 | potato St08* | TTTTACCCGTGATATATCCCAGCC |
| 82 | tomato Le29 | GATTGCATCAAATATATCCTGCCA |
| 83 | tomato Le30 | AAGTACCGATGATATATCCTGCGT |

-continued

SEQUENCE TABLE

| SEQ ID NO: | NAME (if any) | SEQUENCE |
|---|---|---|
| 84 | CON2 | [A/C/G]-[A/C/T]-[A/C/T]-[G/T]-A-[C/G]-NNNNNN-A-[G/T]-A-[A/C/T]-[A/G]-TCCTG-[C/G/T]-[A/C/G]-N |
| 85 | Ca01 | CATTACCAACAAATATATCCTGGCC |
| 86 | St02 | CATTACCAACAAATATATCCTGGCC |
| 87 | UI region | CTTAGAGATCTCAAACAAACATACACAGCGACTTATTCACAACTAGTC |
| 88 | overdrive | CAAACAAACATACACAGCGACTTA |
| 89 | UI-derived | TTAGAGATCTCAAACAAACATACACAGCGACTTATTCACAACTAGTAC |
| 90 | UI-derived | AGAGATCTCAAACAAACATACACAGCGACTTATTCACAACTAGTCAAC |
| 91 | UI-like from Agrobacterium | AGAAACAATCAAACAAACATACACAGCGACTTATTCACACGAGCTCAA |
| 92 | UI-like from Agrobacterium | GCCCTTTTAAATATCCGATTATTCTAATAAACGCTCTTTTCTCTTAGG |
| 93 | UI-like from Agrobacterium | TGACGAACTGACGAACTGACGAACTGACGAACTGACGAACTGACGAAC |
| 94 | UI-like from Agrobacterium | TAACAATTGAACAATTGAACAATTGAACAATTGAACAATTGAACAAAC |
| 95 | UI-like from Agrobacterium | TAGACATTGCACATCCAAAGGCAGGCACGTACAAACGAATTTATTTAG |
| 96 | UI-like from Agrobacterium | GAAGGCACGAAGGCACGAAGGCACGAAGGCACGAAGGCACGAAGGCAC |
| 97 | UI-like from Agrobacterium | TCATCACCGCCGTCCTAAACAAACATACCTCCACACAAATTTATCTAC |
| 98 | UI-like from Agrobacterium | AGATCTCAAACAAACATACACAGCGACTTATTCACAACTAGTACCAAC |
| 99 | UI region | TGACGAACTGACGAACTGACGAACTGACGAACTGACGAACTACCAAAC |
| 100 | UI-derived | CTGACGAACTGACGAACTGACGAACTGACGAACTGACGAACTACCAAC |
| 101 | UI-like | TGTCTTTATCTCTTGTTGCCAAAACTGCTCTCGAGTCGAGTCACCAAC |
| 102 | Downstream from right border | GTCAGCATCATCACACCAAAAGTTAGGCCCGAATAGTTTGAAATTAGAAA |
| 103 | Downstream from right border | AACACTGATAGTTTAAACCGAAGGCGGGAAACGACAATCTGATCATGAGCGG |
| 104 | Downstream from right border | AATAACAATCTCATGTTAGGTAATAATATCACCCAATCAACGCGGCGA |
| 105 | Downstream from right border | GCACTAATATAAGAAATGTCCTGTCAGCACTAATATAAGAAATGTC |
| 106 | Downstream from right border | AACCTATTCGTTAATAGGGACGTCGTACCTACTTCCCTTCCAGCGCAGCA |
| 107 | DR domain | [A/C/T]-[A/C]-[A/C/T]-[A/G/T]-[A/T]-T-[A/C]-G-[G/T]-[G/T] |

-continued

SEQUENCE TABLE

| SEQ ID NO: | NAME (if any) | SEQUENCE |
|---|---|---|
| 108 | DI region from potato | GACGTATACACGCATGACTCCCATGATCACTAAATTGATGCCCACACAGGAGACTTATAACCT |
| 109 | DI region from potato | CCCCCCCGTACCCCCGGATCAATTCCCGATCTAGTAACATAGATGAC |
| 110 | DI-region | GGGCCCCGTTCCCGGGGATCAATTCGGCCCCCTACCCGGCGATCAATTCCCGATCTAGTAACATAGATGAC |
| 111 | DI-region | GGCCCCGGTACCCCCACCAGACTCCGATCTACGCCGCCAAATTCAAG |
| 112 | DI-region | CTGAGGACATTCAGAAGATTGGTTATATCCTCTTTCAAGACCCTAAGCAA |
| 113 | DI-region from potato | CACGTATAGAGCCATGTCTCCCGTCATCACTAAATTGATGCCCGCAGAGGCCACTTATAACAT |
| 114 | DI-region from alfalfa | GGGGCCCGGTACCCCTTAGCGCTACCCCGAAAGCGCCGCGGGCAGCCC |
| 115 | repeat | CCCG |
| 116 | AF region | TCTCCATATTGACCATCATACTCATTGCTGATCCATCTACATTTCCCGGACATGAACCCATTTACAATTGAATATATCCTGCCGCCGCTGCCGCTTTGCACCC |
| 117 | AF region | TGAATTCAGTACATTAAAAACGTCCGCAATGTGTTATTAACTTCTCTAAGCGTCAATTTGTTTACACCACAATATATCCTGCCACCAGCCAGCCAACACCTCCCCGACC |
| 118 | AF region | ATCTGGTAATATAGCAAAAACGTGCTCAAAAATCCCTTCAAAGCTCTTGTACTTAGCTCCTTTACACCACAATATATCCTGCCACCCC |
| 119 | AF region | TACATTTTATATTCGATAAAGCATCCGTTAAAACGACTTCGCATGTCCATATCTAATCTGTTTACATCACAATATATCCTGCCACCCAACGACCGACCCCTTCTGGCC |
| 120 | UL domain | A [C/T] T [C/G] A [A/T] T [G/T] [C/T] [C/T] [C/G] A [C/T] [C/T] [A/T] |
| 121 | left border consensus | [A/G] TTTACA [A/C/T] [A/C/T] [A/C/T] [C/G] AATATATCCTCCC [A/G] |
| 122 | | CCN(1-11)CCN(1-11)CCN(1-11)CC |
| 123 | AF region | AAATCTCATTCATAAACCATCCATCCTCTACACTCCACCTCCACTACTTACGTACAATTGTTTACACCACAATATATCCTGCCACCCGATATATTGCCTACGAGCCAGCCAACACCTCCCCCACC |
| 124 | AF region | AAATCTGATTCATAAAGGATCGATCCTCTAGAGTCCACCTGCACTACTTACGTACAATTCTTTACACCACAATATATCCTCCCACCCCTACCACCCACCCAACACCTCCCCCACC |
| 125 | AF region | CTTTACACCACAATATATCCTCCCACCCCTACCACCCACCCAACACCTCCCCCACC |
| 126 | AF region | CTAAAAATAAAACTCAAAATTCAATCAATTAACACAAATATAAATGTAATATAAAATTCTATACCTCTCTATACATCCTCCCCCCAACCTTCCACCCACCTACCACCCACCCAACACCTCCCCACC |
| 127 | AF region | AATGGAGGTAAGTGTTTCTGCTCAGTGCTGATAGATGTAAATATCTCTGTTATGAAGCCGTATACCTCTGTATACATCCTGCCGGGGATGTATACCCTAGGCCAGCCAGCCAACAGCTCCCCGACC |
| 128 | AF region | TGTTGAAGGCTTGGATGTGATTAAGAAGGCCGAGGCTGTTGGATCTAGTTCTTGAAGTTCATTACCAACAATATATCCTGGCCCCCCTAGGAGCCAGCCAACAGCTCCCCGACC |
| 129 | IHF site | [AT] ATCAANNNN [A/G] |

SEQUENCE TABLE

| SEQ ID NO: | NAME (if any) | SEQUENCE |
|---|---|---|
| 130 | search motif | CAGGATATATNNNNNNGTA |
| 131 | extended DNA region of pSIM843B for initial cleavage | GGCTGCACTGAACGTCAGAAGCCGACTGCACTATAGCAGCG GAGGGGTTGGATCAAAGTACTTTGATCCCGAGGGGAACCCT GTGGTTGGCATGCACATACAAATGGACGAACGGATAAACCT TTTCACGCCCTTTTAAATATCCGATTATTCTAATAAACGCT CTTTTCTCTTAGAGATCTCAAACAAACATACACAGCGACTT ATTCACAACTAGTGTATACCTCTGTATACATCCTGCCGGGG CCCGGTACCCGTTAGGGCTAGCCCGAAAGGGCCGCGGGCAG CCCGTTAGCCCGCATAACTGCAGCCCGGG |
| 132 | extended DNA region of pSIM843B for final cleavage | CAGTACTTACGTACATAACAAAAAAAAATTCTATAAATTAT ATATATTTTTCAAATAATTCTTTACACAGTTGATTATCAAA GTAAAAATAAAAGTGAAAATTCAATGAATTAACACAAATA TAAATGTAATATAAAATTGTATACCTCTGTATACATCCTGC CGCCAAGCTTCCAGCCACCTAGGAGCCAGCCAACAGCTCCC CGACCGGCAGCTCGGCACAAAATCACCACTCGATACAGGCA GCCCATCAGTCCGGGACGGCGTCAGCGGGAGAGCCGTTGTA AGGCGGCAGACTTTGCTCATGTTACCGATGCTATTCGGAAG AACGGCAACTAAGCTGCCGGGTTTGA |
| 133 | alternative final cleavage site | CCCGAAAAACGGGACAGGATGTGCAATTGTAATACCGTCAC ACGCGACGCTATTACAATTGCCATCTGGTCAGGGCTTCGCC CCGACACCCC |
| 134 | alternative final cleavage site | CCCGAAAAACGGGACAGGATGTGCAATTGTAATACCGTCAC ACGCGACGCTATTACAATTGCCA |
| 135 | alternative final cleavage site | CCCGAAAAACGGGACAGGATGTGCAATTGTAATACCGTCAC ACGCGACGCTA |
| 136 | alternative final cleavage site | AAAACGGGACAGGATGTGCAATTGTAATACCGTCACACGCG ACGCTATTACAATTGCCATCTGGTCAGGGCTTCGCCCCGAC ACCC |
| 137 | alternative final cleavage site | ACCGAAAAACGGGACAGGATGTGCAATTGTAATACCGTCAC ACGCGACGCTATTACAATTGCCATCTGGTCAGGGCTTCGCC CCGACACCCC |
| 138 | Ac transpasase gene | ATGACGCCTCCGGTTGGAAATAATCCTCCCTCAGGCTCAGC CATAAGATTGGCCAAGTTGATGTCTACCACAAGAGCGCCTT CTACTCGCAAAACAAATTCCGTATTCTCTGCATATGCTCAA GGTATATATTAGAAAAACAGTAGCAATAGCATTAGCATTAC TAATTGGTTGTAGATTGGGAAGCATCATATTGACTGTAGAA TAATACGAAAATCTGTTTATAACAGGGTTGAAAGAAAAG CTGAAGCCTCTTCTAGTCGGATTCAGAATGTACGTGCACGT GCGCGTGGGCATGGATGTGGCCGCACATCACCATCATCATC AACAGCTGAGGCCGAGAGGCATTTTATTCAGAGTGTAAGCA GTAGTAATGCAAATGGTACAGCTACAGATCCGAGTCAAGAT GATATGGCTATTGTTCATGAACCACAACCACAACCACAACC ACAACCAGAACCACAACCACAGCCACAACCTGAACCCGAAG AAGAAGCACCACAGAAGAGGGCAAAGAAGTGCACATCGGAT GTATGGCAGCATTTCACCAAGAAGGAAATTGAAGTGGAGGT CGATGGAAAGAAATACGTTCAGGTATGGGGACATTGCAACT TTCCTAATTGCAAGGCTAAGTATAGGGCTGAGGGTCATCAT GGAACAAGCGGATTTCGAAATCACTTGAGAACATCACATAG TTTAGTTAAAGGTCAGTTGTGTCTAAAAAGTGAAAAGGATC ATGGCAAAGACATAAATCTCATTGAGCCTTATAAGTACGAT GAAGTGGTTAGCCTAAAGAAGCTTCATTTGGCAATAATCAT GCATGAATATCCTTTCAATATTGTAGAACATGAGTACTTTG TTGAGTTTGTTAAGTCTCTGCGCCCTCACTTTCCAATAAAG TCCCGTGTCACTGCTAGAAAATATATCATGGATTTGTATTT GGAAGAAAAAGAAAAGTTGTATGGAAAACTAAAAGATGTTC AGTCTCGCTTCAGTACAACTATGGATATGTGGACATCTTG |
| 139 | 5' transposon end | CAGGGATGAAAGTAGGATGGGAAAATCCCGTACCGACCGTT ATCGTATAACCGATTTTGTTAGTTTTATCCCGATCGATTTC GAACCCGAGGTAAAAAACGAAAACGGAACGAAACGGGATA TACAAAACGGTAAACGGAAACGGAAACGGTAGAGCTAGTTT CCCGACCGTTTCACCGGGATCCCGTTTTTAATCGGGATGAT CCCGTTTCGTTACCGTATTTTCTAATTCGGGATGACTGCA |

-continued

SEQUENCE TABLE

| SEQ ID NO: | NAME (if any) | SEQUENCE |
|---|---|---|
| 140 | 3' transposon end | GTAGACTTATATGGCTTCTTATGTTAGCCAAGAGCCCAAGA CTTATCACTTATGTGCTACATTAAACTATGTGTGCTCCAGA TTTATATGGATTTTATCTATGTTTAATTAAGACTTGTGTTT ACAATTTTTTATATTTGTTTTTAAGTTTTGAATATATGTTT TCATGTGTGATTTTACCGAACAAAAATACCGGTTCCCGTCC GATTTCGACTTTAACCCGACCGGATCGTATCGGTTTTCGAT TACCGTATTTATCCCGTTCGTTTTCGTTACCGGTATATCCC GTTTTCGTTTCCGTCCCGCAAGTTAAATATGAAAATGAAAA CGGTAGAGGTATTTTACCGACCGTTACCGACCGTTTTCATC CCTA |
| 141 | NPTII primer | AGGAAGGAATTCCCCCGGATCAGC |
| 142 | NPTII primer | AGGAGCAAGGTGAGATGACAGG |
| 143 | codA primer | GAATCAGCTAATCACGGAGTGTG |
| 144 | codA primer | GCCATGCGCGTTGTTTCACATCG |
| 145 | P1A primer | GCATGCTAAGTGATCCAGATG |
| 146 | P1B primer | CTGCAGTCATCCCGAATTAG |
| 147 | P2A primer | GGAATTCGCGTAGACTTATATGGC |
| 148 | P2B primer | TGATGACCAAAATCTTGTCATCCTC |
| 149 | P3A primer | GCATGCTAAGTGATCCAGATG |
| 150 | P3B primer | TGATGACCAAAATCTTGTCATCCTC |
| 151 | TR1 primer | ATCGGTTATACGATAACGGTCGGTACG |
| 152 | TD1 primer | ACGAAAACGGAACGGAAACGGGATATAC |
| 153 | TR2 primer | GATTTTCCCATCCTACTTTCATCCCTG |
| 154 | TD2 primer | GTAGAGCTAGTTTCCCGACCGTTTCAC |
| 155 | RTR1 primer | GCACATAAGTGATAAGTCTTGGGCTC |
| 156 | RTD1 primer | CGACCGGATCGTATCGGTTTTCGATTAC |
| 157 | RTR2 primer | CTAACATAAGAAGCCATATAAGTCTAC |
| 158 | RTD2 primer | CGGTAGAGGTATTTTACCGACCGTTAC |
| 159 | upstream junction of plant 1 | ATAGATAAGAGGAGTTTGTTACAAATTTCTACTCCACATTG ATGAGAAATATACTAATGTTATCTCCCCTTCCCTCTATTAG TAGATCTTACTCTATGTTAAAACATGACAAGAAATAGAGAG AGAACTCACACTTTCTTCCTCATCTGCTACTTCTGGTGCCG AAGAAGTTTTACTCAAAGAGTCTAATTTAAGGCAACGAAGC ATGTCCTTTTGTCTCTTGCAAGTATTGCAAGAAGGCAGGAC ACACTTTAAAGAAGTGTTATAAGTCATCCATTTTCCTCTGT CTTCAATTTCTTAAAGACCAAAAGATCCAGTCTTTTGTGTC CATGTTGATAATTTTACTCTAATACTCTTAGCTTCCA |
| 160 | downstream junction of plant 1 | AGCTTCCACATCCCAATTTGGTGATCATTCAGCACATAAAT TTGCTCAGAAGCAATAGGAATATCTCATGTCTCTTCCTTCC AAATAATCAATTCTCACCTAGGTTCAATAATGATGTTTCTT TTAGAGAGATTTCTGACTATGATCATTTTGCAGGTTTAATT AGTACATTTTTTGTAGTTAATTATGTGTTTTTTCATGCATG TTCATCATTGCAATTAGGGGTAGATACTTGAATCTTTTACT TGGGCCACTAGCCACATGACTCCATTTATGGTGTTTATAAG CTATATCAGTGTATATCACATTGTATTTCCATATATCTCAG GTGTACCATATATATCTGTGATTATGTGAAAGACCCCCCTA ATTTGTGTCAAGACTGACAATGCTCTGTCAATCAGTGTAGC AAAAATAAAAATAAAATAAAATCAAGGATTAGTACAACACC ATCCAGGAACCTTTACTAGAAAATTAGTATACCATATGAGT CTTTTACAGTTTGGATCTATCATGGAGTAAAAGAATACATT GCAGATTAGGATTATTCAAAATATGCCTTCTTGCAATCTAC GTTGTGATCAACAGATATA |

-continued

SEQUENCE TABLE

| SEQ ID NO: | NAME (if any) | SEQUENCE |
|---|---|---|
| 161 | upstream junction of plant 2 | ATTCTCACCAAAAATTGAGGTGATTAGATAAAAAAGATCA<br>ATTTGTTAAGACCAGCAGCAGCTCTTCAGTACCATTTCATG<br>TCTTAACAGGACATATATATATATATATAGATATAGAGAGA<br>GAAAGTGGGCAAGACTTGATTTTTATAGATCTAGAGAGAGA<br>AAAGGAGAGTTGGG |
| 162 | downstream junction of plant 2 | GAGTTGGGGAGAAAAGAAGGGATTTTTACAGATCTAGAGA<br>GAGAAAGACTTGATTCTTCCTATTTTCTCTTCACCATTTCC<br>TATGTTTTCTCTCCCTCTCTTTTCTCTTTCTTGATTTCTCT<br>ATAAATTTTCACTCATTAGTATATTCATCACTCTCAATTTA<br>CCTTTTATATAAAAATAAAAACAATAAAAATTACTAAATAC<br>ATTTAATTTTAATTATAAATAGAAATTATTACACTATTGAT<br>TTTTTATTTGACTTATTTATTTATTTTAGTCTATTCGAAAA<br>ATATGTCTTTTTCGTTTTCTAATAACTCTTTCATTTTAGTC<br>TTTTCCATTTAATATTACAAAATTTAAAAAAATGCATTTTG<br>GTACCTTTTTAAGATTACAAAATTTGAATATATTATTTACT<br>TTATTAAATTACGCATTTAATCAAAACAAAACAATCAAAAT<br>GAAAGCATTTTGGTACCTTCTAGAATACGTATATTTAATTT<br>GAAATTACAAAATTTGAATATATTCTTTATTTTGTTAAATT<br>ACGTATTTAGTCAAAACAGGACAATAAAAAAAAACGAAAGG<br>AGTAATTACTAATACAATAACATTTTCACTAAAATTAAAAT<br>TAAAGAAAAAAACGATTTTGGTACCTTCTAG |
| 163 | upstream junction of plant 3 | TGTGATTTAGGAACGTAAGATGACTTTGCAAGCATTGTCTT<br>CAAATGGCATAAATCTAACATTCAAAATTAAGTCTATTTTT<br>AAACAATAAAAATACATGAGATTTGCAATTTATAAGTCAAC<br>GTTGTCATATAACCCATTAGTTCGGTTTTAAGGATATGAAT<br>AGAGGTTTGAAACGTGTTGCAAATGCTCTCAACTATGGACA<br>TAACCCAGTACCCATGTCAGCACTAAGGACCACCGGGAAAC<br>ACCCCCCGGAACCATCGGAACCACCAGATACCACTAGCTAC<br>ATGATGGAGGACCCAGAATCGAATCAGAGCTTTAAGGATAT<br>TCTCCTGAACAAAAATAAGGAGATAAATCAACTACACCACC<br>CTACCGGAAC |
| 164 | downstream junction of plant 4 | ACCGGAACTGGAACAGCAGGATCATACAGAGGACCTTGACA<br>TGGACTCCATCCAACTATCGACAGAGGACAAGCAACAAATT<br>TACCAACCGTGGAACCTCTCTGTGATAGTAAAGGTATTTGG<br>AAAAAAATCGCCCACGCATACTTGAAAAACAAGTTGGTTGA<br>TCTATGGAAGCGATCAGAACCTCTAACACTGATAGATTTTG<br>GCTGTGAATACTTTATATTGCAAAATTCAATAATCCAACCA<br>GCCTACATAACTCCCTCCATGAGGGTCCGTGGTTCATCGCA<br>GGAAACTTCCTGTTAGTAAAAAAAATGGGAGCCAAACTTTG<br>TGCCAGACACATCAACACTCACCCATACAACGATATGGGCA<br>AGGCTGCTGCAACTCCCAGCGGAGTTCTATGACAGGCAAAT<br>ACTAGAAAAGGTAGGGGGAAACCTCGGGTCCCTCCTAAAAA<br>TTGATACCTGCACCTCTGCTGCACTAAGAGGACGTTATGCA<br>CGCATACAGGTTCAGCTAGAGAATCCAGTCAAGACGACGGT<br>CAAAATTGGAAACCATGTTCAAAAAGTGGTATACAGAGGGGG<br>ACAAAATCCTTTGCACAGAATGTGGGAGACTCGGGAACACC<br>TTATTGACCTCATCCAGGATTTTGAGATGATGGGTACACGA<br>TTATAAAAAGTTGATCTATGATTTAAATTTGATCGGTTTA<br>ATATTTAAATTTTTACTACTAAAAACCGTTAAATTTTAAA<br>ATTATAGGTCTAAAATTAATTCTTATATATATATATATACA<br>CACACCAATTACCACTTAGAGAAGTGTTATCTAATTTTAGA<br>AAGAAAAATAAAACAAGATAAATATAAATTTCAAATTTCTA<br>ACCTCGTGGAGAGAGGTGCACCCAGTCATAATCGCATTATG<br>TGATACTTCAAGTG |
| 165 | upstream junction of plant 4 | AGATCGACTGAGAAGTAGCTGGAAACATCATGAGTGGCAG |
| 166 | downstream junction of plant 4 | AGTGGCAGAAGTGGAAGAGATAAAACTCATGATGATTGTAA<br>TGAGGGTGGTGGACAAGATGAATCTGGTGCCCAAAACAACA<br>AAAATACTAATGCCAACAAAAGATCAGGACCAACGGTGCCA<br>CCTAAAAGGGGAAGCATAGCAAAACAGATAGTACGAGATTT<br>AAAGGATACATCAAGCTCTCTGAGTACTGTATTCACATTGT<br>TTTTCTTTAACTTCCTTCTCATGGCGATTATATCGACAAAT<br>TATGAGAACAAAATATAGGAAGTTTACAACATTGAGGAAAG<br>CAAGTAACCAGTAGTAATAATCTAAATGACCATTGTTAATA<br>TTACTTGACAACCAGCTAACTCCACCTCCATATGAAGTAAC<br>ACTATCCACAACATTCACTAAAACACTCCCAAAAAAGCCAG<br>CTACAGACATTCCAAGTGTGAAAATAGCCACAACAAAACTA<br>GACATGCTTTTGGAAGTTCAGAGTAAAGGAACTCTACCAA |

SEQUENCE TABLE

| SEQ ID NO: | NAME (if any) | SEQUENCE |
|---|---|---|
| | | TCCGATTGCATTGAAAGCATCAGCTAGTCCAAGAAGCACGT ACTGTGGCACGAACCACATAGCCGACATGTTTATATTTAGA CTGTCTTGTGGATCTTTCTGATCAATTGCTATGCCCCGCCT TATGCCTTCTGTTATCGCTGAAAGTACCATCG |
| 167 | virC2 region | TTAACTCCGCTCGATATCGATGAAGCATTGTCGACCTACCG CTATGTCATTGAACTGCTGCTGAGCGAGAACTTGGCAATTC CGACAGCCGTATTGCGCCAACGCGTGCCGGTTGGTCGATTG ACCACATCGCAGCGCGCGATGTCGGACATGCTCGCAAGCCT TCCAGTTGTACAGTCTCCCATGCACGAGAGAGACGCATTTG CCGCGATGAAGGAACGTGGCATGTTGCATCTCACATTGCTG AATATGAGAACCGATCCGACAATGCGCCTCCTCGAGCGGAA TCTCAGAATCGCCATGGAGGAACTCGTCACTATCTCCAAAT TGGTTAGCGAAGCCTTGCAGGGGTGAAGATGGGAATTCGCA AACCCGCTTTGTCTGTCGGGGAGGCCAGGCGGCTTGCCGCC GCTCGACCCGAAATCGTCCATCCTTCTTTGCCTGTTGCCAC CCAAAACTCGACCCTGCCGCAGCCGCCTGAAAATCTCGACG AGGAAGATCGACGACCTGCCCCAGCCACCGCCAAGCGTTGT CACAGCTCTGATCAGCAATCGATGCTGACCGTGGATGCTTT GAGTTCGACGACAGCGCCAGAAAGGATCCAGGTCTTCCTTT CAGCGCGCCCGCCCGCGCCTGAAGTATCGAAGATATATGAC AACCTGATCCTGCAATACAGTCCTTCCAAGTCGCTACAAAT GATCTTGCGCCGTGCGCTTGGCGATTTTGAAAACATGCTGG CGGATGGATCGTTTCGTGCGGCTCCGAAGAGTTATCCGATC CCTCACACAGCTTTCGAAAAATCAATCATCGTTCAGACCTC CCGCATGTTCCCGGTCTCGCTAATAGAAGCCGCTCGCAATC ACTTTGATCCATTGGGATTGGAGACCGCCCGGGCTTTCGGC CACAAGCTGGCTACCGCAGCGCTTGCATGTTTCTTTGCTCG GGAGAAGGCAACGAACAGCTGATCTCTCAAAAGATAGGACC CATCCAATCACTCCGGAGTGCTGAGTTTTTCGGATAGTACC GAGGAAAGGCAGCTTTGCCAAGCCGCATAGCAATCTGCTCA CGTTGGGAACAGATTGCTAAAGGCGAAATGCACCTCTACCT CAGGCCGCCATCACACCCCCGTACGA |
| 168 | virC primer | GTTTAAACAGCTTCCTCCATAGAAGACGG |
| 169 | virC primer | TTAATTAATCGTACGGGGGTGTGATGG |
| 170 | primer | TGCTCCTGCCGAGAAAGTAT |
| 171 | primer | AGCCAACGCTATGTCCTGAT |
| 172 | primer | GAATCAGCTAATCAGGGAG |
| 173 | human AC027708 | TGGCAGGATATATACATATGTACAC |
| 174 | human AC024192 | CTGCAGGATATATTTCTCAGTAAAC |
| 175 | human AC003685 | TGCCAGGATATATACATGGCTAATG |
| 176 | human AL390883 | GGCCAGGATATATTACCCAGTAATT |
| 177 | human AC022858 | AGGCAGGACTTCTGTGTATGTTAAC |
| 178 | mouse AC110541 | AGCCAGGACTTAATGTGGTGTAAAC |
| 179 | mouse AC132685 | TGGCAGGATATATATCTTGGTAAAT |
| 180 | rat AC096051 | TGGCAGGATATATGGCATTGTCATT |
| 181 | Neurospora BX897673 | ATACAGGATATATAGGTAGGTAAAG |
| 182 | *Saccharomyces* AJ316068 | AGACAGGATATATTGGAAGGTATTC |
| 183 | primer | GCCATGCGCGTTGTTTCACATCG |

-continued

SEQUENCE TABLE

| SEQ ID NO: | NAME (if any) | SEQUENCE |
|---|---|---|
| 184 | UF region of pSIM108 | TCCTTCATAGCTACACTTTCTAAAGGTACGATAGATTTTGG ATCAACCACACACACTTC |
| 185 | UF region of pSIM843B | GTAAAAAATAAAAGTGAAAATTCAATGAATTAACACAAATA TAAATGTAATATAAAATT |
| 186 | UF region ofpSIM781 | TGTTGAAGGCTTGGATGTGATTAAGAAGGCCGAGGCTGTTG GATCTAGTTCTTGAAGTT |
| 187 | C-clusters of pSIM831 | CCACAATATATCCTGCCACCGGATATATTGCCTAGGAGCCA GCCAACAGCTCCCCGACC |
| 188 | C-clusters of pSIM843 | CCTCTGTATACATCCTGCCGCCAAGCTTCCAGCCACCTAGG AGCCAGCCAACAGCTCCCCGACC |
| 189 | modified *Brassica rapa* cleavage site Br01M1 | CCCTACTGTATAATAAATCCTGTAG |
| 190 | modified *Brassica rapa* cleavage site BrM2 | CTCTACTGTATAATAAATCCTGTCG |
| 191 | approximate part of alternative final cleavage site that is transferred to plant cell | CCCGAAAAACGGGA |
| 192 | *Arabidopsis* sequence resembling SEQ ID 191 | ACCGAAAAACGGGA |
| 193 | Maize Zm03 | GCGTACGCATTTATATATCCTGTGG |
| 194 | Zm03-modified cleavage site Zm03M1 | GCTTACGCATTTATATATCCTGTGG |
| 195 | Gm01-derived Gm01M1 | AAATACTGTTTTATATATCCTGTCA |
| 196 | Gm02-derived Gm02M1 | AATTACTCTGAAATATATCCTGTGT |
| 197 | *Brassica rapa* Br02 | TGGAACTGTTCTATATGTCCTGTCA |
| 198 | Br02-derived Br02M1 | AGGAACTGTTCTATATGTCCTGTCA |
| 199 | UI region of SEQ ID: 87 | CTTAGAGATCTCAAACAAACATACACAGCGACTTATTCACA ACTAGTC |
| 200 | UI-like region of SEQ ID: 91 | AGAAACAATCAAACAAACATACACAGCGACTTATTCACACG AGCTCAA |
| 201 | UI-like region of SEQ ID: 92 | GCCCTTTTAAATATCCGATTATTCTAATAAACGCTCTTTTC TCTTAGG |
| 202 | UI-like region of SEQ ID: 93 | TGACGAACTGACGAACTGACGAACTGACGAACTGACGAACT GACGAAC |
| 203 | UI-like region of SEQ ID: 94 | TAACAATTGAACAATTGAACAATTGAACAATTGAACAATTG AACAAAC |

SEQUENCE TABLE

| SEQ ID NO: | NAME (if any) | SEQUENCE |
|---|---|---|
| 204 | UI-like region of SEQ ID: 95 | TAGACATTGCACATCCAAAGGCAGGCACGTACAAACGAATTTATTTAG |
| 205 | UI-like region of SEQ ID: 96 | GAAGGCACGAAGGCACGAAGGCACGAAGGCACGAAGGCACGAAGGCAC |
| 206 | UI-like region of SEQ ID: 97 | TCATCACCGCCGTCCTAAACAAACATACCTCCACACAAATTTATCTAC |
| 207 | UI region of SEQ ID: 98 | AGATCTCAAACAAACATACACAGCGACTTATTCACAACTAGTACCAAC |
| 208 | UI region of SEQ ID: 99 | TGACGAACTGACGAACTGACGAACTGACGAACTGACGAACTACCAAAC |
| 209 | UI region of SEQ ID: 100 | CTGACGAACTGACGAACTGACGAACTGACGAACTGACGAACTACCAAC |
| 210 | UI region of SEQ ID:101 | TGTCTTTATCTCTTGTTGCCAAAACTGCTCTCGAGTCGAGTCACCAAC |
| 211 | UF-like region of SEQ ID: 116 | TCTCCATATTGACCATCATACTCATTGCTGATCCATGTAGATTTCCCGGACATGAAGCC |
| 212 | UF-like region of SEQ ID: 117 | TGAATTCAGTACATTAAAAACGTCCGCAATGTGTTATTAAGTTGTCTAAGCGTCAATTT |
| 213 | UF-like region of SEQ ID: 118 | ATCTGGTAATATAGCAAAAACGTGCTCAAAAATCGCTTCAAAGCTCTTGTACTTAGCTC |
| 214 | UF-like region of SEQ ID: 119 | TACATTTTATATTCGATAAAGCATGCGTTAAAACGACTTCGCATGTCCATATCTAATCT |
| 215 | AF-like region of SEQ ID: 116 | CCTGCCGCCGCTGCCGCTTTGCACCC |
| 216 | AF-like region of SEQ ID: 116 | CCTGCCACCAGCCAGCCAACAGCTCCCCGACC |
| 217 | AF-like region of SEQ ID: 116 | CCACAATATATCCTGCCACCCC |
| 218 | AF-like region of SEQ ID: 116 | CCTGCCACCCAAGGAGCGACGCCTTCTGGCC |
| 219 | oriT region of Agrobacterium pTiC58 | GGTACCGGTCCGGCTCTCTCGGCTTGTCTCTTTCCGGTCGCCGAGCCCTTGCCGCCACGAAACCGTTTGGCGAGTTCCTCGAAGGCTGCCTGAAGCTGTGACTCCTCGATGTCGATTTCACCAAGACCGGCCTTCAACGCAATCCTGCCGATTCGTTCGGCCTCGCGTGTTTCGGCCTGTTTCAGCTGGTCCTGCAATCTGGCAATTTCTTCCCTGATCTTCGATGATGGTTTCTTCATTCCGGTCGCATCTCCCTGGAAATCCTGCGGCGTCTGTTCCGCTGCAAGATTTCCTCAAAAGCACTTCGGAAGGAATGTGCAGATCTGCACGTCGGCAAAGCCGACACTTTGGAGGATGATCCCGCCGCTCGACGAGAGCGGATCCAAGGGCGCAATTATACGTCGCTGACGCGACGCCTTGCGTAGGGGGCCAAACAGGGGCCCACTGTGGCCTCACCGCTCCCGACGAACGACGTTCAAACGGGAGCTTTTACCGCCGTGGCCATCGCCCACTTCTCAGCCAGCATCGTCAGCCGCGGCGACGGCCGCAGCGTGGTGCTGTCTGCGGCCTACCAGCACTGCGCGAAGATGGAATACGAGCGCGAGGCCCGCACCATCGACTACACCCGCAAGCAAGGGCTGGTGCATCAGGAATTC |
| 220 | Double oriT | GGGGTGTCGGGGCGAAGCCCTGACCAGATGGCAATTGTAATAGCGTCGCGTGTGACGGTATTACAATTGCACATCCTGTCCCGTTTTTCGGGTAAAGCTTGGGGTGTCGGGGCGAAGCCCTGACCAGATGGCAATTGTAATAGCGTCGCGTGTGACGGTATTACAATTGCACATCCTGTCCCGTTTTTCGGGCTACAGATGAACAAAAACAAAACAGAAATTGATTTCTGAGAAGAAGAAGAAGAAGAGGAAGCATTCACATTTATCACCGATTACAGTAGGGTCAAATTCAGTAGGCAAGAGAATCAAAATCAGAATAGATGAGATG |

SEQUENCE TABLE

| SEQ ID NO: | NAME (if any) | SEQUENCE |
|---|---|---|
| | | AGATATGAAACAACGTTTATACACCATAACACGATTCATAA TAGAATGTAGGGAAACATGCATGAAATCAGAAATAATTGGA GGAGATGAGTAAAAGTTACCATGGTAC |
| 221 | oriT with plant border alternative | GGGGTGTCGGGGCGAAGCCCTGACCAGATGGCAATTGTAAT AGCGTCGCGTGTGACGGTATTACAATTGCACATCCTGTCCC GTTTTTCGGGCTCGAGAGTGGTGATTTTGTGCCGAGCTGCC GGTCGGGGAGCTGTTGGCTGGCTGGAAGCTTTGGCAGGATA TATTTGTTGGTAATGGAAGTGTGTGTGGTTGATCCAAAATC TATCGTACCTTTAGAAAGTGTAGCTATGAAGGATAGTCTCA CTTATGAAGAACTACCTATTGAGATTCTTGATCGTCAGGTC CGAAGGTTGAGAAAAATAGAAGTCGCTTCAGTTACGGCTTT GTGGAGGAGTAAGGGTAC |
| 222 | oriT with plant border alternative | GGGGTGTCGGGGCGAAGCCCTGACCAGATGGCAATTGTAAT AGCGTCGCGTGTGACGGTATTACAATTGCACATCCTGTCCC GTTTTTCGGGCTCGAGAGTGGTGATTTTGTGCCGAGCTGCC GGTCGGGGAGCTGTTGGCTGGCTGGAAGCTTTGGCAGGATA TATACCGGTGTAAACGAAGTGTGTGTGGTTGATCCAAAATC TATCGTACCTTTAGAAAGTGTAGCTATGAAGGATAGTCTCA CTTATGAAGAACTACCTATTGAGATTCTTGATCGTCAGGTC CGAAGGTTGAGAAAAATAGAAGTCGCTTCAGTTACGGCTTT GTGGAGGAGTAAGGGTAC |
| 223 | I-CeuI homoendonuclease gene | ATGTCAAACTTTATACTTAAACCGGGCGAAAAACTACCCCA AGACAAACTAGAAGAATTAAAAAAAATTAATGATGCTGTTA AAAAAACGAAAAATTTCTCAAAATACTTGATTGACTTAAGA AAACTTTTTCAAATTGACGAAGTCCAAGTAACTTCTGAATC AAAACTCTTTTTAGCTGGTTTTTTAGAAGGTGAAGCTTCTC TAAATATTAGCACTAAAAAGCTCGCTACTTCTAAATTTGGT TTGGTGGTTGATCCTGAATTCAATGTGACTCAACATGTCAA TGGGGTTAAAGTGCTTTATTTAGCATTAGAAGTATTTAAAA CAGGGCGTATTCGTCATAAAAGTGGTAGTAATGCAACTTTA GTTTTAACTATTGACAATCGTCAAAGTTTGGAAGAAAAAGT AATTCCTTTTTATGAACAATATGTTGTTGCCTTCAGTTCTC CAGAAAAAGTCAAACGTGTAGCTAATTTTAAAGCTTTGTTA GAATTATTTAATAATGACGCTCACCAAGATTTAGAACAATT GGTAAACAAAATCCTACCAATTTGGGATCAAATGCGTAAAC AACAAGGACAAAGTAACGAAGGCTTTCCTAATTTAGAAGCA GCTCAAGACTTTGCTCGTAATTATAAAAAAGGTATAAAGTA G |
| 224 | I-CeuI homoendonuclease | MSNFILKPGEKLPQDKLEELKKTNDAVKKTKNFSKYLIDLR KLFQIDEVQVTSESKLFLAGFLEGEASLNISTKKLATSKFG LVVDPEENVTQHVNGVKVLYLALEVFKTGRIRHKSGSNATL VLTIDNRQSLEEKVIPFYEQYVVAFSSPEKVKRVANFKALL ELFNNDAHQDLEQLVNKILPIWDQMRKQQGQSNEGFPNLEA AQDFARNYKKGIK |
| 225 | virC promoter | AGCTTCCTCCATAGAAGACGGAAAGATCTGAACCTGCCCCG CCGTAGCATTTCCTCGTCGTGGCAGATGGGAATCTAGCCAT ATACAAAACGAAATCAAGAACACATAAGGGATATTTATTTT TATATTATTACAATTGAAATTATATTACAATAAAATTGAAA TATAAAGTCAGGTAATTACTACATTACTTATGAATTATCGC AAAATCATACACACAAATAAAAGTACAGACACACTTCCGCT TCACAAAATCGACAGGATAAGGA |
| 226 | Recognition site for I-Ceu-I | TAACTATAACGGTCCTAAGGTAGCGA |
| 227 | I-CeuI homoendonuclease variant | MSNFILKPGEKLPQDKLEELKKINDAVKKTKNFSKYLIDLR KLFQIDEVQVTSESKLFLAGFLEGEASLNISTKKLATSKFG LVVDPEFNVTQHVNGVKVLYLALEVFKTGRIRHKSGSNATL VLAIDNRQSLEEKVIPFYEQYVVAFSSPEKVKRVANFKALL ELFNNDAHQDLEQLVNKILPIWDQMRKQQGQSNEGFPNLEA AQDFA |
| 228 | I-TevI recognition site | AACGCTCAGTAGATGTTTTCTTGGGTCTACCGTTTAA |

What is claimed is:

1. A transfer-DNA, comprising a first polynucleotide positioned between, operatively linked to, and delineated by, a second and third polynucleotide, wherein (i) the first polynucleotide comprises at least one promoter operatively linked to a desired polynucleotide, (ii) the second polynucleotide is (a) a transfer-DNA Right Border, (b) a plant-derived transfer-DNA border sequence, or (c) a homoendonuclease recognition site, and (iii) the third polynucleotide is an origin of conjugative plasmid DNA transfer that contains a cleavage site and functions as a transfer-DNA Left Border replacement.

2. The transfer-DNA of claim 1, wherein the origin of conjugative plasmid DNA transfer is a sequence from *Agrobacterium, Rhizobium, Corynebacterium, Escherichia,* or *Klebsiella*.

3. The transfer-DNA of claim 1, wherein the origin of conjugative plasmid DNA transfer comprises a sequence with at least 70% identity to at least a fragment of the sequence depicted in SEQ ID NO: 219, and which is a functional origin of transfer.

4. The transfer-DNA of claim 1, further comprising a fourth polynucleotide, wherein the fourth polynucleotide (i) is positioned between the second and third polynucleotide, (ii) can mediate either single-stranded or double-stranded DNA cleavage, and (iii) is not identical in nucleotide sequence to an *Agrobacterium* transfer-DNA border sequence or to a plant-derived transfer DNA border sequence.

5. The transfer-DNA of claim 4, wherein the fourth polynucleotide is an origin of conjugative DNA transfer.

6. The transfer-DNA of claim 5, wherein the first polynucleotide is positioned between two origins of conjugative DNA transfer.

7. A plasmid, comprising the transfer-DNA of claim 1.

8. The plasmid of claim 7, further comprising in its backbone one or more of an expression cassette for (i) a cytokinin gene or (ii) a homoendonuclease gene.

9. The plasmid of claim 7, wherein the cassette comprises at least one recognition site for a homoendonuclease and wherein the plasmid backbone comprises at least one expression cassette for a homoendonuclease gene.

10. The plasmid of claim 9, wherein the recognition site is a recognition site for an I-CeuI or I-TevI homoendonuclease enzyme, and wherein the homoendonuclease gene is selected from the group consisting of the I-CeuI gene, a modified I-CeuI gene, wherein the modification results in a T122A modification of the encoded protein, or a I-TevI gene.

11. A method for transforming a plant cell, comprising contacting a plant cell with a bacterial strain containing the plasmid of claim 7, wherein the bacterial strain is a strain selected from the group consisting of *Agrobacterium tumefaciens, Agrobacterium rhizogenes, Rhizobium trifolii, Rhizobium leguminosarum, Phyllobacterium myrsinacearum, SinoRhizobium meliloti,* and *MesoRhizobium loti*.

12. A cassette, comprising a first polynucleotide, which comprises a non-autonomous transposable element, positioned between a second and third polynucleotide, wherein the second and third polynucleotides can mediate either single-stranded or double-stranded DNA cleavage, wherein the cassette is not a plant transformation cassette.

13. The cassette of claim 12, wherein the ends of the non-autonomous transposable element share at least 70% sequence identity with the ends of an element selected from the group of known plant transposable elements.

14. The cassette of claim 13, wherein the sequence of the transposable element comprises a sequence with at least 70% identity to at least part of the sequence depicted in SEQ ID NO: 138.

15. The cassette of claim 12, further comprising a transposase gene that (i) is operably linked to regulatory elements so that it can be expressed and (ii) encodes a protein that mediates excision of the non-autonomous transposable element.

16. An expression system, comprising (1) the cassette of claim 12, and (2) a second cassette, which comprises (i) a first polynucleotide positioned between (ii) a second polynucleotide and (iii) third polynucleotide, wherein (a) both the second and third polynucleotide can mediate single-stranded or double-stranded DNA cleavage and are selected from the group consisting of an *Agrobacterium* border sequence, a plant-derived border sequence, an endonuclease recognition site sequence, and an origin of DNA transfer sequence, and (b) the first polynucleotide comprises a transposase gene that (i) is operably linked to regulatory elements so that it can be expressed and (ii) encodes a protein that mediates excision of the non-autonomous transposable element from the cassette of claim 12.

17. The cassette of claim 12, wherein the non-autonomous transposable element further comprises a selectable marker gene.

18. The cassette of claim 17, wherein the selectable marker gene is the neomycin phosphotransferase gene.

19. The cassette of claim 12, wherein the ends of the non-autonomous transposable element are at least 70% identical to the ends of the maize Ac element.

20. The cassette of claim 12, further comprising (1) a right border sequence, a plant-derived border sequence, or an endonuclease recognition site sequence, (2) a non-autonomous transposable element comprising (a) a desired polynucleotide, and (b) a selectable marker gene, and (3) a left border sequence, or a plant-derived border sequence or an origin of conjugative DNA transfer sequence.

21. The cassette of claim 12, further comprising (1) a right border sequence, a plant-derived border sequence, or an endonuclease recognition site sequence, (2) a non-autonomous transposable element inserted between a promoter and a selectable marker gene, and (3) a left border sequence, or a plant-derived border sequence or an origin of conjugative DNA transfer sequence.

22. The cassette of claim 21, wherein the transposable element comprises a visual or selectable marker gene.

23. A method for transforming a plant cell with a non-autonomous transposable element, comprising contacting a plant cell with a bacterial strain containing a plasmid that contains the transformation cassette of claim 12, wherein the bacterial strain is a strain selected from the group consisting of *Agrobacterium tumefaciens, Agrobacterium rhizogenes, Rhizobium trifolii, Rhizobium leguminosarum, Phyllobacterium myrsinacearum, SinoRhizobium meliloti*, and *MesoRhizobium loti*, and wherein the transformed plant cell that not contain any sequences from the cassette other than the transposable element.

24. A method for transforming a plant cell with a non-autonomous transposable element, comprising contacting a plant cell with either (i) one bacterial strain containing two plasmids, one of which contains a first cassette of claim 16 and the other one containing the second cassette, or (ii) two bacterial strains, one of which contains a plasmid with the first cassette of claim 16 and the other one contains a plasmid with the second cassette of claim 16, wherein the bacterial strain(s) is/are selected from the group consisting of *Agrobacterium tumefaciens, Agrobacterium rhizogenes, Rhizobium trifolii, Rhizobium leguminosarum, Phyllobacterium myrsinacearum, SinoRhizobium meliloti*, and *MesoRhizobium loti*, and wherein the transformed plant cell that not contain any sequences from the cassette other than the transposable element.

25. The transfer-DNA of claim 1, wherein the second polynucleotide is a transfer-DNA Right Border.

26. The transfer-DNA of claim 1, wherein the second polynucleotide is a plant-derived transfer-DNA border sequence.

27. The transfer-DNA of claim 1, wherein the second polynucleotide is a homoendonuclease recognition site.

* * * * *

SEQUENCE LISTING

<160> NUMBER OF SEQ ID NOS: 230

<210> SEQ ID NO 1
<211> LENGTH: 25
<212> TYPE: DNA
<213> ORGANISM: Agrobacterium tumefaciens

<400> SEQUENCE: 1
gtttacccgc caatatatcc tgtca                                              25

<210> SEQ ID NO 2
<211> LENGTH: 25
<212> TYPE: DNA
<213> ORGANISM: Agrobacterium tumefaciens

<400> SEQUENCE: 2
aattacaacg gtatatatcc tgcca                                              25

<210> SEQ ID NO 3
<211> LENGTH: 25
<212> TYPE: DNA
<213> ORGANISM: Agrobacterium rhizogenes

<400> SEQUENCE: 3
catgacagga acatatatcc tgtca                                              25

<210> SEQ ID NO 4
<211> LENGTH: 25
<212> TYPE: DNA
<213> ORGANISM: Agrobacterium vitis

<400> SEQUENCE: 4
aattacaacg gtatatatcc tgtca                                              25

<210> SEQ ID NO 5
<211> LENGTH: 25
<212> TYPE: DNA
<213> ORGANISM: Agrobacterium rhizogenes

<400> SEQUENCE: 5
cctgaccaca agatatatcc tgtca                                              25

<210> SEQ ID NO 6
<211> LENGTH: 25
<212> TYPE: DNA
<213> ORGANISM: Agrobacterium rhizogenes

<400> SEQUENCE: 6
ctagacaagg ggatatatcc tgtca                                              25

<210> SEQ ID NO 7
<211> LENGTH: 25
<212> TYPE: DNA
<213> ORGANISM: Agrobacterium rhizogenes

<400> SEQUENCE: 7
cattacttta gaatatatcc tgtca                                              25

<210> SEQ ID NO 8
<211> LENGTH: 25
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 8
ctttacacaa caatatatcc tgtca                                              25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtctacacaa caatatatcc tgtca                                              25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtttaaacaa caatatatcc tgtca                                              25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtttacacaa caagatatcc tgtca                                              25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtttactcaa caatatatcc tgtca                                              25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gttaacacaa caatatatcc tgtca                                              25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtttacacaa cactatatcc tgtca                                              25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtttacacaa caatatatcc tggca                                              25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtttacacaa caataaatcc tgtca                                              25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtttacacaa caatatgtcc tgtca                                              25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtttacacaa caatatatgc tgtca                                              25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtttacacaa caatatatcg tgtca                                              25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
gtttacacaa caatatatcc agtca                                          25

<210> SEQ ID NO 21
<211> LENGTH: 109
<212> TYPE: DNA
<213> ORGANISM: Artificial Sequence
<220> FEATURE:
<223> OTHER INFORMATION: Description of Artificial Sequence: Synthetic
      UI region of pSIM551 nucleotide sequence

<400> SEQUENCE: 21
acgaacggat aaaccttttc acgcccttttt aaatatccgt tattctaata aacgctcttt    60
tctcttagag atctcaaaca aacatacaca gcgacttatt cacaactag               109

<210> SEQ ID NO 22
<211> LENGTH: 109
<212> TYPE: DNA
<213> ORGANISM: Artificial Sequence
<220> FEATURE:
<223> OTHER INFORMATION: Description of Artificial Sequence: Synthetic
      DI region of pSIM551 nucleotide sequence

<400> SEQUENCE: 22
gggcccggta cccggggatc aattcccgat ctagtaacat agatgacacc gcgcgcgata    60
atttatccta gtttgcgcgc tatattttgt tttctatcgc gtattaaat               109

<210> SEQ ID NO 23
<211> LENGTH: 25
<212> TYPE: DNA
<213> ORGANISM: Solanum tuberosum

<400> SEQUENCE: 23
gtttacatcg gtatatatcc tgcca                                          25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(18)
<223> OTHER INFORMATION: a, c, g, t, unknown or other

<400> SEQUENCE: 24
ygrcaggata tatnnnnnkg taaac                                          25

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gaccacaccc gtcctgtg                                                  18

<210> SEQ ID NO 26
<211> LENGTH: 25
<212> TYPE: DNA
<213> ORGANISM: Arabidopsis thaliana

<400> SEQUENCE: 26
```

```
gttgacatca cgatatatcc tgtca                                              25
```

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      nucleotide motif sequence
<220> FEATURE:
<221> NAME/KEY: modified_base
<222> LOCATION: (8)
<223> OTHER INFORMATION: a, c, g, t, unknown or other

<400> SEQUENCE: 27

```
vwwkachnbv vvatatatcc tgyca                                              25
```

<210> SEQ ID NO 28
<211> LENGTH: 25
<212> TYPE: DNA
<213> ORGANISM: Lycopersicon esculentum

<400> SEQUENCE: 28

```
cattaccaac aaatatatcc tggcc                                              25
```

<210> SEQ ID NO 29
<211> LENGTH: 25
<212> TYPE: DNA
<213> ORGANISM: Lycopersicon esculentum

<400> SEQUENCE: 29

```
ctctacctct gaatatatcc tgcgg                                              25
```

<210> SEQ ID NO 30
<211> LENGTH: 25
<212> TYPE: DNA
<213> ORGANISM: Lycopersicon esculentum

<400> SEQUENCE: 30

```
gcatacctct gaatatatcc tgcgg                                              25
```

<210> SEQ ID NO 31
<211> LENGTH: 25
<212> TYPE: DNA
<213> ORGANISM: Solanum tuberosum

<400> SEQUENCE: 31

```
gtttaccttu gcatatatcc tgcat                                              25
```

<210> SEQ ID NO 32
<211> LENGTH: 25
<212> TYPE: DNA
<213> ORGANISM: Medicago sativa

<400> SEQUENCE: 32

```
gtatacctct gtatacatcc tgccg                                              25
```

<210> SEQ ID NO 33
<211> LENGTH: 25
<212> TYPE: DNA
<213> ORGANISM: Hordeum vulgare

<400> SEQUENCE: 33

```
atataccaaa tgatacatcc tgccc                                              25
```

```
<210> SEQ ID NO 34
<211> LENGTH: 25
<212> TYPE: DNA
<213> ORGANISM: Oryza sativa

<400> SEQUENCE: 34
acttactcaa ggatatatcc tggct                                          25

<210> SEQ ID NO 35
<211> LENGTH: 25
<212> TYPE: DNA
<213> ORGANISM: Oryza sativa

<400> SEQUENCE: 35
cactacaaaa aaatatatcc tgcat                                          25

<210> SEQ ID NO 36
<211> LENGTH: 25
<212> TYPE: DNA
<213> ORGANISM: Oryza sativa

<400> SEQUENCE: 36
atgtacgtat atatatatcc tgtgt                                          25

<210> SEQ ID NO 37
<211> LENGTH: 25
<212> TYPE: DNA
<213> ORGANISM: Triticum aestivum

<400> SEQUENCE: 37
atatacggag caatatatcc tgtcc                                          25

<210> SEQ ID NO 38
<211> LENGTH: 25
<212> TYPE: DNA
<213> ORGANISM: Glycine max

<400> SEQUENCE: 38
aaaaactgtt ttatatatcc tgtca                                          25

<210> SEQ ID NO 39
<211> LENGTH: 25
<212> TYPE: DNA
<213> ORGANISM: Glycine max

<400> SEQUENCE: 39
aataactctg aaatatatcc tgtgt                                          25

<210> SEQ ID NO 40
<211> LENGTH: 25
<212> TYPE: DNA
<213> ORGANISM: Solanum tuberosum

<400> SEQUENCE: 40
acctacccca aaatatatcc tgcct                                          25

<210> SEQ ID NO 41
<211> LENGTH: 25
<212> TYPE: DNA
<213> ORGANISM: Lycopersicon esculentum

<400> SEQUENCE: 41
ggaaactgtc taatatatcc tgtga                                          25
```

```
<210> SEQ ID NO 42
<211> LENGTH: 25
<212> TYPE: DNA
<213> ORGANISM: Lycopersicon esculentum

<400> SEQUENCE: 42 acctaccccca aaatatatcc tgccc                              25

<210> SEQ ID NO 43
<211> LENGTH: 25
<212> TYPE: DNA
<213> ORGANISM: Lycopersicon esculentum

<400> SEQUENCE: 43
gtttagactt gtatatatcc tgccc                               25

<210> SEQ ID NO 44
<211> LENGTH: 25
<212> TYPE: DNA
<213> ORGANISM: Lycopersicon esculentum

<400> SEQUENCE: 44
tcttagaact caatatatcc tgtac                               25

<210> SEQ ID NO 45
<211> LENGTH: 25
<212> TYPE: DNA
<213> ORGANISM: Lycopersicon esculentum

<400> SEQUENCE: 45
cgttaacact gtatatatcc tgtaa                               25

<210> SEQ ID NO 46
<211> LENGTH: 25
<212> TYPE: DNA
<213> ORGANISM: Lycopersicon esculentum

<400> SEQUENCE: 46
gaattatttt gcatatatcc tgtaa                               25

<210> SEQ ID NO 47
<211> LENGTH: 25
<212> TYPE: DNA
<213> ORGANISM: Lycopersicon esculentum

<400> SEQUENCE: 47
ttgttcctgg ccatatatcc tgcca                               25

<210> SEQ ID NO 48
<211> LENGTH: 25
<212> TYPE: DNA
<213> ORGANISM: Lycopersicon esculentum

<400> SEQUENCE: 48
ggtaccatgt agatatatcc tgctt                               25

<210> SEQ ID NO 49
<211> LENGTH: 25
<212> TYPE: DNA
<213> ORGANISM: Medicago truncatula

<400> SEQUENCE: 49
gtatacctct gtatacctcc tgccg                               25
```

```
<210> SEQ ID NO 50
<211> LENGTH: 25
<212> TYPE: DNA
<213> ORGANISM: Zea maize

<400> SEQUENCE: 50
gcgtacgcat ttatatatcc tgtgg                                        25

<210> SEQ ID NO 51
<211> LENGTH: 25
<212> TYPE: DNA
<213> ORGANISM: Zea maize

<400> SEQUENCE: 51
gcttacgcat ttatatatcc tgtgg                                        25

<210> SEQ ID NO 52
<211> LENGTH: 25
<212> TYPE: DNA
<213> ORGANISM: Brassica rapa

<400> SEQUENCE: 52
ccctactgta taataaatcc tctag                                        25

<210> SEQ ID NO 53
<211> LENGTH: 25
<212> TYPE: DNA
<213> ORGANISM: Lycopersicon esculentum

<400> SEQUENCE: 53
ttgttcctgg ccatatatcc tgcca                                        25

<210> SEQ ID NO 54
<211> LENGTH: 25
<212> TYPE: DNA
<213> ORGANISM: Lycopersicon esculentum

<400> SEQUENCE: 54
ggtaccatgt agatatatcc tgctt                                        25

<210> SEQ ID NO 55
<211> LENGTH: 25
<212> TYPE: DNA
<213> ORGANISM: Lycopersicon esculentum

<400> SEQUENCE: 55
gttccggttg acatatatcc tgaca                                        25

<210> SEQ ID NO 56
<211> LENGTH: 25
<212> TYPE: DNA
<213> ORGANISM: Lycopersicon esculentum

<400> SEQUENCE: 56
cactaccgcc tcatagttcc tgcca                                        25

<210> SEQ ID NO 57
<211> LENGTH: 25
<212> TYPE: DNA
<213> ORGANISM: Glycine max

<400> SEQUENCE: 57
taaagcaaca ccatatatcc tgaca                                        25
```

```
<210> SEQ ID NO 58
<211> LENGTH: 25
<212> TYPE: DNA
<213> ORGANISM: Medicago truncatula

<400> SEQUENCE: 58
gattagacaa atatttatcc tgcca                                          25

<210> SEQ ID NO 59
<211> LENGTH: 25
<212> TYPE: DNA
<213> ORGANISM: Oryza sativa

<400> SEQUENCE: 59
ctctactacc cgagatgtcc tggca                                          25

<210> SEQ ID NO 60
<211> LENGTH: 25
<212> TYPE: DNA
<213> ORGANISM: Solanum tuberosum

<400> SEQUENCE: 60
gtttgacacg acatatatac tgcaa                                          25

<210> SEQ ID NO 61
<211> LENGTH: 25
<212> TYPE: DNA
<213> ORGANISM: Solanum tuberosum

<400> SEQUENCE: 61
gtttaccgtg gcacttatgt gatga                                          25

<210> SEQ ID NO 62
<211> LENGTH: 25
<212> TYPE: DNA
<213> ORGANISM: Solanum tuberosum

<400> SEQUENCE: 62
cattaccaac tattatatcc tggcc                                          25

<210> SEQ ID NO 63
<211> LENGTH: 25
<212> TYPE: DNA
<213> ORGANISM: Lycopersicon esculentum

<400> SEQUENCE: 63
gtttacttga agatatcacc tatgt                                          25

<210> SEQ ID NO 64
<211> LENGTH: 25
<212> TYPE: DNA
<213> ORGANISM: Lycopersicon esculentum

<400> SEQUENCE: 64
ttccatacga agagaagtcc tgtca                                          25

<210> SEQ ID NO 65
<211> LENGTH: 25
<212> TYPE: DNA
<213> ORGANISM: Lycopersicon esculentum

<400> SEQUENCE: 65
ttctagctgc aaatatatcc tggct                                          25
```

```
<210> SEQ ID NO 66
<211> LENGTH: 25
<212> TYPE: DNA
<213> ORGANISM: Lycopersicon esculentum

<400> SEQUENCE: 66
gttgacatgg atgaatatcc tgtca                                 25

<210> SEQ ID NO 67
<211> LENGTH: 25
<212> TYPE: DNA
<213> ORGANISM: Lycopersicon esculentum

<400> SEQUENCE: 67
gttcagctta gcatatatcc tgcat                                 25

<210> SEQ ID NO 68
<211> LENGTH: 25
<212> TYPE: DNA
<213> ORGANISM: Lycopersicon esculentum

<400> SEQUENCE: 68
ttccagaagt agatatatcc tgttg                                 25

<210> SEQ ID NO 69
<211> LENGTH: 25
<212> TYPE: DNA
<213> ORGANISM: Lycopersicon esculentum

<400> SEQUENCE: 69
tgattgcatc aaatatatcc tgcca                                 25

<210> SEQ ID NO 70
<211> LENGTH: 25
<212> TYPE: DNA
<213> ORGANISM: Lycopersicon esculentum

<400> SEQUENCE: 70
atccccaccc atttatatcc tgcca                                 25

<210> SEQ ID NO 71
<211> LENGTH: 25
<212> TYPE: DNA
<213> ORGANISM: Lycopersicon esculentum

<400> SEQUENCE: 71
catccccacc atttatatcc tgcca                                 25

<210> SEQ ID NO 72
<211> LENGTH: 25
<212> TYPE: DNA
<213> ORGANISM: Lycopersicon esculentum

<400> SEQUENCE: 72
gtcaggaagt gaatatatcc tgaca                                 25

<210> SEQ ID NO 73
<211> LENGTH: 25
<212> TYPE: DNA
<213> ORGANISM: Lycopersicon esculentum

<400> SEQUENCE: 73
gtttaaacca atatatatcc tgatt                                 25
```

```
<210> SEQ ID NO 74
<211> LENGTH: 25
<212> TYPE: DNA
<213> ORGANISM: Lycopersicon esculentum

<400> SEQUENCE: 74
agttataaac ttatatatcc tgttg                                    25

<210> SEQ ID NO 75
<211> LENGTH: 25
<212> TYPE: DNA
<213> ORGANISM: Lycopersicon esculentum

<400> SEQUENCE: 75
ctaaagttgt acataaatcc tgtct                                    25

<210> SEQ ID NO 76
<211> LENGTH: 25
<212> TYPE: DNA
<213> ORGANISM: Lycopersicon esculentum

<400> SEQUENCE: 76
ttctacacaa agacaaatcc tggcg                                    25

<210> SEQ ID NO 77
<211> LENGTH: 25
<212> TYPE: DNA
<213> ORGANISM: Lycopersicon esculentum

<400> SEQUENCE: 77
attaacaacg ttagaagtcc tggcg                                    25

<210> SEQ ID NO 78
<211> LENGTH: 25
<212> TYPE: DNA
<213> ORGANISM: Medicago truncatula

<400> SEQUENCE: 78
catgaccctg caatatgtcc tgtgg                                    25

<210> SEQ ID NO 79
<211> LENGTH: 25
<212> TYPE: DNA
<213> ORGANISM: Zea maize

<400> SEQUENCE: 79
aacttaaaga taagaagtcc tgcca                                    25

<210> SEQ ID NO 80
<211> LENGTH: 25
<212> TYPE: DNA
<213> ORGANISM: Avena sativa

<400> SEQUENCE: 80
ctgtacaata ggacaaatcc tgtcg                                    25

<210> SEQ ID NO 81
<211> LENGTH: 24
<212> TYPE: DNA
<213> ORGANISM: Solanum tuberosum

<400> SEQUENCE: 81
ttttacccgt gatatatccc agcc                                     24
```

```
<210> SEQ ID NO 82
<211> LENGTH: 24
<212> TYPE: DNA
<213> ORGANISM: Lycopersicon esculentum

<400> SEQUENCE: 82
gattgcatca aatatatcct gcca                                          24

<210> SEQ ID NO 83
<211> LENGTH: 24
<212> TYPE: DNA
<213> ORGANISM: Lycopersicon esculentum

<400> SEQUENCE: 83
aagtaccgat gatatatcct gcgt                                          24

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      nucleotide motif sequence
<220> FEATURE:
<221> NAME/KEY: modified_base
<222> LOCATION: (7)..(12)
<223> OTHER INFORMATION: a, c, g, t, unknown or other
<220> FEATURE:
<221> NAME/KEY: modified_base
<222> LOCATION: (25)
<223> OTHER INFORMATION: a, c, g, t, unknown or other

<400> SEQUENCE: 84
vhhkasnnnn nnakahrtcc tgbvn                                         25

<210> SEQ ID NO 85
<211> LENGTH: 25
<212> TYPE: DNA
<213> ORGANISM: Capsicum sp.

<400> SEQUENCE: 85
cattaccaac aaatatatcc tggcc                                         25

<210> SEQ ID NO 86
<211> LENGTH: 25
<212> TYPE: DNA
<213> ORGANISM: Solanum tuberosum

<400> SEQUENCE: 86
cattaccaac aaatatatcc tggcc                                         25

<210> SEQ ID NO 87
<211> LENGTH: 48
<212> TYPE: DNA
<213> ORGANISM: Agrobacterium tumefaciens

<400> SEQUENCE: 87
cttagagatc tcaaacaaac atacacagcg acttattcac aactagtc                48

<210> SEQ ID NO 88
<211> LENGTH: 24
<212> TYPE: DNA
<213> ORGANISM: Agrobacterium tumefaciens

<400> SEQUENCE: 88
caaacaaaca tacacagcga ctta                                          24
```

-continued

<210> SEQ ID NO 89
<211> LENGTH: 48
<212> TYPE: DNA
<213> ORGANISM: Unknown Organism
<220> FEATURE:
<223> OTHER INFORMATION: Description of Unknown Organism: UI-derived
      plant nucleotide

<400> SEQUENCE: 89
ttagagatct caaacaaaca tacacagcga cttattcaca actagtac               48

<210> SEQ ID NO 90
<211> LENGTH: 48
<212> TYPE: DNA
<213> ORGANISM: Unknown Organism
<220> FEATURE:
<223> OTHER INFORMATION: Description of Unknown Organism: UI-derived
      plant nucleotide

<400> SEQUENCE: 90
agagatctca aacaaacata cacagcgact tattcacaac tagtcaac               48

<210> SEQ ID NO 91
<211> LENGTH: 48
<212> TYPE: DNA
<213> ORGANISM: Agrobacterium tumefaciens

<400> SEQUENCE: 91
agaaacaatc aaacaaacat acacagcgac ttattcacac gagctcaa               48

<210> SEQ ID NO 92
<211> LENGTH: 48
<212> TYPE: DNA
<213> ORGANISM: Agrobacterium tumefaciens

<400> SEQUENCE: 92
gcccttttaa atatccgatt attctaataa acgctctttt ctcttagg               48

<210> SEQ ID NO 93
<211> LENGTH: 48
<212> TYPE: DNA
<213> ORGANISM: Agrobacterium tumefaciens

<400> SEQUENCE: 93
tgacgaactg acgaactgac gaactgacga actgacgaac tgacgaac               48

<210> SEQ ID NO 94
<211> LENGTH: 48
<212> TYPE: DNA
<213> ORGANISM: Agrobacterium tumefaciens

<400> SEQUENCE: 94
taacaattga acaattgaac aattgaacaa ttgaacaatt gaacaaac               48

<210> SEQ ID NO 95
<211> LENGTH: 48
<212> TYPE: DNA
<213> ORGANISM: Agrobacterium tumefaciens

<400> SEQUENCE: 95
tagacattgc acatccaaag gcaggcacgt acaaacgaat ttatttag               48

<210> SEQ ID NO 96
<211> LENGTH: 48

```
<212> TYPE: DNA
<213> ORGANISM: Agrobacterium tumefaciens

<400> SEQUENCE: 96
gaaggcacga aggcacgaag gcacgaaggc acgaaggcac gaaggcac                48

<210> SEQ ID NO 97
<211> LENGTH: 48
<212> TYPE: DNA
<213> ORGANISM: Agrobacterium tumefaciens

<400> SEQUENCE: 97
tcatcaccgc cgtcctaaac aaacatacct ccacacaaat ttatctac                48

<210> SEQ ID NO 98
<211> LENGTH: 48
<212> TYPE: DNA
<213> ORGANISM: Agrobacterium tumefaciens

<400> SEQUENCE: 98
agatctcaaa caaacataca cagcgactta ttcacaacta gtaccaac                48

<210> SEQ ID NO 99
<211> LENGTH: 48
<212> TYPE: DNA
<213> ORGANISM: Unknown Organism
<220> FEATURE:
<223> OTHER INFORMATION: Description of Unknown Organism: UI region of
      plant nucleotide sequence

<400> SEQUENCE: 99
tgacgaactg acgaactgac gaactgacga actgacgaac taccaaac                 48

<210> SEQ ID NO 100
<211> LENGTH: 48
<212> TYPE: DNA
<213> ORGANISM: Unknown Organism
<220> FEATURE:
<223> OTHER INFORMATION: Description of Unknown Organism: UI-derived
      plant nucleotide sequence

<400> SEQUENCE: 100
ctgacgaact gacgaactga cgaactgacg aactgacgaa ctaccaac                 48

<210> SEQ ID NO 101
<211> LENGTH: 48
<212> TYPE: DNA
<213> ORGANISM: Unknown Organism
<220> FEATURE:
<223> OTHER INFORMATION: Description of Unknown Organism: UI-like
      plant nucleotide sequence

<400> SEQUENCE: 101
tgtctttatc tcttgttgcc aaaactgctc tcgagtcgag tcaccaac                 48

<210> SEQ ID NO 102
<211> LENGTH: 50
<212> TYPE: DNA
<213> ORGANISM: Unknown Organism
<220> FEATURE:
<223> OTHER INFORMATION: Description of Unknown Organism: Downstream
      plant nucleotide sequence

<400> SEQUENCE: 102
gtcagcatca tcacaccaaa agttaggccc gaatagtttg aaattagaaa               50
```

```
<210> SEQ ID NO 103
<211> LENGTH: 52
<212> TYPE: DNA
<213> ORGANISM: Unknown Organism
<220> FEATURE:
<223> OTHER INFORMATION: Description of Unknown Organism: Downstream
      plant nucleotide sequence

<400> SEQUENCE: 103
aacactgata gtttaaaccg aaggcgggaa acgacaatct gatcatgagc gg          52

<210> SEQ ID NO 104
<211> LENGTH: 48
<212> TYPE: DNA
<213> ORGANISM: Unknown Organism
<220> FEATURE:
<223> OTHER INFORMATION: Description of Unknown Organism: Downstream
      plant nucleotide sequence

<400> SEQUENCE: 104
aataacaatc tcatgttagg taataatatc acccaatcaa cgcggcca              48

<210> SEQ ID NO 105
<211> LENGTH: 46
<212> TYPE: DNA
<213> ORGANISM: Unknown Organism
<220> FEATURE:
<223> OTHER INFORMATION: Description of Unknown Organism: Downstream
      plant nucleotide sequence

<400> SEQUENCE: 105
gcactaatat aagaaatgtc ctgtcagcac taatataaga aatgtc                46

<210> SEQ ID NO 106
<211> LENGTH: 50
<212> TYPE: DNA
<213> ORGANISM: Unknown Organism
<220> FEATURE:
<223> OTHER INFORMATION: Description of Unknown Organism: Downstream
      plant nucleotide sequence

<400> SEQUENCE: 106
aacctattcg ttaataggga cgtcgtacct acttcccttc cagcgcagca            50

<210> SEQ ID NO 107
<211> LENGTH: 10
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 107 hmhdwtmgkk                                                        10

<210> SEQ ID NO 108
<211> LENGTH: 63
<212> TYPE: DNA
<213> ORGANISM: Solanum tuberosum

<400> SEQUENCE: 108
gaggtataga ggcatgactg gcatgatcac taaattgatg cccacagagg agacttataa  60
cct                                                               63

<210> SEQ ID NO 109
<211> LENGTH: 47
<212> TYPE: DNA
```

<213> ORGANISM: Solanum tuberosum

<400> SEQUENCE: 109
gggcccggta cccggggatc aattcccgat ctagtaacat agatgac    47

<210> SEQ ID NO 110
<211> LENGTH: 71
<212> TYPE: DNA
<213> ORGANISM: Unknown Organism
<220> FEATURE:
<223> OTHER INFORMATION: Description of Unknown Organism: DI-region of
      plant nucleotide sequence

<400> SEQUENCE: 110
gggcccggtt cccggggatc aattgggccc ggtacccggg gatcaattcc cgatctagta    60
acatagatga c    71

<210> SEQ ID NO 111
<211> LENGTH: 47
<212> TYPE: DNA
<213> ORGANISM: Unknown Organism
<220> FEATURE:
<223> OTHER INFORMATION: Description of Unknown Organism: DI-region of
      plant nucleotide sequence

<400> SEQUENCE: 111
gggcccggta cccggaggag actccgatct acggcgccaa attcaag    47

<210> SEQ ID NO 112
<211> LENGTH: 50
<212> TYPE: DNA
<213> ORGANISM: Unknown Organism
<220> FEATURE:
<223> OTHER INFORMATION: Description of Unknown Organism: DI-region of
      plant nucleotide sequence

<400> SEQUENCE: 112
ctgaggacat tcagaagatt ggttatatcc tctttcaaga cgctaagcaa    50

<210> SEQ ID NO 113
<211> LENGTH: 63
<212> TYPE: DNA
<213> ORGANISM: Solanum tuberosum

<400> SEQUENCE: 113
gaggtataga ggcatgtctg gcgtgatcac taaattgatg cccgcagagg ggacttataa    60
cat    63

<210> SEQ ID NO 114
<211> LENGTH: 48
<212> TYPE: DNA
<213> ORGANISM: Medicago sativa

<400> SEQUENCE: 114
ggggcccggt acccgttagg gctagcccga aagggccgcg ggcagccc    48

<210> SEQ ID NO 115
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide repeat

<400> SEQUENCE: 115

```
cccg                                                                     4

<210> SEQ ID NO 116
<211> LENGTH: 103
<212> TYPE: DNA
<213> ORGANISM: Agrobacterium tumefaciens

<400> SEQUENCE: 116
tctccatatt gaccatcata ctcattgctg atccatgtag atttcccgga catgaagcca       60
tttacaattg aatatatcct gccgccgctg ccgctttgca ccc                       103

<210> SEQ ID NO 117
<211> LENGTH: 109
<212> TYPE: DNA
<213> ORGANISM: Agrobacterium tumefaciens

<400> SEQUENCE: 117
tgaattcagt acattaaaaa cgtccgcaat gtgttattaa gttgtctaag cgtcaatttg       60
tttacaccac aatatatcct gccaccagcc agccaacagc tccccgacc                 109

<210> SEQ ID NO 118
<211> LENGTH: 88
<212> TYPE: DNA
<213> ORGANISM: Agrobacterium tumefaciens

<400> SEQUENCE: 118
atctggtaat atagcaaaaa cgtgctcaaa aatcgcttca aagctcttgt acttagctcg       60
tttacaccac aatatatcct gccaccc                                          88

<210> SEQ ID NO 119
<211> LENGTH: 108
<212> TYPE: DNA
<213> ORGANISM: Agrobacterium tumefaciens

<400> SEQUENCE: 119
tacattttat attcgataaa gcatgcgtta aaacgacttc gcatgtccat atctaatctg       60
tttacatcac aatatatcct gccacccaag gagcgacgcc ttctggcc                  108

<210> SEQ ID NO 120
<211> LENGTH: 15
<212> TYPE: DNA
<213> ORGANISM: Artificial Sequence
<220> FEATURE:
<223> OTHER INFORMATION: Description of Artificial Sequence: Synthetic
      nucleotide consensus sequence

<400> SEQUENCE: 120
aytsawtkyk sayyw                                                        15

<210> SEQ ID NO 121
<211> LENGTH: 25
<212> TYPE: DNA
<213> ORGANISM: Artificial Sequence
<220> FEATURE:
<223> OTHER INFORMATION: Description of Artificial Sequence: Synthetic
      nucleotide consensus sequence

<400> SEQUENCE: 121
rtttacahhh saatatatcc tgccr                                             25

<210> SEQ ID NO 122
<211> LENGTH: 41
<212> TYPE: DNA
```

<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (3)..(13)
<223> OTHER INFORMATION: region may encompass 1-11 of the variable nucleotides a, c, g or t
<220> FEATURE:
<221> NAME/KEY: modified_base
<222> LOCATION: (16)..(26)
<223> OTHER INFORMATION: region may encompass 1-11 of the variable nucleotides a, c, g or t
<220> FEATURE:
<221> NAME/KEY: modified_base
<222> LOCATION: (29)..(39)
<223> OTHER INFORMATION: region may encompass 1-11 of the variable nucleotides a, c, g or t

<400> SEQUENCE: 122
ccnnnnnnnn nnccnnnnn nnnnnnccnn nnnnnnnnnc c                41

<210> SEQ ID NO 123
<211> LENGTH: 125
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 123
aaatctgatt gataaaggat cgatcctcta gagtcgacct gcagtactta cgtacaattg    60
tttacaccac aatatatcct gccaccggat atattgccta ggagccagcc aacagctccc   120
cgacc                                                               125

<210> SEQ ID NO 124
<211> LENGTH: 115
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 124
aaatctgatt gataaaggat cgatcctcta gagtcgacct gcagtactta cgtacaattg    60
tttacaccac aatatatcct gccacccta ggagccagcc aacagctccc cgacc          115

<210> SEQ ID NO 125
<211> LENGTH: 56
<212> TYPE: DNA
<213> ORGANISM: Medicago truncatula

<400> SEQUENCE: 125
gtttacacca caatatatcc tgccacccct aggagccagc caacagctcc ccgacc        56

<210> SEQ ID NO 126
<211> LENGTH: 128
<212> TYPE: DNA
<213> ORGANISM: Medicago truncatula

<400> SEQUENCE: 126
gtaaaaaata aaagtgaaaa ttcaatgaat taacacaaat ataaatgtaa tataaaattg    60
tatacctctg tatacatcct gccgccaagc ttccagccac ctaggagcca gccaacagct   120
ccccgacc                                                            128

<210> SEQ ID NO 127
<211> LENGTH: 125
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 127
aatggaggta agtgtttctg ctcagtgctg atagatgtaa atatctctgt tatgaagccg      60
tatacctctg tatacatcct gccgggatgt atacctagg ccagccagcc aacagctccc     120
cgacc                                                                125

<210> SEQ ID NO 128
<211> LENGTH: 115
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 128
tgttgaaggc ttggatgtga ttaagaaggc cgaggctgtt ggatctagtt cttgaagttc      60
attaccaaca aatatatcct ggccccccta ggagccagcc aacagctccc cgacc          115

<210> SEQ ID NO 129
<211> LENGTH: 11
<212> TYPE: DNA
<213> ORGANISM: Artificial Sequence
<220> FEATURE:
<223> OTHER INFORMATION: Description of Artificial Sequence: Synthetic
      nucleotide consensus sequence
<220> FEATURE:
<221> NAME/KEY: modified_base
<222> LOCATION: (7)..(10)
<223> OTHER INFORMATION: a, c, g, t, unknown or other

<400> SEQUENCE: 129
watcaannnn r                                                          11

<210> SEQ ID NO 130
<211> LENGTH: 19
<212> TYPE: DNA
<213> ORGANISM: Artificial Sequence
<220> FEATURE:
<223> OTHER INFORMATION: Description of Artificial Sequence: Synthetic
      nucleotide motif sequence
<220> FEATURE:
<221> NAME/KEY: modified_base
<222> LOCATION: (11)..(16)
<223> OTHER INFORMATION: a, c, g, t, unknown or other

<400> SEQUENCE: 130
caggatatat nnnnnngta                                                  19

<210> SEQ ID NO 131
<211> LENGTH: 316
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 131
ggctgcactg aacgtcagaa gccgactgca ctatagcagc ggaggggttg gatcaaagta      60
ctttgatccc gaggggaacc ctgtggttgg catgcacata caaatggacg aacggataaa     120

```
ccttttcacg cccttttaaa tatccgatta ttctaataaa cgctcttttc tcttagagat    180
ctcaaacaaa catacacagc gacttattca caactagtgt atacctctgt atacatcctg    240
ccggggcccg gtaccgtta gggctagccc gaaagggccg cgggcagccc gttagcccgc     300
ataactgcag cccggg                                                    316

<210> SEQ ID NO 132
<211> LENGTH: 354
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 132
cagtacttac gtacataaca aaaaaaaatt ctataaatta tatatatttt tcaaataatt    60
ctttacacag ttgattatca agtaaaaaa taaaagtgaa aattcaatga attaacacaa     120
atataaatgt aatataaaat tgtataccte tgtatacatc ctgccgccaa gcttccagcc    180
acctaggagc cagccaacag ctccccgacc ggcagctcgg cacaaaatca ccactcgata    240
caggcagccc atcagtccgg gacggcgtca gcgggagagc cgttgtaagg cggcagactt    300
tgctcatgtt accgatgcta ttcggaagaa cggcaactaa gctgccgggt ttga          354

<210> SEQ ID NO 133
<211> LENGTH: 92
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 133
cccgaaaaac gggacaggat gtgcaattgt aataccgtca cacgcgacgc tattacaatt    60
gccatctggt cagggcttcg ccccgacacc cc                                  92

<210> SEQ ID NO 134
<211> LENGTH: 64
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 134
cccgaaaaac gggacaggat gtgcaattgt aataccgtca cacgcgacgc tattacaatt    60
gcca                                                                 64

<210> SEQ ID NO 135
<211> LENGTH: 52
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 135
cccgaaaaac gggacaggat gtgcaattgt aataccgtca cacgcgacgc ta            52

<210> SEQ ID NO 136
<211> LENGTH: 86
<212> TYPE: DNA
<213> ORGANISM: Artificial Sequence
```

-continued

```
<220> FEATURE:
<223> OTHER INFORMATION: Description of Artificial Sequence: Synthetic
      nucleotide construct

<400> SEQUENCE: 136
aaaacgggac aggatgtgca attgtaatac cgtcacacgc gacgctatta caattgccat    60
ctggtcaggg cttcgccccg acaccc                                        86

<210> SEQ ID NO 137
<211> LENGTH: 92
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 137
accgaaaaac gggacaggat gtgcaattgt aataccgtca cacgcgacgc tattacaatt    60
gccatctggt cagggcttcg ccccgacacc cc                                 92

<210> SEQ ID NO 138
<211> LENGTH: 1024
<212> TYPE: DNA
<213> ORGANISM: Zea mays

<400> SEQUENCE: 138
atgacgcctc cggttggaaa taatcctccc tcaggctcag ccataagatt ggccaagttg    60
atgtctacca caagagcgcc ttctactcgc aaaacaaatt ccgtattctc tgcatatgct   120
caaggtatat attagaaaaa cagtagcaat agcattagca ttactaattg gttgtagatt   180
gggaagcatc atattgactg tagaataata cgaaaaatct gtttataaca gggttgaaaa   240
gaaaagctga agcctcttct agtcggattc agaatgtacg tgcacgtgcg cgtgggcatg   300
gatgtggccg cacatcacca tcatcatcaa cagctgaggc cgagaggcat tttattcaga   360
gtgtaagcag tagtaatgca aatggtacag ctacagatcc gagtcaagat gatatggcta   420
ttgttcatga accacaacca caaccacaac cacaaccaga accacaacca cagccacaac   480
ctgaacccga agaagaagca ccacagaaga gggcaaagaa gtgcacatcg gatgtatggc   540
agcatttcac caagaaggaa attgaagtgg aggtcgatgg aaagaaatac gttcaggtat   600
ggggacattg caactttcct aattgcaagg ctaagtatag ggctgagggt catcatggaa   660
caagcggatt tcgaaatcac ttgagaacat cacatagttt agttaaaggt cagttgtgtc   720
taaaaagtga aaggatcat ggcaaagaca taaatctcat tgagccttat aagtacgatg   780
aagtggttag cctaaagaag cttcatttgg caataatcat gcatgaatat cctttcaata   840
ttgtagaaca tgagtacttt gttgagtttg ttaagtctct gcgccctcac tttccaataa   900
agtcccgtgt cactgctaga aaatatatca tggatttgta tttggaagaa aaagaaaagt   960
tgtatggaaa actaaaagat gttcagtctc gcttcagtac aactatggat atgtggacat  1020
cttg                                                              1024

<210> SEQ ID NO 139
<211> LENGTH: 245
<212> TYPE: DNA
<213> ORGANISM: Zea mays

<400> SEQUENCE: 139
cagggatgaa agtaggatgg gaaaatcccg taccgaccgt tatcgtataa ccgatttgt    60 tagttttatc ccgatcgatt tcgaacccga ggtaaaaaac gaaaacggaa cggaaacggg   120
```

-continued

```
atatacaaaa cggtaaacgg aaacggaaac ggtagagcta gtttcccgac cgtttcaccg      180
ggatcccgtt tttaatcggg atgatcccgt ttcgttaccg tattttctaa ttcgggatga      240
ctgca                                                                  245
```

<210> SEQ ID NO 140
<211> LENGTH: 373
<212> TYPE: DNA
<213> ORGANISM: Zea mays

<400> SEQUENCE: 140

```
gtagacttat atggcttctt atgttagcca agagcccaag acttatcact tatgtgctac       60
attaaactat gtgtgctcca gatttatatg gattttatct atgtttaatt aagacttgtg      120
tttacaattt tttatatttg tttttaagtt ttgaatatat gttttcatgt gtgattttac      180
cgaacaaaaa taccggttcc cgtccgattt cgactttaac ccgaccggat cgtatcggtt      240
ttcgattacc gtatttatcc cgttcgtttt cgttaccggt atatcccgtt ttcgtttccg      300
tcccgcaagt taaatatgaa aatgaaaacg gtagaggtat tttaccgacc gttaccgacc      360
gttttcatcc cta                                                         373
```

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141

```
aggaaggaat tcccccggat cagc                                              24
```

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142

```
aggagcaagg tgagatgaca gg                                                22
```

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143

```
gaatcagcta atcagggagt gtg                                               23
```

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144

```
gccatgcgcg ttgtttcaca tcg                                               23
```

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gcatgctaag tgatccagat g                                          21

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ctgcagtcat cccgaattag                                            20

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ggaattcgcg tagacttata tggc                                       24

<210> SEQ ID NO 148
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tgatgaccaa aatcttgtca tcctc                                      25

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
gcatgctaag tgatccagat g                                          21

<210> SEQ ID NO 150
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
tgatgaccaa aatcttgtca tcctc                                      25

```
<210> SEQ ID NO 151
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
atcggttata cgataacggt cggtacg                                            27

<210> SEQ ID NO 152
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
acgaaaacgg aacggaaacg ggatatac                                           28

<210> SEQ ID NO 153
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
gattttccca tcctactttc atccctg                                            27

<210> SEQ ID NO 154
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gtagagctag tttcccgacc gtttcac                                            27

<210> SEQ ID NO 155
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gcacataagt gataagtctt gggctc                                             26

<210> SEQ ID NO 156
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
cgaccggatc gtatcggttt tcgattac                                           28

<210> SEQ ID NO 157
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
ctaacataag aagccatata agtctac                                          27

<210> SEQ ID NO 158
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
cggtagaggt attttaccga ccgttac                                          27

<210> SEQ ID NO 159
<211> LENGTH: 365
<212> TYPE: DNA
<213> ORGANISM: Unknown Organism
<220> FEATURE:
<223> OTHER INFORMATION: Description of Unknown Organism: Upstream
      junction of plant 1 nucleotide sequence

<400> SEQUENCE: 159
atagataaga ggagtttgtt acaaatttct actccacatt gatgagaaat atactaatgt      60
tatctcccct tccctctatt agtagatctt actctatgtt aaaacatgac aagaaataga    120
gagagaactc acactttctt cctcatctgc tacttctggt gccgaagaag ttttactcaa    180
agagtctaat ttaaggcaac gaagcatgtc cttttgtctc ttgcaagtat tgcaagaagg    240
caggacacac tttaaagaag tgttataagt catccatttt cctctgtctt caatttctta    300
aagaccaaaa gatccagtct tttgtgtcca tgttgataat tttactctaa tactcttagc    360
ttcca                                                                365

<210> SEQ ID NO 160
<211> LENGTH: 593
<212> TYPE: DNA
<213> ORGANISM: Unknown Organism
<220> FEATURE:
<223> OTHER INFORMATION: Description of Unknown Organism: Downstream
      junction of plant 1 nucleotide sequence

<400> SEQUENCE: 160
agcttccaca tcccaatttg gtgatcattc agcacataaa tttgctcaga agcaatagga     60
atatctcatg tctcttcctt ccaaataatc aattctcacc taggttcaat aatgatgttt    120
cttttagaga gatttctgac tatgatcatt ttgcaggttt aattagtaca ttttttgtag    180
ttaattatgt gttttttcat gcatgttcat cattgcaatt aggggtagat acttgaatct    240
tttacttggg ccactagcca catgactcca tttatggtgt ttataagcta tatcagtgta    300
tatcacattg tatttccata tatctcaggt gtaccatata tatctgtgat tatgtgaaag    360 accccccctaa tttgtgtcaa gactgacaat gctctgtcaa tcagtgtagc aaaaataaaa    420
ataaaataaa atcaaggatt agtacaacac catccaggaa cctttactag aaaattagta    480
taccatatga gtcttttaca gtttggatct atcatggagt aaaagaatac attgcagatt    540
aggattattc aaaatatgcc ttcttgcaat ctacgttgtg atcaacagat ata            593
```

```
<210> SEQ ID NO 161
<211> LENGTH: 178
<212> TYPE: DNA
<213> ORGANISM: Unknown Organism
<220> FEATURE:
<223> OTHER INFORMATION: Description of Unknown Organism: Upstream
      junction of plant 2 nucleotide sequence

<400> SEQUENCE: 161
attctcacca aaaattgagc tgattagata aaaaaagatc aatttgttaa gaccagcagc    60
agctcttcag taccatttca tgtcttaaca ggacatatat atatatatat agatatagag   120
agagaaagtg ggcaagactt gattttata gatctagaga gagaaaagga gagttggg     178

<210> SEQ ID NO 162
<211> LENGTH: 646
<212> TYPE: DNA
<213> ORGANISM: Unknown Organism
<220> FEATURE:
<223> OTHER INFORMATION: Description of Unknown Organism: Downstream
      junction of plant 2 nucleotide sequence

<400> SEQUENCE: 162
gagttgggga gaaaagaag ggattttac agatctagag agagaaagac ttgattcttc     60 ctatttctc ttcaccattt cctatgtttt ctctccctct cttttctctt tcttgatttc   120
tctataaatt ttcactcatt agtatattca tcactctcaa tttacctttt atataaaaat   180
aaaaacaata aaaattacta aatacattta attttaatta taaatagaaa ttattacact   240
attgattttt tatttgactt atttatttat tttagtctat tcgaaaaata tgtcttttttc   300 gttttctaat aactctttca ttttagtctt ttccatttaa tattacaaaa tttaaaaaaa   360
tgcattttgg tacctttta agattacaaa atttgaatat attatttact ttattaaatt   420
acgcatttaa tcaaaacaaa acaatcaaaa tgaaagcatt ttggtacctt ctagaatacg   480
tatatttaat ttgaaattac aaaatttgaa tatattcttt attttgttaa attacgtatt   540
tagtcaaaac aggacaataa aaaaaaacga aaggagtaat tactaataca ataacatttt   600
gactaaaatt aaaattaaag aaaaaaagga ttttggtacc ttctag                 646

<210> SEQ ID NO 163
<211> LENGTH: 379
<212> TYPE: DNA
<213> ORGANISM: Unknown Organism
<220> FEATURE:
<223> OTHER INFORMATION: Description of Unknown Organism: Upstream
      junction of plant 3 nucleotide sequence

<400> SEQUENCE: 163
tgtgatttag gaaggtaaga tgactttgca aggattgtct tcaaatggca taaatctaac    60
attcaaaatt aagtctattt ttaaacaata aaaatacatg agatttgcaa tttataagtc   120
aacgttgtca tataacccat tagttcggtt ttaaggatat gaatagaggt ttgaaacgtg   180
ttgcaaatgc tctcaactat ggacataacc cagtacccat gtcagcacta aggaccaccg   240
ggaaacaccc cccggaacca tcggaaccac cagataccac tagctacatg atggaggacc   300
cagaatcgaa tcagagcttt aaggatattc tcctgaacaa aaataaggag ataaatcaac   360
tacaccaccc taccggaac                                                 379

<210> SEQ ID NO 164
<211> LENGTH: 916
<212> TYPE: DNA
<213> ORGANISM: Unknown Organism
<220> FEATURE:
```

-continued

<223> OTHER INFORMATION: Description of Unknown Organism: Downstream
     junction of plant 3 nucleotide sequence

<400> SEQUENCE: 164

```
accggaactg gaacagcagg atcatacaga ggaccttgac atggactcca tccaactatc      60
gacagaggac aagcaacaaa tttaccaacc gtggaacctc tctgtgatag taaaggtatt     120
tggaaaaaaa tcgcccacgc atacttgaaa aacaagttgg ttgatctatg aagcgatca     180
gaacctctaa cactgataga ttttggctgt gaatacttta tattgcaaaa ttcaataatc     240
caaccagcct acataagtcc ctccatgagg gtccgtggtt catcgcagga aacttcctgt     300
tagtaaaaaa aatgggagcc aaactttgtg ccagacacat caacactcac ccatacaacg     360
atatgggcaa ggctgctgca actcccagcg gagttctatg acaggcaaat actagaaaag     420
gtaggggaa agctcgggtc cctcctaaaa attgatacct gcacctctgc tgcactaaga     480
ggacgttatg cacgcataca ggttcagcta gagaatccag tcaagacgac ggtcaaaatt     540
ggaaccatg ttcaaaaagt ggtatacgag ggggacaaaa tcctttgcac agaatgtggg     600
agactcggga acaccttatt gacctcatcc aggattttga gatgatgggt acacgattat     660
aaaaagttg atctatgatt taaatttgat cggtttaata tttaaatttt tactactaaa     720
aaccgttaaa ttttaaaat tataggtcta aaattaattc ttatatatat atatatacac     780
acaccaatta ccactagag aagtgttatc taatttaga aagaaaaata aaacaagata     840
aatataaatt tcaaatttct aacctcgtgg agagaggtgc acccagtcat aatcgcatta     900
tgtgatactt caagtg                                                    916
```

<210> SEQ ID NO 165
<211> LENGTH: 40
<212> TYPE: DNA
<213> ORGANISM: Unknown Organism
<220> FEATURE:
<223> OTHER INFORMATION: Description of Unknown Organism: Upstream
     junction of plant 4 nucleotide sequence

<400> SEQUENCE: 165

```
agatcgagtg agaagtagct ggaaacatca tgagtggcag                            40
```

<210> SEQ ID NO 166
<211> LENGTH: 647
<212> TYPE: DNA
<213> ORGANISM: Unknown Organism
<220> FEATURE:
<223> OTHER INFORMATION: Description of Unknown Organism: Downstream
     junction of plant 4 nucleotide sequence

<400> SEQUENCE: 166

```
agtggcagaa gtggaagaga taaaactcat gatgattgta atgagggtgg tggacaagat      60
gaatctggtg cccaaaacaa caaaaatact aatgccaaca aaagatcagg accaacggtg     120
ccacctaaaa ggggaagcat agcaaaacag atagtacgag atttaaagga tacatcaagc     180
tctctgagta ctgtattcac attgtttttc tttaacttcc ttctcatggc gattatatcg     240
acaaattatg agaacaaaat ataggaagtt acaacattg aggaaagcaa gtaaccagta     300
gtaataatct aaatgaccat tgttaatatt acttgacaac cagctaactc cacctccata     360
tgaagtaaca ctatccacaa cattcactaa aacactccca aaaagccag ctacagacat     420
tccaagtgtg aaaatagcca caacaaaact agacatgctt tttggaagtt cagagtaaag     480
gaactctacc aatccgattg cattgaaagc atcagctagt ccaagaagca cgtactgtgg     540
cacgaaccac atagccgaca tgttatatt tagactgtct tgtggatctt tctgatcaat     600
```

```
tgctatgccc cgccttatgc cttctgttat cgctgaaagt accatcg              647
```

<210> SEQ ID NO 167
<211> LENGTH: 1133
<212> TYPE: DNA
<213> ORGANISM: Agrobacterium tumefaciens

<400> SEQUENCE: 167

```
ttaactccgc tcgatatcga tgaagcattg tcgacctacc gctatgtcat tgaactgctg    60
ctgagcgaga acttggcaat tccgacagcc gtattgcgcc aacgcgtgcc ggttggtcga   120
ttgaccacat cgcagcgcgc gatgtcggac atgctcgcaa gccttccagt tgtacagtct   180
cccatgcacg agagagacgc atttgccgcg atgaaggaac gtggcatgtt gcatctcaca   240
ttgctgaata tgagaaccga tccgacaatg cgcctcctcg agcggaatct cagaatcgcc   300
atggaggaac tcgtcactat ctccaaattg gttagcgaag ccttggaggg gtgaagatgg   360
gaattcgcaa acccgctttg tctgtcgggg aggccaggcg gcttgccgcc gctcgacccg   420
aaatcgtcca tccttctttg cctgttgcca cccaaaactc gaccctgccg cagccgcctg   480
aaaatctcga cgaggaagat cgacgacctg ccccagccac cgccaagcgt tgtcacagct   540
ctgatcagca atcgatgctg accgtggatg ctttgagttc gacgacagcg ccagaaagga   600
tccaggtctt cctttcagcg cgcccgcccg cgcctgaagt atcgaagata tatgacaacc   660
tgatcctgca atacagtcct tccaagtcgc tacaaatgat cttgcgccgt gcgcttggcg   720
attttgaaaa catgctggcg gatggatcgt ttcgtgcggc tccgaagagt tatccgatcc   780
ctcacacagc tttcgaaaaa tcaatcatcg ttcagacctc ccgcatgttc ccggtctcgc   840
taatagaagc cgctcgcaat cactttgatc cattgggatt ggagaccgcc cgggcttttcg   900 gccacaagct ggctaccgca gcgcttgcat gttttctttgc tcgggagaag gcaacgaaca   960
gctgatctct caaaagatag gacccatcca atcactccgc agtgctgagt ttttcggata  1020
gtaccgagga aaggcagctt tgccaagccg catagcaatc tgctcacgtt gggaacagat  1080
tgctaaaggc gaaatgcacc tctacctcag gccgccatca cacccccgta cga         1133
```

<210> SEQ ID NO 168
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168

```
gtttaaacag cttcctccat agaagacgg                                  29
```

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169

```
ttaattaatc gtacgggggt gtgatgg                                    27
```

<210> SEQ ID NO 170
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 170
tgctcctgcc gagaaagtat                                                20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
agccaacgct atgtcctgat                                                20

<210> SEQ ID NO 172
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gaatcagcta atcagggag                                                 19

<210> SEQ ID NO 173
<211> LENGTH: 25
<212> TYPE: DNA
<213> ORGANISM: Homo sapiens

<400> SEQUENCE: 173
tggcaggata tatacatatg tacac                                          25

<210> SEQ ID NO 174
<211> LENGTH: 25
<212> TYPE: DNA
<213> ORGANISM: Homo sapiens

<400> SEQUENCE: 174
ctgcaggata tatttctcag taaac                                          25

<210> SEQ ID NO 175
<211> LENGTH: 25
<212> TYPE: DNA
<213> ORGANISM: Homo sapiens

<400> SEQUENCE: 175
tgccaggata tatacatggc taatg                                          25

<210> SEQ ID NO 176
<211> LENGTH: 25
<212> TYPE: DNA
<213> ORGANISM: Homo sapiens

<400> SEQUENCE: 176
ggccaggata tattacccag taatt                                          25

<210> SEQ ID NO 177
<211> LENGTH: 25
<212> TYPE: DNA
<213> ORGANISM: Homo sapiens
```

```
<400> SEQUENCE: 177
aggcaggact tctgtgtatg ttaac                                         25

<210> SEQ ID NO 178
<211> LENGTH: 25
<212> TYPE: DNA
<213> ORGANISM: Mus musculus

<400> SEQUENCE: 178
aggcaggact taatgtggtg taaac                                         25

<210> SEQ ID NO 179
<211> LENGTH: 25
<212> TYPE: DNA
<213> ORGANISM: Mus musculus

<400> SEQUENCE: 179
tggcaggata tatatcttgg taaat                                         25

<210> SEQ ID NO 180
<211> LENGTH: 25
<212> TYPE: DNA
<213> ORGANISM: Rattus norvegicus

<400> SEQUENCE: 180
tggcaggata tatggcattg tcatt                                         25

<210> SEQ ID NO 181
<211> LENGTH: 25
<212> TYPE: DNA
<213> ORGANISM: Neurospora crassa

<400> SEQUENCE: 181
atacaggata tataggtagg taaag                                         25

<210> SEQ ID NO 182
<211> LENGTH: 25
<212> TYPE: DNA
<213> ORGANISM: Saccharomyces bayanus

<400> SEQUENCE: 182
agacaggata tattggaagg tattc                                         25

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
gccatgcgcg ttgtttcaca tcg                                           23

<210> SEQ ID NO 184
<211> LENGTH: 59
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 184
tccttcatag ctacactttc taaggtacg atagattttg gatcaaccac acacacttc     59
```

<210> SEQ ID NO 185
<211> LENGTH: 59
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 185
gtaaaaaata aaagtgaaaa ttcaatgaat taacacaaat ataaatgtaa tataaaatt        59

<210> SEQ ID NO 186
<211> LENGTH: 59
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 186
tgttgaaggc ttggatgtga ttaagaaggc cgaggctgtt ggatctagtt cttgaagtt        59

<210> SEQ ID NO 187
<211> LENGTH: 59
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 187
ccacaatata tcctgccacc ggatatattg cctaggagcc agccaacagc tccccgacc        59

<210> SEQ ID NO 188
<211> LENGTH: 64
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 188
cctctgtata catcctgccg ccaagcttcc agccacctag gagccagcca acagctcccc        60
gacc                                                                   64

<210> SEQ ID NO 189
<211> LENGTH: 25
<212> TYPE: DNA
<213> ORGANISM: Brassica rapa

<400> SEQUENCE: 189
ccctactgta taataaatcc tgtag                                             25

<210> SEQ ID NO 190
<211> LENGTH: 25
<212> TYPE: DNA
<213> ORGANISM: Brassica rapa

<400> SEQUENCE: 190
ctctactgta taataaatcc tgtcg                                             25

<210> SEQ ID NO 191
<211> LENGTH: 14
<212> TYPE: DNA
<213> ORGANISM: Unknown Organism
<220> FEATURE:

<223> OTHER INFORMATION: Description of Unknown Organism: Alternate
      final cleavage site nucleotide sequence

<400> SEQUENCE: 191
cccgaaaaac ggga                                                      14

<210> SEQ ID NO 192
<211> LENGTH: 14
<212> TYPE: DNA
<213> ORGANISM: Arabidopsis thaliana

<400> SEQUENCE: 192
accgaaaaac ggga                                                      14

<210> SEQ ID NO 193
<211> LENGTH: 25
<212> TYPE: DNA
<213> ORGANISM: Zea mays

<400> SEQUENCE: 193
gcgtacgcat ttatatatcc tgtgg                                          25

<210> SEQ ID NO 194
<211> LENGTH: 25
<212> TYPE: DNA
<213> ORGANISM: Zea mays

<400> SEQUENCE: 194
gcttacgcat ttatatatcc tgtgg                                          25

<210> SEQ ID NO 195
<211> LENGTH: 25
<212> TYPE: DNA
<213> ORGANISM: Glycine max

<400> SEQUENCE: 195
aaatactgtt ttatatatcc tgtca                                          25

<210> SEQ ID NO 196
<211> LENGTH: 25
<212> TYPE: DNA
<213> ORGANISM: Glycine max

<400> SEQUENCE: 196
aattactctg aaatatatcc tgtgt                                          25

<210> SEQ ID NO 197
<211> LENGTH: 25
<212> TYPE: DNA
<213> ORGANISM: Brassica rapa

<400> SEQUENCE: 197
tggaactgtt ctatatgtcc tgtca                                          25

<210> SEQ ID NO 198
<211> LENGTH: 25
<212> TYPE: DNA
<213> ORGANISM: Brassica rapa

<400> SEQUENCE: 198
aggaactgtt ctatatgtcc tgtca                                          25

<210> SEQ ID NO 199
<211> LENGTH: 48

<212> TYPE: DNA
<213> ORGANISM: Agrobacterium tumefaciens

<400> SEQUENCE: 199
cttagagatc tcaaacaaac atacacagcg acttattcac aactagtc         48

<210> SEQ ID NO 200
<211> LENGTH: 48
<212> TYPE: DNA
<213> ORGANISM: Agrobacterium tumefaciens

<400> SEQUENCE: 200
agaaacaatc aaacaaacat acacagcgac ttattcacac gagctcaa         48

<210> SEQ ID NO 201
<211> LENGTH: 48
<212> TYPE: DNA
<213> ORGANISM: Agrobacterium tumefaciens

<400> SEQUENCE: 201
gcccttttaa atatccgatt attctaataa acgctctttt ctcttagg         48

<210> SEQ ID NO 202
<211> LENGTH: 48
<212> TYPE: DNA
<213> ORGANISM: Agrobacterium tumefaciens

<400> SEQUENCE: 202
tgacgaactg acgaactgac gaactgacga actgacgaac tgacgaac         48

<210> SEQ ID NO 203
<211> LENGTH: 48
<212> TYPE: DNA
<213> ORGANISM: Agrobacterium tumefaciens

<400> SEQUENCE: 203
taacaattga acaattgaac aattgaacaa ttgaacaatt gaacaaac         48

<210> SEQ ID NO 204
<211> LENGTH: 48
<212> TYPE: DNA
<213> ORGANISM: Agrobacterium tumefaciens

<400> SEQUENCE: 204
tagacattgc acatccaaag gcaggcacgt acaaacgaat ttatttag         48

<210> SEQ ID NO 205
<211> LENGTH: 48
<212> TYPE: DNA
<213> ORGANISM: Agrobacterium tumefaciens

<400> SEQUENCE: 205
gaaggcacga aggcacgaag gcacgaaggc acgaaggcac gaaggcac         48

<210> SEQ ID NO 206
<211> LENGTH: 48
<212> TYPE: DNA
<213> ORGANISM: Agrobacterium tumefaciens

<400> SEQUENCE: 206
tcatcaccgc cgtcctaaac aaacataccct ccacacaaat ttatctac         48

<210> SEQ ID NO 207
<211> LENGTH: 48

```
<212> TYPE: DNA
<213> ORGANISM: Agrobacterium tumefaciens

<400> SEQUENCE: 207
agatctcaaa caaacataca cagcgactta ttcacaacta gtaccaac                    48

<210> SEQ ID NO 208
<211> LENGTH: 48
<212> TYPE: DNA
<213> ORGANISM: Unknown Organism
<220> FEATURE:
<223> OTHER INFORMATION: Description of Unknown Organism: UI region of
      plant nucleotide sequence

<400> SEQUENCE: 208
tgacgaactg acgaactgac gaactgacga actgacgaac taccaaac                    48

<210> SEQ ID NO 209
<211> LENGTH: 48
<212> TYPE: DNA
<213> ORGANISM: Unknown Organism
<220> FEATURE:
<223> OTHER INFORMATION: Description of Unknown Organism: UI-derived
      plant nucleotide sequence

<400> SEQUENCE: 209
ctgacgaact gacgaactga cgaactgacg aactgacgaa ctaccaaac                   48

<210> SEQ ID NO 210
<211> LENGTH: 48
<212> TYPE: DNA
<213> ORGANISM: Unknown Organism
<220> FEATURE:
<223> OTHER INFORMATION: Description of Unknown Organism: UI-like
      plant nucleotide sequence

<400> SEQUENCE: 210
tgtctttatc tcttgttgcc aaaactgctc tcgagtcgag tcaccaac                    48

<210> SEQ ID NO 211
<211> LENGTH: 59
<212> TYPE: DNA
<213> ORGANISM: Agrobacterium tumefaciens

<400> SEQUENCE: 211
tctccatatt gaccatcata ctcattgctg atccatgtag atttcccgga catgaagcc        59

<210> SEQ ID NO 212
<211> LENGTH: 59
<212> TYPE: DNA
<213> ORGANISM: Agrobacterium tumefaciens

<400> SEQUENCE: 212
tgaattcagt acattaaaaa cgtccgcaat gtgttattaa gttgtctaag cgtcaattt        59

<210> SEQ ID NO 213
<211> LENGTH: 59
<212> TYPE: DNA
<213> ORGANISM: Agrobacterium tumefaciens

<400> SEQUENCE: 213
atctggtaat atagcaaaaa cgtgctcaaa atcgcttca aagctcttgt acttagctc         59

<210> SEQ ID NO 214
<211> LENGTH: 59
<212> TYPE: DNA
```

<213> ORGANISM: Agrobacterium tumefaciens

<400> SEQUENCE: 214
tacattttat attcgataaa gcatgcgtta aaacgacttc gcatgtccat atctaatct    59

<210> SEQ ID NO 215
<211> LENGTH: 26
<212> TYPE: DNA
<213> ORGANISM: Agrobacterium tumefaciens

<400> SEQUENCE: 215
cctgccgccg ctgccgcttt gcaccc    26

<210> SEQ ID NO 216
<211> LENGTH: 32
<212> TYPE: DNA
<213> ORGANISM: Agrobacterium tumefaciens

<400> SEQUENCE: 216
cctgccacca gccagccaac agctccccga cc    32

<210> SEQ ID NO 217
<211> LENGTH: 22
<212> TYPE: DNA
<213> ORGANISM: Agrobacterium tumefaciens

<400> SEQUENCE: 217
ccacaatata tcctgccacc cc    22

<210> SEQ ID NO 218
<211> LENGTH: 31
<212> TYPE: DNA
<213> ORGANISM: Agrobacterium tumefaciens

<400> SEQUENCE: 218
cctgccaccc aaggagcgac gccttctggc c    31

<210> SEQ ID NO 219
<211> LENGTH: 657
<212> TYPE: DNA
<213> ORGANISM: Agrobacterium tumefaciens

<400> SEQUENCE: 219
ggtaccggtc cggctctctc cggcttgtct ctttccggtc gccgagccct tgccgccacg    60
aaaccgtttg cgacttcct cgaaggctgc ctgaagctgt gactcctcga tgtcgatttc   120
accaagaccg gccttcaacg caatcctgcc gattcgttcg gcctcgcgtg tttcggcctg   180
tttcagctgg tcctgcaatc tggcaatttc ttccctgatc ttcgatgatg gtttcttcat   240
tccggtcgca tctccctgga atcctgcgg cgtctgttcc gctgcaagat ttcctcaaaa   300
gcacttcgga aggaatgtgc agatctgcac gtcggcaaag ccgacacttt ggaggatgat   360
cccgccgctc gacgagagcg gatccaaggg cgcaattata cgtcgctgac gcgacgcctt   420
gcgtaggggg ccaaacaggg gcccactgtg gcctcaccgc tcccgacgaa cgacgttcaa   480
acgggagctt ttaccgccgt ggccatcgcc cacttctcag ccagcatcgt cagccgcggc   540
gacggccgca gcgtggtgct gtctgcggcc taccagcact gcgcgaagat ggaatacgag   600
cgcgaggccc gcaccatcga ctacacccgc aagcaagggc tggtgcatca ggaattc      657

<210> SEQ ID NO 220
<211> LENGTH: 437
<212> TYPE: DNA

<213> ORGANISM: Agrobacterium tumefaciens

<400> SEQUENCE: 220

| | | |
|---|---|---|
| ggggtgtcgg ggcgaagccc tgaccagatg gcaattgtaa tagcgtcgcg tgtgacggta | 60 |
| ttacaattgc acatcctgtc ccgttttttcg ggtaaagctt ggggtgtcgg ggcgaagccc | 120 |
| tgaccagatg gcaattgtaa tagcgtcgcg tgtgacggta ttacaattgc acatcctgtc | 180 |
| ccgttttttcg ggctacagat gaacaaaaac aaaacagaaa ttgatttctg agaagaagaa | 240 |
| gaagaagagg aagcattcac atttatcacc gattacagta gggtcaaatt cagtaggcaa | 300 |
| gagaatcaaa atcagaatag atgagatgag atatgaaaca acgtttatac accataacac | 360 |
| gattcataat agaatgtagg gaaacatgca tgaaatcaga ataattgga ggagatgagt | 420 |
| aaaagttacc atggtac | 437 |

<210> SEQ ID NO 221
<211> LENGTH: 346
<212> TYPE: DNA
<213> ORGANISM: Agrobacterium tumefaciens

<400> SEQUENCE: 221

| | | |
|---|---|---|
| ggggtgtcgg ggcgaagccc tgaccagatg gcaattgtaa tagcgtcgcg tgtgacggta | 60 |
| ttacaattgc acatcctgtc ccgttttttcg ggctcgagag tggtgatttt gtgccgagct | 120 |
| gccggtcggg gagctgttgg ctggctggaa gctttggcag gatatatttg ttggtaatgg | 180 |
| aagtgtgtgt ggttgatcca aaatctatcg tacctttaga aagtgtagct atgaaggata | 240 |
| gtctcactta tgaagaacta cctattgaga ttcttgatcg tcaggtccga aggttgagaa | 300 |
| aaatagaagt cgcttcagtt acggctttgt ggaggagtaa gggtac | 346 |

<210> SEQ ID NO 222
<211> LENGTH: 346
<212> TYPE: DNA
<213> ORGANISM: Agrobacterium tumefaciens

<400> SEQUENCE: 222

| | | |
|---|---|---|
| ggggtgtcgg ggcgaagccc tgaccagatg gcaattgtaa tagcgtcgcg tgtgacggta | 60 |
| ttacaattgc acatcctgtc ccgttttttcg ggctcgagag tggtgatttt gtgccgagct | 120 |
| gccggtcggg gagctgttgg ctggctggaa gctttggcag gatatatacc ggtgtaaacg | 180 |
| aagtgtgtgt ggttgatcca aaatctatcg tacctttaga aagtgtagct atgaaggata | 240 |
| gtctcactta tgaagaacta cctattgaga ttcttgatcg tcaggtccga aggttgagaa | 300 |
| aaatagaagt cgcttcagtt acggctttgt ggaggagtaa gggtac | 346 |

<210> SEQ ID NO 223
<211> LENGTH: 657
<212> TYPE: DNA
<213> ORGANISM: Agrobacterium tumefaciens

<400> SEQUENCE: 223

| | | |
|---|---|---|
| atgtcaaact ttatacttaa accgggcgaa aaactacccc aagacaaact agaagaatta | 60 |
| aaaaaaatta atgatgctgt taaaaaaacg aaaaatttct caaatactt gattgactta | 120 |
| agaaaacttt tcaaattga cgaagtccaa gtaacttctg aatcaaaact cttttttagct | 180 |
| ggtttttttag aaggtgaagc ttctctaaat attagcacta aaaagctcgc tacttctaaa | 240 |
| tttggtttgg tggttgatcc tgaattcaat gtgactcaac atgtcaatgg ggttaaagtg | 300 |
| ctttatttag cattagaagt atttaaaaca gggcgtattc gtcataaaag tggtagtaat | 360 |

```
gcaactttag ttttaactat tgacaatcgt caaagtttgg aagaaaaagt aattccttt       420 tatgaacaat atgttgttgc cttcagttct ccagaaaaag tcaaacgtgt agctaatttt     480
aaagctttgt tagaattatt taataatgac gctcaccaag atttagaaca attggtaaac     540
aaaatcctac caatttggga tcaaatgcgt aaacaacaag acaaagtaa cgaaggcttt      600 cctaatttag aagcagctca agactttgct cgtaattata aaaaaggtat aaagtag        657
```

<210> SEQ ID NO 224
<211> LENGTH: 218
<212> TYPE: PRT
<213> ORGANISM: Agrobacterium tumefaciens

<400> SEQUENCE: 224

```
Met Ser Asn Phe Ile Leu Lys Pro Gly Glu Lys Leu Pro Gln Asp Lys
  1               5                  10                  15

Leu Glu Glu Leu Lys Lys Ile Asn Asp Ala Val Lys Lys Thr Lys Asn
             20                  25                  30

Phe Ser Lys Tyr Leu Ile Asp Leu Arg Lys Leu Phe Gln Ile Asp Glu
         35                  40                  45

Val Gln Val Thr Ser Glu Ser Lys Leu Phe Leu Ala Gly Phe Leu Glu
     50                  55                  60

Gly Glu Ala Ser Leu Asn Ile Ser Thr Lys Lys Leu Ala Thr Ser Lys
 65                  70                  75                  80

Phe Gly Leu Val Val Asp Pro Glu Phe Asn Val Thr Gln His Val Asn
                 85                  90                  95

Gly Val Lys Val Leu Tyr Leu Ala Leu Glu Val Phe Lys Thr Gly Arg
            100                 105                 110

Ile Arg His Lys Ser Gly Ser Asn Ala Thr Leu Val Leu Thr Ile Asp
        115                 120                 125

Asn Arg Gln Ser Leu Glu Glu Lys Val Ile Pro Phe Tyr Glu Gln Tyr
    130                 135                 140

Val Val Ala Phe Ser Ser Pro Glu Lys Val Lys Arg Val Ala Asn Phe
145                 150                 155                 160

Lys Ala Leu Leu Glu Leu Phe Asn Asn Asp Ala His Gln Asp Leu Glu
                165                 170                 175

Gln Leu Val Asn Lys Ile Leu Pro Ile Trp Asp Gln Met Arg Lys Gln
            180                 185                 190

Gln Gly Gln Ser Asn Glu Gly Phe Pro Asn Leu Glu Ala Ala Gln Asp
        195                 200                 205

Phe Ala Arg Asn Tyr Lys Lys Gly Ile Lys
    210                 215
```

<210> SEQ ID NO 225
<211> LENGTH: 269
<212> TYPE: DNA
<213> ORGANISM: Agrobacterium tumefaciens

<400> SEQUENCE: 225

```
agcttcctcc atagaagacg aaagatctg aacctgcccc gccgtagcat ttcctcgtcg       60
tggcagatgg gaatctagcc atatacaaaa cgaaatcaag aacacataag ggatatttat    120
ttttatatta ttcaattga aattatatta caataaaatt gaatataaa gtcaggtaat      180 tactacatta cttatgaatt atcgcaaaat catcacacaca aataaaagta cagacacact    240
tccgcttcac aaaatcgaca ggataagga                                        269
```

<210> SEQ ID NO 226

```
<211> LENGTH: 26
<212> TYPE: DNA
<213> ORGANISM: Agrobacterium tumefaciens

<400> SEQUENCE: 226
taactataac ggtcctaagg tagcga                                              26

<210> SEQ ID NO 227
<211> LENGTH: 210
<212> TYPE: PRT
<213> ORGANISM: Agrobacterium tumefaciens

<400> SEQUENCE: 227
```

Met Ser Asn Phe Ile Leu Lys Pro Gly Glu Lys Leu Pro Gln Asp Lys
1               5                   10                  15

Leu Glu Glu Leu Lys Lys Ile Asn Asp Ala Val Lys Lys Thr Lys Asn
            20                  25                  30

Phe Ser Lys Tyr Leu Ile Asp Leu Arg Lys Leu Phe Gln Ile Asp Glu
        35                  40                  45

Val Gln Val Thr Ser Glu Ser Lys Leu Phe Leu Ala Gly Phe Leu Glu
    50                  55                  60

Gly Glu Ala Ser Leu Asn Ile Ser Thr Lys Lys Leu Ala Thr Ser Lys
65                  70                  75                  80

Phe Gly Leu Val Val Asp Pro Glu Phe Asn Val Thr Gln His Val Asn
                85                  90                  95

Gly Val Lys Val Leu Tyr Leu Ala Leu Glu Val Phe Lys Thr Gly Arg
            100                 105                 110

Ile Arg His Lys Ser Gly Ser Asn Ala Thr Leu Val Leu Ala Ile Asp
        115                 120                 125

Asn Arg Gln Ser Leu Glu Glu Lys Val Ile Pro Phe Tyr Glu Gln Tyr
    130                 135                 140

Val Val Ala Phe Ser Ser Pro Glu Lys Val Lys Arg Val Ala Asn Phe
145                 150                 155                 160

Lys Ala Leu Leu Glu Leu Phe Asn Asn Asp Ala His Gln Asp Leu Glu
                165                 170                 175

Gln Leu Val Asn Lys Ile Leu Pro Ile Trp Asp Gln Met Arg Lys Gln
            180                 185                 190

Gln Gly Gln Ser Asn Glu Gly Phe Pro Asn Leu Glu Ala Ala Gln Asp
        195                 200                 205

Phe Ala
    210

```
<210> SEQ ID NO 228
<211> LENGTH: 37
<212> TYPE: DNA
<213> ORGANISM: Agrobacterium tumefaciens

<400> SEQUENCE: 228
aacgctcagt agatgttttc ttgggtctac cgtttaa                                  37

<210> SEQ ID NO 229
<211> LENGTH: 25
<212> TYPE: DNA
<213> ORGANISM: Solanum tuberosum

<400> SEQUENCE: 229
gtttacagta ccatatatcc tgtca                                               25

<210> SEQ ID NO 230
```

```
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gtcaatcagc aaacagcaac agtagttatt gtctgtgaag atatgtaggt acctttcacc        60
cac                                                                     63
```